US008697061B2

(12) United States Patent
Natunen et al.

(10) Patent No.: US 8,697,061 B2
(45) Date of Patent: Apr. 15, 2014

(54) TUMOR SPECIFIC OLIGOSACCHARIDE EPITOPES AND USE THEREOF

(75) Inventors: Jari Natunen, Vantaa (FI); Tero Satomaa, Helsinki (FI)

(73) Assignee: Glykos Finland Oy, Helsinki (FI)

( * ) Notice: Subject to any disclaimer, the term of this patent is extended or adjusted under 35 U.S.C. 154(b) by 1143 days.

(21) Appl. No.: 10/525,011

(22) PCT Filed: Aug. 20, 2003

(86) PCT No.: PCT/FI03/00615
§ 371 (c)(1),
(2), (4) Date: Aug. 15, 2005

(87) PCT Pub. No.: WO2004/017810
PCT Pub. Date: Mar. 4, 2004

(65) Prior Publication Data
US 2006/0014672 A1 Jan. 19, 2006

(30) Foreign Application Priority Data
Aug. 20, 2002 (WO) .................. PCT/FI02/00681

(51) Int. Cl.
*A61K 38/43* (2006.01)
*A61K 38/14* (2006.01)
*A61K 31/715* (2006.01)

(52) U.S. Cl.
USPC ....... 424/94.5; 424/94.1; 514/19.3; 514/20.9; 514/54

(58) Field of Classification Search
None
See application file for complete search history.

(56) References Cited

U.S. PATENT DOCUMENTS

| 6,075,134 | A | 6/2000 | Bertozzi et al. | |
|---|---|---|---|---|
| 7,265,084 | B2 * | 9/2007 | DeFrees et al. | 514/6 |
| 2004/0142856 | A1 * | 7/2004 | DeFrees et al. | 514/8 |
| 2004/0253651 | A1 * | 12/2004 | Saarinen et al. | 435/7.23 |

FOREIGN PATENT DOCUMENTS

| DE | 3807594 A1 | 9/1989 |
|---|---|---|
| EP | 0255342 A1 | 3/1988 |
| EP | 0334962 A1 | 4/1989 |
| JP | 2264864 A | 10/1990 |
| JP | 20 00191685 | 11/2000 |
| WO | WO 9114697 A1 | 10/1991 |
| WO | WO 0021552 A1 | 4/2000 |
| WO | WO 0187321 A2 | 11/2001 |
| WO | WO 03016915 A1 | 2/2003 |

OTHER PUBLICATIONS

Hanisch et al (Cancer Research, 1993, 53:4791-4796).*
Bulter et al (Chembiochem, 2001, 2:884-894).*
Ramakrishnan and Qasba (J of Biological Chemistry, Mar. 2002, 277:20833-20839).*
Hang et al (J Am Chem Society, Jan. 2001, 123:1242-1243).*
Johnson, P.J. et al., British Journal of Cancer, vol. 83, No. 10; pp. 1330-1337 (2000).
Johnson, P.J. et al., British Journal of Cancer, vol. 81, No. 7; pp. 1188-1195 (1999).
Dennis, J.W. et al., Eur. J. Biochem., vol. 161, pp. 359-373 (1986).
Yamashita, K. et al., Cancer Research, vol. 43, pp. 5059-5063 (Nov. 1983).
Yamashita, K. et al., J. Biochem., vol. 90, pp. 1281-1289 (1981).
Chechik, Boris E. et al., Histochemical Journal, vol. 24, pp. 15-20 (1992).
Nixon Volman, Gail et al., Molecular Immunology, vol. 24, No. 8, pp. 871-888 (1989).
Endo, T. et al., Eur. J. Biochem., vol. 236, pp. 579-590 (1996).
Rebbaa, a. et al., Clinical Cancer Research, vol. 5, pp. 3661-3668 (1999).
Ohtani, N. et al., Jpn. J. Electroph., vol. 46:163, pp. 2-6 (2002).
Meichenin, M. et al., Cancer Research, vol. 60, pp. 5499-5507 (Oct. 2000).
Hanisch, F-G. et al., Cancer Research, vol. 53, pp. 4791-4796 (Oct. 1993).
Nakayama, J. et al., Jpn. J. Cancer Research, vol. 81, pp. 388-395 (Apr. 1990).
Jie et al., Glycobiology, vol. 4, No. 3, pp. 251-257 (1994).
Database WPI, Week 199049, Derwent Publications Ltd., London , GB., AN 1990-365935 (1990).
Holmes, Eric H. et al., Archives of biochemistry and biophysics; vol. 288, No. 1 ; pp. 87-96 (1991).
Derwent Publications Ltd., London, GB., AN 1990-365935.
Patent Abstracts of Japan, vol. 2000, No. 10; Abstract of JP 20 00191685A (Nov. 2000).
Bulter, Thomas et al., Chembiochem., vol. 2, pp. 884-894 (2001).
Chen, Z.C. et al., Glycobiology, vol. 11, No. 7, pp. 577-586 (2001).
Henion, T.R. et al., Vaccine, vol. 15, No. 11, pp. 1174-1182 (1997).
Sadamoto, R. et al., Methods in enzymology, vol. 362, pp. 273-286 (2003).
Lemieux, G.A. et al., Chemistry & Biology, vol. 8, pp. 265-275 (2001).
Saxon, E. et al., Annu. Rev. Cell Dev. Biol., vol. 17, pp. 1-23 (2001).

* cited by examiner

*Primary Examiner* — Laura B Goddard
(74) *Attorney, Agent, or Firm* — Birch, Stewart, Kolasch & Birch, LLP

(57) ABSTRACT

The present invention describes oligosaccharide sequences, which are specifically expressed by human tumors. The present invention is related to a method of determining an oligosaccharide sequence, which comprises a tumor specific terminal N-acetylglucosamine residue, in a biological sample, the presence of said sequence in said sample being an indication of the presence of cancer. The present invention provides antigenic substances comprising said oligosaccharide sequences in a polyvalent form and it further provides diagnostic agents, pharmaceutical compositions and cancer vaccines comprising said oligosaccharide sequences or substances binding to said oligosaccharide sequences. The present invention is also related to methods for the treatment of cancer.

27 Claims, 16 Drawing Sheets

TUMOR SPECIFIC OLIGOSACCHARIDE EPITOPES AND USE THEREOF

FIELD OF THE INVENTION

The present invention relates to oligosaccharide sequences, which are specifically expressed by human tumors. The present invention describes methods for the detection of the tumor specific oligosaccharide structures disclosed in the invention as well as methods for the production of reagents binding to said oligosaccharide sequences. The invention is also directed to the use of said oligosaccharide sequences and reagents binding to them for diagnostics of cancer and malignancies. Furthermore the invention is directed to the use of said oligosaccharide sequences and reagents binding to them for the treatment of tumors, cancers and malignancies.

BACKGROUND OF THE INVENTION

Various tumors express oligosaccharide sequences which are different from the non-malignant glycosylation of the same cell or tissue type. Examples of the known or speculated cancer associated oligosaccharide structures include: glycolipid structures such as globo-H (Fucα2Galβ3GalNAcβ3Galα4LacβCer), gangliosides: GM1 Galβ3GalNAcβ4(NeuNAcα3)LacβCer or GD2 GalNAcβ4(NeuNAcα8NeuNAcα3)LacβCer; Lewis-type fucosylated structures such as Lewis a and x: Galβ3/4(Fucα4/3) GlcNAc, Lewis y: Fucα2Galβ4(Fucα3)GlcNAc, sialyl-Lewis x: NeuNAcα3Galβ4(Fucα3)GlcNAc, and some combinations of these on polylactosamine chains; O-glycan core structures, such as T-antigen Galβ3GalNAcαSer/Thr-Protein, Tn-antigen GalNAcαSer/Thr-Protein or sialyl Tn-antigen NeuNAcα6GalNAcαSer/Thr-Protein. Presence of non-human structures such as N-glycolyl-neuraminic acid in cancers has also been indicated. Association and specificity of oligosaccharide structures with regard to cancers have been well established only in few cases, some of the structures are present in normal cells and tissues and are possibly only more concentrated in cancers.

One report has indicated that structures with terminal GlcNAcβ3GalβGlcNAc sequence are present in human leukemia cells (Hu et al., 1994). The structures may also be equally present on normal leukocytes. Thus, the relation of the finding to glycosylation patterns generally present in solid tumors was not indicated. This type of saccharide structures may be a part of rare normal glycosylations of human tissues: GlcNAcβ3Galβ4GlcNAcβ6sequence linked on O-glycans is probably present on human gastric mucin. A study shows that a monoclonal antibody recognizing GlcNAcβ3Galβ4GlcNAcβ6 sequence may possibly recognize similar structures on malignant tissues, such as mucinous ovarian neoplasms, pseudopyloric metaplasia of gallbladder and pancreatic epithelia, gastric differentiated carcinoma of stomach, gallbladder and pancreas, and on non-malignant tissues, such as human amniotic fluid, but, however, the structures from malignant tissues were not characterized (Hanisch et al., 1993). The antibody did not recognize neoglycolipid structure GlcNAcβ3Galβ4GlcNAcβ3Galβ4 nor carcinomas of lung, colorectum, endometrium or other organs. Another monoclonal antibody raised against testicular cells probably recognizes branched N-acetyllactosamines such as GlcNAcβ3(GlcNAcβ6)Galβ4GlcNAc- (Symington et al., 1984). Terminal GlcNAc has also been reported from mucins of human foetal mucin (Hounsell et al., 1989). In normal tissues terminal GlcNAc may be present in minor amounts as biosynthetic intermediates in the biosynthesis of poly-N-acetyllactosamines.

Several monoclonal antibodies has been raised against a semisynthetic glycolipid GlcNAcβ3Galβ4GlcNAcβ3LacβCer, these antibodies were shown to recognize glycolipids from cultured colon cancer cell lines and tumors (Holmes et al., 1991). However, the antibodies recognized several structures and the binding data was contradictory. Moreover the glycolipids were not recognized by all of the antibodies and the glycolipid structures from cancer cells or tumors were not characterized. Therefore the presence of terminal GlcNAc structures on tumors were not established. Another study showed production of a monoclonal antibody against GlcNAcβ3LacβCer (Nakamura et al., 1993). This antibody also weakly recognized the pentasaccharide structure described above. Moreover, the antibody recognized a protease sensitive epitope on COS-1 cells, which cell line is not of human origin. The immunization protocols of these studies did not describe induced antibody responses against polyvalent conjugates of the saccharides, but immunization by glycolipids.

Normally there are large amounts of antibodies recognizing terminal GlcNAc structures in human serum. There is also a class of natural antibodies recognizing terminal Galα3Galβ4GlcNAc- structures. The Galα antigen is not naturally present in man and recently it was also shown that the natural antibodies bind structures such as GalNAcα3Galβ4GlcNAc, GalNAcβ3Galβ4GlcNAc, and GlcNAcβ3Galβ4GlcNAc (Teneberg et al., 1996). The X2-structure, GalNAcβ3Galβ4GlcNAc, is a normal antigen on human tissues and structures GalNAcα3Galβ4GlcNAc and Galα3Galβ4GlcNAc have not been described from normal or cancer tissues. Thus, the present finding that the terminal GlcNAc structure is a tumor antigen indicates that the actual function of the natural antibodies might be the prevention of cancers having terminal GlcNAc structures.

The following patents describe cancer antigens and their use for making antibodies for therapeutic and diagnostic uses and for cancer vaccines. The antigen structures are not related to saccharides of the present invention:

Cancer vaccines: U.S. Pat. Nos. 5,102,663; 5,660,834; 5,747,048; 5,229,289 and 6,083,929.

Therapeutic antibodies: U.S. Pat. Nos. 4,851,511; 4,904,596; 5,874,060; 6,025,481 and 5,795,961.

Diagnostics: U.S. Pat. Nos. 4,725,557; 5,059,520; 5,171,667; 5,173,292; 6,090,789; 5,708,163; 5,679,769; 5,543,505; 5,902,725 and 6,203,999.

In the prior art tumor diagnostic and therapeutic antibodies recognizing chitobiose-mannose trisaccharides has been described in DE 38 07 594 A1. The application also describes other N-glycans with numerous varying terminal structures some of which may comprise also non-reducing terminal N-acetyl glucosamine. Several of the desired structures have been characterized as normal glycans and not cancer specific structures. The application claims to describe structures useful for cancer applications. However, it is not clear from the invention what the structure of the desired glycan is. Formel (I) may indicate presence of non-reducing terminal GlcNAc, if it is unconventionally read from right to left. However the Formel (I) does not indicate the linkage structure of the terminal GlcNAc. The Formel (III) indicates that the GlcNAc residues are α2, α4, or α6-linked. The present invention is not directed to such unusual structures. The present invention is directed to human tumor specific glycans comprising non-reducing end terminal β-linked GlcNAc residues.

Patent application WO 00/21552 claims several unusual O-glycan structures isolated from bovine submaxillary mucin. Two of the structures such as GlcNAcβ6GalNAcα6GalNAc and GalNAcβ3(GlcNAcβ6)GalNAc comprise terminal GlcNAc-residues. The application did not indicate that said structures would also be related to bovine or human cancers. The present invention is not directed to these structures comprising two GalNAc-residues. The application contains speculation about potential therapeutic use of the structures as antigens related to cancer. However, it has not been shown that the structures are related to bovine cancer when these are present in bovine normal submaxillary secretion. Moreover, it is even less probable that the structures would be present in human tissues, the glycosylations are species specific and vary between human and bovine, e.g. bovine and human glycosyltransferase and glycosylation profiles are different. The human genome is also known and thus gylcosyltransferases which could be related to synthesis of the claimed bovine structures should have been now produced and characterized from human. So far none of these has been described in human, or human cancer.

Meichenin et al, 2000 shows a murine monoclonal antibody which can bind to some oligosaccharides containing terminal GlcNAcβ and to certain human tissue cancer samples. The antibody was produced in mouse using the endo-beta-galactosidase treated red cells. However, the article does not establish any human specific immunotherapy with a specific antibody or other carbohydrate specific binding substance binding to an immunogenic carbohydrate. Moreover, the fact that such an antibody with limited specificity was formed in mouse does not indicate that similar antibody would be formed in human, or it would be tolerable in human, or be useful in context of individual human tumors of specific kind, since immune reactions to carbohydrates are species specific. Endo et al, 1996 describes N-glycan type oligosaccharides from soluble protein alkaline phosphatase of rat hepatoma AH-130 cell line. Again, material of animal origin is speculated in view of cancer specificity. Therefore, no diagnostics or therapy of human cancer is disclosed.

Patent application FI20011671 described the general usability of terminal GlcNAc-structures in tumor therapy. The application described specific polylactosamine type oligosaccharide sequences containing terminal GlcNAc linked to Gal especially found from glycolipid. The application indicated that the structures can be part of N-linked glycan or O-linked glycans, and that the tumorspecific oligosaccharide sequences can also be linked to O-glycosidic GalNAc. The application did not disclose exact structures of the O-linked or N-linked glycans.

The present invention describes preferred treatment of cancer when the oligosaccharide sequences have been detected from cancer but not from normal tissues. The present invention is directed to the combination of the analysis and treatment of a cancer. The present application also show for the first time the usability of the oligosaccharide sequences of the terminal beta-GlcNAc sequences for cancers of lung, stomach, colon, larynx and mucinous carcinomas, especially mucinous ovarian carcinomas, forming a group of epithelial type and/or mucin secreting cancers. The present invention is further especially directed to human cancer specific protein linked GlcNAcβ-structures. The present invention is also further especially directed to the specified N-glycans and O-glycans and protein linked GlcNAc. The preferred structures form a specific family of terminal specifically "protein linked GlcNAcβ-structures" which are human protein linked GlcNAc O-glycans and N-glycans form a specific family of human cancer specific "protein linked GlcNAcβ-glycan cores" which are result of defective galactosylation of cancer or tumor tissue.

The present application further describes human natural antibodies and more specifically human cancer associated antibodies specifically recognizing preferred human terminal beta-linked GlcNAc structures. The present invention also describes an enzyme based targeting of the cancer antigens by transferring a modified monosaccharide derivative on cancer cells. The presence of the human natural cancer associated antibodies shows that it is possible to use the structures as targets for cancer therapy in human in vivo. The invention is specifically further directed to antibody and other cancer targeting therapies and therapeutic immune reactions such as cancer vaccination and reagents useful for these directed to the preferred specifically protein linked GlcNAcβ-structures. The present invention is specifically further directed to antibody and other cancer targeting therapies and therapeutic immune reactions such as cancer vaccination and reagents useful for these directed to human cancer specific protein linked GlcNAcβ-glycan cores.

Current therapies for cancer and numerous infectious diseases are not effective enough. Cancers are major cause of deaths in industrialized countries and devastating infectious diseases kill children and adults especially in developing countries. Infections are probably behind numerous life-style and other diseases of the industrialized world, like gastric ulcers caused by *Helicobacter pylori*.

Previous in vitro studies have described the transfer of sialyl-Lewis x-oligosaccharides on surface of a cultured cell type. The cells were used to study the binding of human selectins to the sialyl- Lewis x oligosaccharides. Similarily, a blood group B-antigen has been transferred to human erythrocytes, and it was shown to be recognized by anti-blood group B antibodies. Because of the unnatural structure of the GDP-Fuc(-B-antigen), the authors stated that the structure was unsuitable for in vivo use. According to present invention, it is possible to use the unnatural structures as modified monosaccharides to target microbial pathogens, viruses, tumors or cancers.

A galactosyltransferase has been used to label human endo-beta-galactosidase modified erythrocytes (Viitala and Finne, 1984) and mouse teratocarcinoma cells (Spillmann and Finne, 1994) under in vitro conditions. Cell surface galactosyltransferases has been also studied in connection of various biological conditions. These studies do not describe diagnostics or therapy for any disease. The carbohydrates transferred are not monosaccharide conjugates according to the invention. The old studies utilized radioactively labeled UDP-Gal, the chemical structure of the Gal-residue is not changed but it contains atoms enriched with $^{14}C$ or $^{3}H$.

A fluorecently labelled muramic acid has been transferred on bacteria and the method was speculated to be used to study vaccination against the compound transferred or for interaction studies between bacteria, the transfer reaction was not specific for a type of a bacterium. The method was aimed to be used in vitro and the cells had to be permeabilized to achieve very weak reactions by the peptidoglycan precursor molecules (Sadamoto, R. et al 2001). In contrast the transfer reactions described by the present invention for bacteria are targeted to transfer of the carbohydrates directly to the cell surface. Preferentially the present invention is directed to in vivo use in the patient, which can be a human patient. Preferentially the invention is directed to use of transferring enzymes from the patients serum or transferring enzyme on the very surface of the pathogenic entity. As a separate embodiment the present invention is directed to direct cell surface vaccination against the pathogenic entity when a carbohydrate epitope is transferred.

Moreover the previous technology describes in vitro transfer of Gal on acceptors of a cancer cell by α1-3galactosyltransferase. The monosaccharide to be transferred is not modified nor aimed for blocking of a pathogenesis-inducing carbohydrate receptor. The invention does not describe transfer of immunologically active or toxic monosaccharide conjugates, but the terminal structure formed is reactive to anti Galα1-3Gal-antibodies. The epitope was aimed for increasing immununoreactivity of cancer cells to be injected as cancer vaccine.

Previous art also described transfer of 6-biotinylated Gal to GlcNAc-BSA or hen egg white ovalbumin or transfer of fluoresceinyl-NeuNAc to glycoproteins of golgi apparathus. The studies did not describe the therapy or diagnostics according to the invention (Bulter T. et al. 2001).

Various cell types express oligosaccharide sequences which are different from the non-malignant glycosylation of the same cell or tissue type. Association and specificity of oligosaccharide structures with regard to cancers have been well established only in few cases, some of the structures are present in normal cells and tissues and are possibly only more concentrated in cancers. The present patent application also describes terminal N-acetylglucosamine containing tumor specific oligosaccharide sequences. Priority of the recognition of the tumor specific oligosaccharide sequences by glycosyltransferases is claimed from the patent application.

Normally there are large amounts of antibodies recognizing terminal GlcNAc structures in human serum. Thus, the previous finding that the terminal GlcNAc structure is a tumor antigen indicates that the actual function of the natural antibodies might be the prevention of cancers having terminal GlcNAc structures.

SUMMARY OF THE INVENTION

The present invention describes oligosaccharide sequences, which are specifically expressed by human tumors. The present invention is related to a pharmaceutical composition comprising a substance binding to a human tumor specific oligosaccharide sequence containing a terminal beta-linked N-acetylglucosamine residue, GlcNAcβ, for the treatment of human cancer. The present invention is also related to a method of determining an oligosaccharide sequence, which comprises a human tumor specific terminal beta-linked N-acetylglucosamine residue, in a biological sample, the presence of said sequence in said sample being an indication of the presence of cancer. The present invention also provides antigenic substances comprising said oligosaccharide sequences in a polyvalent form and it further provides diagnostic agents, pharmaceutical compositions and cancer vaccines comprising said oligosaccharide sequences or substances binding to said oligosaccharide sequences. The present invention is also related to methods for the treatment of cancer.

DETAILED DESCRIPTION OF THE INVENTION

Figure 1:
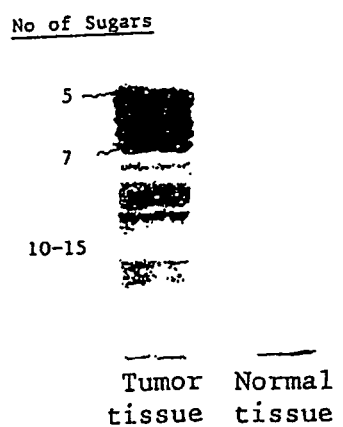
FIG. 1. An autoradiogram of a thin-layer assay after overlayering and binding of GlcNAcβ-specific E. coli bacterium demonstrating the tumor specificity of the oligosaccharide sequences containing terminal GlcNAc residue: non-acidic glycosphingolipids from hypemephroma tumor (first lane) and corresponding glycosphingolipid fraction from normal kidney (second lane).

The present invention is directed to terminal β-linked N-acetylglucosamine oligosaccharide chain structures and protein linked monosaccharide N-acetylglucosamine which are presented by human tumors. The present invention realizes specific defects in human tumors, which leads to cell surface and extracellular presentation of unsual carbohydrates comprising terminal N-acetylglucosamines. In general the terminal GlcNAc-structures are very rare in human normal tissues. The expression of the structures are caused by two factors. For the first the biosynthesis and degradation machinery in the tumor cells does not work properly. Many terminal structures in normal tissues comprise galactose on GlcNAc-residues, these structures are capped by sialic acids, blood group antigens and the like. The present data indicates that the cancer or tumor carbohydrates are exposed to unusual glycosidase activities and the defective glycosylation reactions by β4- and possibly also by β3-galactosyltransferases. Defects were observable in all 3 types of β-galactosylated oligosaccharide sequences. Secondly, the intracellular targeting and quality control of glycosylation including glycoprotein and glycolipid structures seem to be defective. In normal cells the glycosylation is under quality control which recirculates underglycosylated proteins and glycolipids to complete the natural glycosylation, so that in normal cells the amount of the structures disclosed in the invention are very rare on cell surfaces. In normal cells or tissues the oligosaccharide structures described by the invention are present in low amounts in human golgi apprathus, the known protein linked GlcNAc is considered to be almost exclusively a cytoplasmic nuclear protein modification. The defects in organization of the golgi apparathus leads to partial cell surface expression of the tumor specific structures described by the present invention. Even intracellularily overexpressed structures according to the present invention are directly useful for diagnostic applications.

The defects in galactosylation and presence of unusual glycosidase activities and loss of intracellular quality control lead to three types of tumor associated glycosylations:
1. incomplete, undergalactosylated protein linked N-glycan and incomplete, undergalactosylated
2. O-glycan core structures,
3. moreover polylactosamines are also undergalactosylated as exemplified by poly-N-acetyllactosamine type glycolipid from human hypemephroma.

These defects lead to several unusual terminal epitopes on glycoproteins. The present invention is directed to the three groups of oligosaccharide epitopes. The current invention notices for the first time similar general defect on all three types of glycan chains carrying normally β-galactosylated oligosaccharide sequences. Terminal β-linked GlcNAc is present as terminal structure. The structures indicate defects in enzymatic steps directly modifying the terminal GlcNAc-residues including β1,4(3)-Gal-transferase reactions and on the other hand increased glycosidase activities in the Golgi-pathway which could degrade terminal structures. However, the generality of the defect in 3 types of carbohydrates would indicate that organization of the golgi apparathus is so disturbed that terminally modifying enzymes located in late golgi cannot effectively modify all glycans expressed by tumor cells.

Furthermore present invention is directed to
4. missdirected expression of protein linked N-acetylglucosamine monosaccharide on cancers and tumors.

The protein linked N-acetylglucosamine is in general present in so called O-GlcNAc-structures intracellularily. The present invention notices strong overexpression of the protein linked N-acetylglucosamine. The overexpression leads to even some cell surface associated labeling of the O-linked GlcNAc on human tumors.

Though the terminal β-linked GlcNAc is common to the all three groups 1-3 above, it is realized that the subterminal structures have effect on the structures which should be recognized in diagnostic or theraphy of tumors or cancers. The present invention is specifically directed to therapheutic and diagnostic uses of terminal oligosaccharide sequences comprising the terminal GlcNAc and one to several neighboring monosaccharide residues in the three defective oligosaccharide sequence groups. The present invention is directed to the oligosaccharide sequences comprising nonreducing end terminal β-GlcNAc oligosaccharide sequences on polylactosamines, or O-glycans or N-glycans. The invention is directed to all of the defective glycosylation types when an analysis of normal glycosylation and potential general glycosylation defect is used together. The invention is further directed to the use of combinations of at least two of the four terminal GlcNAc type structures, especially the use of the polylactosamine type terminal GlcNAc-sequence in combination with the other terminal GlcNAc-structures as diagnostical targets.

General Galactosylation Defect and Specific Protein Galactosylation Defect

The present-invention discovered that the defect of the glycosylation may be general and affect at least two classes of the four defective classes of terminal GlcNAcβ-glycosylations disclosed in the invention: O-glycans, N-glycans, polylactosamines and protein linked GlcNAc. In a specific embodiment the general defect of galactosylation affects both specific protein linked glycosylations and glycolipid linked glycosylations, especially polylactosamine type terminal GlcNAc-structures of glycolipids. The present invention is specifically directed to detecting presence of general galactosylation defect from a cancer sample and/or from normal tissue sample of a person. The present invention is directed to the analysis of the general glycosylation defect producing the multiple types of terminal GlcNAc structures. The defect may be analyzed by an analysis of the carbohydrate samples as described by the invention. The galactosylation defect may be analyzed also by, for example, genetic or biochemical or cell biological means by analyzing production and/or activity and/or localization of enzymes or other proteins or biochemical mediators capable of producing the general glycosylation defect. The invention is directed to detecting general glycosylation defect when the intracellular structures involving glycan biosynthesis and/or degradation are defective. The present invention is especially directed to the analysis of the general glycosylation defect by genetic and/or biochemical and/or cell biological means when the method is verified with the analysis of carbohydrate structures, preferably the carbohydrate structures are analyzed by mass spectrometry and/or with known chemical and/or enzymatic methods and/or by substances according to the invention specifically binding and/or modifying the terminal GlcNAcβ-structures disclosed in the invention.

The analysis of the general glycosylation defect in cancer sample and/or normal tissues of patient is preferably used for selecting patients for treatment of cancer disclosed in the invention. The analysis of the general glycosylation defect in normal tissue(s) is according to the invention directed to be also used for predicting susceptibility or risk for a person for getting cancer and/or selecting persons for additional screening for cancer. The individual analysis of the normal tissue glycosylations and/or the general galactosylation defect disclosed in the invention is preferable as the normal glycosylation was noticed to vary in some cancer patients as described in the examples. In a preferred embodiment the invention is directed to the prediction of a high risk for cancer, especially for a person with "cancer type" terminal GlcNAc structures present in high amounts in normal tissue.

The present invention is especially directed to therapies targeting structures from at least two classes of defective glycosylations, i.e. terminal GlcNAcβ-glycosylations disclosed in the invention: O-glycans, N-glycans, polylactosamines and protein linked GlcNAc. In a preferred embodiment at least three classes or all four terminal GlcNAc-type structures are targeted. The invention is specifically directed to the targetting of the polylactosamine type structures together with the any other of the terminal GlcNAcβ-structures. In a preferred embodiment the polylactosamine type structures are targetted together with the protein specific N-glycan structures.

Specific Glycosylation Defect, Especially Protein Glycosylation Defect

The present invention further discloses a glycosylation defect wherein the intracellular structures involving glycan biosynthesis and/or degradation are defective. When a specific class of terminal GlcNAcβ-structures is defective, the specific glycosylation defect may be detected by analyzing alteration in activity and/or localization of specific enzymes synthesizing or degradating glycan structures to create terminal GlcNAc-structures. The present invention is especially directed to the analysis of the specific glycosylation defect by genetic and/or biochemical and/or cell biological means when the method is verified with the analysis of carbohydrate structures disclosed in the invention, preferably the carbohydrate structures are analyzed by mass spectrometry and/or with known chemical and/or enzymatic methods and/or by substances disclosed in the invention specifically binding and/or modifying the terminal GlcNAcβ-structures disclosed in the invention.

Tumor and Cancer Specific Defective Terminal Protein Linked GlcNAcβ-Structures

The present invention is especially directed to human cancer specific protein linked GlcNAcβ-structures. The data of the present application shows that protein fractions isolated from certain tumors express many terminal GlcNAc-structures on N-glycan and O-glycan type, especially "specifically protein linked GlcNAcβ-structures", which means that the GlcNAc-structures are present in core structures of N-glycans or O-glycans and not elongated as lactosamine structures. For example the experiment about the protein fraction from the same hypernephroma tumor previously shown to contain glycolipid linked GlcNAcβGal-structures, was now shown to express much of the specifically protein linked GlcNAcβ-structures such as N-glycan with terminal GlcNAcβ2Man-terminals. The present invention is thus especially directed to the specified N-glycans and O-glycans and protein linked GlcNAc structures as "specifically protein linked GlcNAc structures". The preferred structures form a specific family of terminal protein linked GlcNAcβ-structures which are human protein linked defective glycosylations present in human cancer. The present invention further disclose specific preferred N-glycan structures and O-glycan structures. The preferred terminal beta-GlcNAc O-glycans and N-glycans form a specific family of human cancer specific "protein linked GlcNAcβ-glycan cores" which are result of defective galactosylation of cancer or tumor tissue.

The present application further describes human natural antibodies and more specifically human cancer associated antibodies specifically recognizing preferred human terminal beta-linked GlcNAc structures. The application also describes an enzyme based targeting of the cancer antigens by transferring a modified monosaccharide derivative on cancer cells. The presence of the human natural cancer associated antibodies shows that it is possible to use the structures as targets for cancer therapy in human in vivo. The invention is specifically further directed to antibody and other cancer targeting therapies and therapeutic immune reactions such as cancer vaccination and reagents useful for these directed to the preferred specifically protein linked GlcNAcβ-structures. The present invention is specifically further directed to an antibody and other cancer targeting therapies and therapeutic immune reactions such as cancer vaccination and reagents useful for these directed to human cancer specific protein linked GlcNAcβ-glycan cores.

1. Incomplete, Undergalactosylated or Degraded N-linked Glycans.

The N-glycans described here belong to specifically protein linked GlcNAcβ-structures and protein linked GlcNAcβ-glycan cores disclosed in the invention. The structures include the natural N-glycans and terminal structure containing fragments thereof useful as for immunization or as a binding epitope for targeting substances. All structures contain specific GlcNAcβ2Man-structure.

The inventors have characterized by mass spectrometry several N-glycan structures comprising terminal GlcNAc residues from tumors such as larynx, stomach, colon and lung tumors. The present invention shows that the overexpression of the N-glycans on tumors is common. The novel N-glycan type tumor antigens were also detected specifically by novel glycosyltransferase methods from tissue sections of tumors but not or in lower amounts in corresponding normal or non-malignant tissues.

The present invention is directed to N-glycan structure GlcNAcβ2Manα3(GlcNAcβ2Manα6)Manβ4GlcNAcβ4 (Fucα6)GlcNAcβAsn and oligosaccharide substructures thereof carrying non-reducing end protein or peptide linked terminal GlcNAc. Asn indicates asparagine amino acids directly linked to the protein in the natural antigen. The natural protein linked oligosaccharide should contain the reducing end GlcNAcβAsn-structure and at least one of the branches carrying the terminal GlcNAcβ2Man. When the N-glycan structure is used for making antigenic epitopes, the present invention is directed to at least one of natural oligosaccharide sequence structures and structures truncated from the reducing end of the N-glycan according to the following Formula

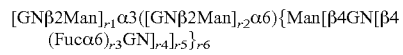

wherein
r1, r2, r3, r4, r5, and r6 are either 0 or 1,
with the proviso that at least r1 is 1 or r2 is 1.

GN is GlcNAc, with the proviso that when both r1 and r2 are 1, one GNβMan can be further elongated by one or several other monosaccharide residues such as galactose, and/or one GNβ2Man can be truncated to Man, and/or Manα6-residue and or Manα3 residues can be further substituted by GNβ6 or GNβ4, and/or Manβ4 can be further substituted by GNβ4.

The structures represent truncated forms of known N-linked glycan structures on human N-glycans. Such structures are rare on normal tissues and thus the structures are suitable for immunodiagnostics.

A group of more preferred structures are represented by formula:

[GNβ2Man]$_{r1}$α3([GNβ2Man]$_{r2}$α6){Man[β4GN]$_{r5}$}$_{r6}$ wherein
r1, r2, r5, and r6 are either 0 or 1,
with the proviso that at least r1 is 1 or r2 is 1.

GN is GlcNAc, with the proviso that when both r1 and r2 are 1, one GNβMan can be further elongated by one or several other monosaccharide residues such as galactose, and/or one GNβ2Man can be truncated to Man, and/or Manα6-residue and/or Manα3 residues can be further substituted by GNβ6 or GNβ4, and/or Manβ4 can be further substituted by GNβ4.

In a more preferred embodiment GN is GlcNAc, with the proviso that when both r1 and r2 are 1, one GNβMan can be further elongated by one or several other monosaccharide residues such as galactose, and/or one GNβ2Man can be truncated to Man, and/or Manα6-residue,
and most preferably GN is GlcNAc.

The preferred non-elongated structures include:
GlcNAcβ2Man, GlcNAcβ2Manα3(GlcNAcβ2Manα6)Man,
GlcNAcβ2Manα3 (GlcNAcβ2Manα6)Manβ4GlcNAc,
GlcNAcβ2Manα3(GlcNAcβ2Manα6) Manα4GlcNAcβ4GlcNAc,
GlcNAcβ2Manα3(GlcNAcβ2Manα6)Manβ4GlcNAcβ4 (Fucα6)GlcNAc,
GlcNAcβ2Manα3(Manα6)Man, GlcNAc(32Manα3 (Manα6)Manβ4GlcNAc,
GlcNAcβ2Manα3(Manα6)Manβ4GlcNAcβ4GlcNAc,
GlcNAcβ2Manα3 (Manβ6)Manβ4GlcNAcβ4(Fucα6) GlcNAc,
Manα3(GlcNAcβ2Manα6)Man, Manα3 (GlcNAcβ2Manα6)Manβ4GlcNAc,
Manα3(GlcNAcβ2Manα6)Manβ4GlcNAcβGlcNAc,
Manα3(GlcNAcβ2Manα6)Manβ4GlcNAcβ4(Fucα6) GlcNAc, GlcNAcβ2Manα3Man,
GlcNAcβ2Manα3Manβ4GlcNAc,
GlcNAcβ2Manα3Manα4GlcNAcβ4GlcNAc,
GlcNAcβ2Manα3Manβ4GlcNAcβ4(Fucα6)GlcNAc, GlcNAcβ2Manα6Man,
GlcNAcβ2Manα6Manβ4GlcNAc, GlcNAcβ2Manα6Manβ4GlcNAcβ4GlcNAc,
GlcNAcβ2Manα6Manβ4GlcNAcβ4(Fucα6)GlcNAc.

More preferred N-glycan oligosaccharide sequences include:
GlcNAcβ2Man, GlcNAcβ2Manα3(GlcNAcβ2Manα6)Man,
GlcNAcβ2Manα3(GlcNAcβ2Manα6)Manβ4GlcNAc, GlcNAcβ2Manα3(Manα6)Man,
GlcNAcβ2Manα3(Manα6)Manβ4GlcNAc, Manα3 (GlcNAcβ2Manα6)Man,
Manα3(GlcNAcβ2Manα6)Manβ4GlcNAc, GlcNAcβ2Manα3Man,
GlcNAcβ2Manα3Manβ4GlcNAc, GlcNAcβ2Manα6Man, GlcNAcβ2Manα6Manβ4GlcNAc.

And most preferred N-glycan oligosaccharide sequences include:
GlcNAcβ2Man, GlcNAcβ2Manα3(GlcNAcβ2Manα6)Man, GlcNAcβ2Manα3(GlcNAcβ2Manα6)Man4GlcNAc,
GlcNAcβ2Manα3(Manα6)Man,
GlcNAcβ2Manα3(Manα6)Manβ4GlcNAc, Manα3 (GlcNAcβ2Manα6)Man,
Manα3(GlcNAcβ2Manα6)Manβ4GlcNAc.

2. Incomplete, Undergalactosylated or Degraded O-linked Glycans.

The O-glycans described here belong to specifically protein linked GlcNAcβ-structures and protein linked GlcNAcβ-glycan cores disclosed in the invention. The structures include the natural O-glycans and terminal structure containing fragments thereof useful as for immunization or as a binding epitope for targeting substances. All structures contain specific GlcNAcβGalNAc, preferably GlcNAcβGalNAcα-structure.

The inventors have also found out that O-glycans of tumors contain structures carrying terminal β-linked GlcNAc. The O-glycan specificity for tumor is demonstrated in the examples by describing specific natural cancer associated antibody from a person recovered from ovarian cancer and by absence of the antibody in a pool of sera from persons without cancer background.

The present invention is specifically directed to human tumor specific O-glycan core structures comprising terminal β-inked GlcNAc residues, preferably with the provision that the O-glycan sequences do not comprise GalNAc-GalNAc sequence. The preferred O-glycan oligosaccharide sequences comprise at least one oligosaccharide sequence according to the formula:

[GlcNAcβ3]$_{s1}$[Galβ3]$_{s2}$(GlcNAcβ6)$_{s5}$GalNAc wherein s1, s2, and s5 are independently 0 or 1, with proviso that at least s1 is 1 or s5 is 1. When there is two GlcNAc structures, one may be substituted with Gal, NeuNAcαGal or other natural oligosaccharide sequences. The Gal-residue may be further substituted with sialic acid or other natural oligosaccharide sequences, in a preferred embodiment the Gal-residue is sialylated.

Preferred O-glycan oligosaccharide sequences include:
GlcNAcβ3Galβ3(Galβ4GlcNAcβ6)GalNAc,
GlcNAcβ3Galβ3(GlcNAcβ6)GalNAc,
GlcNAcβ3Galβ3GalNAc, Galβ3(GlcNAcβ6)GalNAc,
GlcNAcβ3(GlcNAcβ6)GalNAc, GlcNAcβ6GalNAc,
GlcNAcβ3GalNAc, and SAαGalβ3(GlcNAcβ6)GalNAc, wherein SA is sialic acid, preferably Neu5Ac or Neu5Gc or derivative such as O-acetylated derivative thereof which may be α3- or α6-linked to Gal.

More preferably O-glycan oligosaccharide sequences include:
GlcNAcβ3Galβ3GalNAc, Galβ3(GlcNAcβ6)GalNAc,
GlcNAcβ6GalNAc and GlcNAcβ3GalNAc and NeuNAcα-Galβ3(GlcNAcβ6)GalNAc.

Most preferred O-glycan sequences include Galβ3 (GlcNAcβ6)GalNAc, GlcNAcβ3GalNAc, GlcNAcβ6GalNAc and NeuNAcα3Galβ3(GlcNAcβ6)GalNAc.

The O-glycan means that the original antigen is protein/peptide linked from the reducing end to serine or threonine, preferably alpha linked to serine or threonine, or conjugate or analog thereof. The oligosaccharide may also be linked to other carrier aglycon or aglycon spacer structures. Linkage to aglycon or aglycon spacer means that the epitopes are not, at least not directly, linked to carbohydrate, especially not linked to GalNAcα. Aglycon preferably comprises at least one CH2-group like in serine or threonine, giving preferred structures OSα-O—CH$_2$—R, wherein OS is an oligosaccharide according to the invention and R is rest of the aglycon or spacer, preferably comprising additional methylene or acyclic alkyl-structures. In a separate embodiment the O-glycan is linked by a beta linkage as decribed above.

The present invention is specifically directed to human antibodies recognizing O-glycan oligosaccharide sequence structures Galβ3(GlcNAcβ6)GalNAc, and/or GlcNAcβ6GalNAc but not Galβ3(Galβ4GlcNAcβ6)Gal- NAc, and/or Galβ4GlcNAcβ6GalNAc and therapheutic and diagnostic uses of these as described by the present invention. In a preferred embodiment the present invention is directed to human antibody recognizing effectively oligosaccharide sequence Galβ3(GlcNAcβ6)GalNAc but not oligosaccharide sequence Galβ3(Galβ4GlcNAcβ6)GalNAc. GlcNAcβ3GalNAc is also preferred O-glycan type target for human antibodies. In preferred embodiment the human antibody is natural antibody. In another embodiment the antibody is induced by a cancer vaccine. In more preferred embodiments the human antibody is an IgG or IgA or IgM antibody, most preferably a IgG antibody.

As separate embodiment the present invention is directed to uses of to rare sialylated variants of the O-glycan core structures such as GlcNAcβ3(NeuNAcα6)GalNAc or NeuNAcα3Galβ3(GlcNAcβ6)GalNAc.

3. Poly-N-acetylactosamine Type Sequences Containing Terminal GlcNAcβ3 and/or GlcNAcβ6

The polylactosamine sequences described here do no belong to specifically protein linked GlcNAcβ-structures and protein linked GlcNAcβ-glycan cores according to the invention. The structures are useful in combination with the protein specific structures and other specific methods described by the invention.

The present invention describes the presence of terminal N-acetylglucosamine (GlcNAc) on poly-Nacetylactosamine type structures on human tumors. The structures were first found in large amounts from a human hyper nephroma tumor in one out of four tumors studied. The glycolipid fraction of the tumor was characterized to contain terminal N-acetylglucosamines by a specific radiolabelled *Escherichia coli* strain and FAB-mass spectrometry of permethylated sample. The glycolipid fraction also contained terminal N-acetyllactosamines, which could be detected by using a specific lectin. Screening of normal kidney glycolipids by the bacterium showed that the terminal GlcNAc was not present in the corresponding normal tissue, as it was not present in several other control tissues.

One embodiment of the present invention describes detection or isolation of an oligosaccharide sequence or oligosaccharide sequences comprising a terminal N-acetylglucosamine residue from tumor.

Following saccharide sequences are among the tumor specific structures to be isolated or detected: GlcNAcβ3Gal, GlcNAcβ3Galβ4GlcNAc, GlcNAcβ6Gal, GlcNAcβ3 (GlcNAcβ6)Gal, GlcNAcβ3(GlcNAcβ36)Galβ4GlcNAc, GlcNAcβ6Gal or GlcNAcβ6Galβ4GlcNAc, the sequences are part of poly-N-acetyllactosamine chains so that the chains comprise at least one terminal C-linked GlcNAc.

In a more preferred embodiment the present invention is directed to non-β6-containing linear polylactosamine sequences: GlcNAcβ3Gal, GlcNAcβ3Galβ4GlcNAc, GlcNAcβ3Galβ4GlcNAcβ3Galβ4GlcNAc.

In a separate embodiment the present invention is directed to β6-containing non-branched polylactosamine sequences: GlcNAcβ6Gal, GlcNAcβ6Galβ4GlcNAc, GlcNAcβ6Galβ4GlcNAcβ3Galβ4GlcNAc.

A preferred group of poly-N-acetylactosamine type sequences are β3-, β6-branched structures, GlcNAcβ3 (GlcNAcβ6)Gal, GlcNAcβ3(GlcNAcβ6)Galβ4GlcNAc, Galβ4GlcNAcβ3(GlcNAcβ6)Galβ4GlcNAc. Then branched structures resemble branched O-glycan structures.

Structures with type one N-acetyllactosamine, GlcNAcβ3Galβ3GlcNAc, or GlcNAcββ6Galβ3GlcNAc are also among the compounds within the scope of the invention.

4. Protein Linked N-acetylglucosamine

The protein linked GlcNAc described here belong to specifically protein linked GlcNAcβ-structures according to the invention. The inventors have characterized protein linked GlcNAc residues from tumors such as larynx, stomach, colon and lung tumors. The present invention shows that the over-expression of the protein linked GlcNAc expression on tumors is common. The novel N-glycan type tumor antigens were also detected specifically by novel glycosyltransferase methods from tissue sections of tumors but not or in lower amounts in corresponding normal or non-malignant tissues. The analysis of the protein linked GlcNAc indicated presence of several forms of protein linked GlcNAc In a specific embodiment the present invention is directed according to the present invention to therapheutic, and diagnostic uses, and pharmaceutical compositions, comprising beta linked N-acetylglucosamine monosaccharide residue, GlcNAcβ. Most of the tumors cells carry the O-glycan like GlcNAc releasable by β-elimination.

The present invention is in a preferred embodiment directed to the uses according to the present invention using O-glycosidic structures
GlcNAcSer and/or GlcNAcThr,
wherein the hydroxyl groups serine and threonine residues are glycosidically linked to the GlcNAc residue. The serine (Ser) and threonine (Thr) amino acid residues are in a preferred embodiments parts of peptides or peptide conjugates or derivatized from amino- and/or carboxylic acid groups.

In another preferred embodiment the present invention is directed to the uses of GlcNAcX, wherein X is aglycon preferably mimicking serine or threonine amino acid residues described above.

In a preferred embodiment GlcNAcβSer and/or GlcNAcβThr, GlcNAcβX is linked to polyvalent carrier according to the present invention for uses described by the invention, preferably to a carrier useful for vaccination, and most preferably to a carbohydrate carrier as described by the present invention.

In another preferred embodiment GlcNAcβSer and/or GlcNAcβThr, GlcNAcβX is linked to polyvalent carrier according to the present invention, preferably to a carrier useful for vaccination, and most preferably to a carbohydrate carrier as described by the present invention.

The present invention is also directed to β-linked N-glycosidic analogs of the O-glycan type structures described above, for example GlcNAcβ-Asn and peptide derivatives and analogs thereof. In biological samples such structures are formed by exoglycosidases or by endo-N-acetylglucosaminyltransferase.

Preferred Human Specific Immune Reactions

The present invention describes novel natural immune reactions found from persons having cancer or which have been cured from cancer. Possibility of human immune reaction against a novel carbohydrate cannot be guessed from animal data due to species specificity of glycosylation, The invention is especially directed novel human cancer associated immune reactions and human cancer associated antibodies including corresponding humanized antibodies against O-glycan structures GlcNAcβ3GalNAc, GlcNAcβ6(Galβ3) GalNAc, N-glycan structures comprising terminal GlcNAcβ2Man, especially ones binding GlcNAcβ2Manα3 (GlcNAcβ2Manα6)Man, and the protein linked GlcNAc-structure, especially when the antibody binds to GlcNAcβ-O—CH$_2$—R, where in the structure is O-glycosidically linked to serine or threonine or an aglycon represented by R as described for O-glycans. The antibody reactions were especially effective against O-glycan structures. Both IgM and IgG antibodies against all structures were observed. The invention is targeted both human IgG and IgM antibodies recognizing the preferred structures.

General Structures Representing Oligosaccharide Sequences

The oligosaccharide sequences of the invention can be a part of a glycolipid, a part of a glycoprotein, and/or a part of a N-acetyllactosamine chain. The tumor specific oligosaccharide sequences can also be a part of glycolipids, a part of N-linked glycans or O-linked glycans of glycoproteins. The tumor associated oligosaccharide sequences can also be directly linked to O-glycosidic GalNAc. Defects or changes in biosynthetic and/or biodegradative pathways of tumors lead to the synthesis of the oligosaccharide sequences of the invention both on glycolipids and glycoproteins. Terminal N-acetylglucosamine means that the non-reducing end GlcNAc residue in an oligosaccharide chain is not substituted by any other monosaccharide. The term oligosaccharide sequence indicates that the monosaccharide residue/residues in the sequence are part of a larger glycoconjugate, which contains other monosaccharide residues in a chain, which may be branched, or natural substituted modifications of oligosaccharide chains. The oligosaccharide chain is normally conjugated to a lipid anchor or to a protein. In a preferred embodiment the the oligosaccharide sequences according to the present invention are non-reducing terminal oligosaccharide sequences, which means here that the oligosaccharide sequences are not linked to other monosaccharide or oligosaccharide structures except optionally from the reducing end of the oligosaccharide sequence. The oligosaccharide sequence when present as conjugate is preferably conjugated from the reducing end of the oligosaccharide sequence, though other linkage positions which are tolerated by the antibody/binding substance binding can also be used. In a more specific embodiment the oligosaccharide sequence according to the present invention means the corresponding oligosaccharide residue which is not linked by natural glycosidic linkages to other monosaccharide or oligosaccharide structures. The oligosaccharide residue is preferably a free oligosaccharide or a conjugate or derivative from the reducing end of the oligosaccharide residue.

Minor species of ganglio- or galactosylglobosides can also represent the tumor specific terminal GlcNAc: terminal Galβ4GlcNAcβ3/β6 structures are linked to the glycolipid cores in some tissues and under low galactosylation conditions described by the invention terminal GlcNAcs can be revealed.

In another embodiment of the invention the tumor specific oligosaccharides are detected for the diagnostics of cancer or tumor.

Preferably the tumor specific oligosaccharide sequence is detected by a specific binding substance which can be an aptamer, lectin, peptide, or protein, such as an antibody, a fragment thereof or genetically engineered variants thereof. More preferably the specific binding substance is divalent, oligovalent or polyvalent. Most preferably the binding substance is a lectin or an antibody.

Specific binding combinatorial chemistry libraries can be used to search for the binding molecules. Saccharide binding proteins, antibodies or lectins can be engineered, for example, by phage display methods to produce specific binders for the structures of the invention. Labelled bacteria or cells or other polymeric surfaces containing molecules recognizing the structures can be used for the detection. Oligosaccharide sequences can also be released from cancer or tumor cells by endoglycosidase enzymes. Alternatively oligosaccharides can be released by protease enzymes, such as glycopepides. Chemical methods to release oligosaccharides or derivatives thereof include, e.g., otsonolysis of glycolipids and beta-elimination or hydrazinolysis methods to release oligosaccharides from glycoproteins. Alternatively the glycolipid fraction can be isolated. A substance specifically binding to the tumor specific oligosaccharide sequences can also be used for the analysis of the same sequences on cell surfaces. Said sequences can be detected, e.g., as glycoconjugates or as released and/or isolated oligosaccharide fractions. The possible methods for the analysis of said sequences in various forms also include NMR-spectroscopy, mass spectometry and glycosidase degradation methods. Preferably at least two analysis methods are used, especially when methods of limited specificity are used.

Analysis of Multiple Cancer Specific Structures Simultaneously from Mass Spectrometric Profiles The present invention is especially directed to the analysis and/or comparision of several analytical signals, preferably mass spectrometry signals produced from a sample comprising total fraction of oligosaccharides released from a cancer or a tumor sample. A single mass spectrum of an oligosaccharide fraction comprise a profile of glycosylation and multiple peaks indicating the potential presence of the oligosaccharide sequences and potential presence of cancer specific oligosaccharide sequences and altered levels thereof in comparison to normal tissue sample. The profiles are determined preferably by MALDI-TOF spectrometry as described in Examples. The total oligosaccharide fraction corresponds preferably total fraction of protein oligosaccharides, preferably comprising at least one cancer or tumor specific oligosaccharide sequence according to the invention. In another preferred embodiment the total oligosaccharide fraction comprises at least one cancer or tumor specific O-glycosidic and one N-glycosidic oligosaccharide according to the invention. The present invention is further directed to analysis of the multiple mass spectrometric signals when the total oligosaccharide fraction released from a cancer or tumor sample after an enzymatic or a chemical digestion step. The enzymatic digestion is preferably performed by a glycosidase enzyme, preferably selected from the group: galactosidase, sialidase, N-acetylhexosamidase, N-acetylglucosaminidase, fucosidase or mannosidase.

The present invention is also directed to the use of the tumor specific oligosaccharide sequences or analogs or derivatives thereof to produce polyclonal or monoclonal antibodies recognizing said structures using following process: 1) producing synthetically or biosynthetically a polyvalent conjugate of an oligosaccharide sequence of the invention or analogue or derivative thereof, the polyvalent conjugate being, for instance, according to the following structure: position C1 of the reducing end terminal of an oligosaccharide sequence (OS) comprising the tumor specific terminal sequence of the invention is linked (-L-) to an oligovalent or a polyvalent carrier (Z), via a spacer group (Y) and optionally via a monosaccharide or oligosaccharide residue (X), forming the following structure

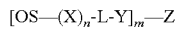

[OS—(X)$_n$-L-Y]$_m$—Z where integer m have values m>1 and n is independently 0 or 1; L can be oxygen, nitrogen, sulfur or a carbon atom; X is preferably lactosyl-, galactosyl-, poly-N-acetyl-lactosaminyl, or part of an O-glycan or an N-glycan oligosaccharide sequence, Y is a spacer group or a terminal conjugate such as a ceramide lipid moiety or a linkage to Z; 2) immunizing an animal or human with polyvalent conjugate together with an immune response activating substance. Preferably the oligosaccharide sequence is polyvalently conjugated to an immune response activating substance and the conjugate is used for immunization alone or together with an additional immune response activating substance. In a preferred embodiment the oligosaccharide conjugate is injected or administered mucosally to an antibody producing organism with an adjuvant molecule or adjuvant molecules. For antibody production the oligosaccharide or analogs or derivatives thereof can be polyvalently conjugated to a protein such as BSA, keyhole limpet hemocyanin, a lipopeptide, a peptide, a bacterial toxin, a part of peptidoglycan or immunoactive polysaccharide or to another antibody production activating molecule. The polyvalent conjugates can be injected to an animal with adjuvant molecules to induce antibodies by routine antibody production methods known in the art.

Antibody production or vaccination can also be achieved by analogs or derivatives of the tumor specific oligosaccharide sequences. Simple analogs of the N-acetyl-group containing oligosaccharide sequences include compounds with modified N-acetyl groups, for example, N-alkyls, such as N-propanyl.

Analogs that can be used for the production of antibodies binding GlcNAcβ3Galβ4GlcNAc include sequences Hex(NAc)$_{0-1}$α3Galβ4GlcNAc, Hex(NAc)$_{0-1}$β3Galβ4GlcNAc, where Hex is hexose, preferably Gal or Glc. The analogs may also comprise molecules where GlcNAc is replaced by a close isomer such as ManNAc.

According to the invention it is possible to use the tumor specific oligosaccharide sequences for the purification of antibodies from serum, preferably from human serum. Normally there are large amounts of antibodies recognizing terminal GlcNAc structures in human serum. There is also a class of natural antibodies recognizing terminal Galα3Galβ4GlcNAc structures. The Galα antigen is not naturally present in human and recently it was shown that the natural antibodies also bind in vitro structures GalNAcα3Galβ4GlcNAc, GalNAcβ3Galβ4GlcNAc, and GlcNAcβ3Galβ4GlcNAc (Teneberg et al., 1996). The X2-structure, GalNAcβ3Galβ4GlcNAc, is a normal antigen on human tissues and structures GalNAcα3Galβ4GlcNAc and Galα3Galβ4GlcNAc have not been described from human normal or cancer tissues. Thus, the present finding that the terminal GlcNAc-structure is a tumor antigen indicated that it is possible that the actual function of the natural antibodies is to prevent cancers and destroy tumors having terminal GlcNAc-structures. The tumor specific oligosaccharides or derivatives or analogs, such as a close isomer, can also be immobilized for the purification of antibodies from serum, preferably from human serum The present invention is directed to natural human antibodies which bind strongly to the tumor specific oligosaccharide sequences according to the present invention.

The tumor specific oligosaccharide sequences can also be used for detection and or quantitation of the human antibodies binding to the tumor specific oligosaccharide sequences, for example, in enzyme-linked immunosorbent assay (ELISA) or affinity chromatography type assay formats. The detection of human antibodies binding to the tumor specific oligosaccharide sequences is preferably aimed for diagnostics of cancer, development of cancer theraphies, especially cancer vaccines against the oligosaccharide sequences according to the present invention, and search for blood donors which have high amounts of the antibodies or one type of the antibody.

Furthermore, it is possible to use human antibodies or humanized antibodies against the tumor specific oligosaccharide sequences to reduce the growth of or to destroy a tumor or cancer. Human antibodies can also be tolerated analogs of natural human antibodies against the tumor specific oligosaccharide sequences; the analogs can be produced by recombinant gene technologies and/or by biotechnology and they may be fragments or optimized derivatives of human antibodies. Purified natural anti-tumor antibodies can be administered to a man without any expected side effect as such antibodies are transferred during regular blood transfusions. This is true under conditions that the tumor specific structures are not present on normal tissues or cells and do not vary between individuals as blood group antigens do, however, such blood-group-like variations are not known for the structures with terminal GlcNAc. In another embodiment of the invention species specific animal antibodies are used against a tumor or cancer of the specific animal. The production of specific humanized antibodies by gene engineering and biotechnology is also possible: the production of humanized antibodies has been described in U.S. Pat. Nos. 5,874,060 and 6,025,481, for example. The humanized antibodies are designed to mimic the sequences of human antibodies and therefore they are not rejected by immune system as animal antibodies are, if administered to a human patient. It is realized that the method to reduce the growth of or to destroy cancer applies both to solid tumors and to cancer cells in general. It is also realized that the purified natural human antibodies recognizing any human cancer specific antigen, preferably an oligosaccharide antigen, can be used to reduce the growth of or to destroy a tumor or cancer. In another embodiment species specific animal antibodies are used against a tumor or cancer of the specific animal.

According to the invention human antibodies or humanized antibodies against the tumor specific oligosaccharides, or other tolerated substances binding the tumor specific oligosaccharides, are useful to target toxic agents to tumor or to cancer cells. The toxic agent could be, for example, a cell killing chemotherapeutics medicine, such as doxorubicin (Arap et al., 1998), a toxin protein, or a radiochemistry reagent useful for tumor destruction. Such therapies have been demonstrated and patented in the art. The toxic agent may also cause apoptosis or regulate differentiation or potentiate defence reactions against the cancer cells or tumor. In another embodiment of the invention species specific animal antibodies are used against a tumor or cancer of the specific animal. The cancer or tumor binding antibodies according to the present invention can be also used for targeting prodrugs active against tumor or enzymes or other substances converting prodrugs to active toxic agents which can destroy or inhibit tumor or cancer, for example in so called ADEPT-approaches.

The therapheutic antibodies described above can be used in pharmaceutical compositions for the treatment or prevention of cancer or tumor. The method of treatment of the invention can also be used when patient is under immunosuppressive medication or he/she is suffering from immunodeficiency.

The terminal GlcNAc, or preferably GlcNAcβ3/6Galβ4GlcNAc-type cancer or tumor glycosylation, may be more common in tumors occurring in patients suffering from immunodeficient conditions, e.g., immunodeficiency causing diseases, such as AIDS, or immunodefiency caused by immunosuppressive medication. Kaposi's sarcoma is a common cancer related to AIDS and immunodeficiency. Immunosuppressive medications are used, for instance, with organ transplantations to prevent rejection during kidney, heart, liver or lung transplantations. Malignancies arising during such therapies are in general benign, but they cause often the loss of the precious organ transplant. Some of the potential natural anticancer antibodies may probably also recognize following epitopes: GalNAcβ3Galβ4GlcNAc, GalNAcα3Galβ4GlcNAc, and Galα3Galβ4GlcNAc, which have been shown to be similar. The first structure, $X_2$, is more common in persons who belong to a rare variant of p-blood group, these persons may also have less antibodies recognizing GlcNAcβ3Galβ4GlcNAc structure. Capability to produce antibodies against tumor or cancer specific antigens may vary according to individual differences in immune system. Persons who have recovered from cancer may have especially high amounts of natural anti-cancer antibodies.

A possible example from the antibody mediated immune reaction against tumor tissue is a total recovery from hypernephroma after surgery of the majority of the tumor. The oligosaccharide sequences with terminal GlcNAcs are potential targets of such immune response.

Other Methods for Theraphautic Targeting of Tumors

It is realized that numerous other agents beside antibodies, antibody fragments, humanized antibodies and the like can be used for theraphautic targeting cancer or tumors similarity with the diagnostic substances. It is specifically preferred to use non-immunogenic and tolerable substances to target cancer or tumor. The targeting substances binding to the cancer or tumor comprise also specific toxic or cytolytic or cell regulating agents which leads to destruction or inhibition of cancer or tumor. Preferably the non-antibody molecules used for cancer or tumor targeting theraphies comprise molecules specifically binding to the cancer or tumor specific oligosaccharide sequences according to the present invention are aptamers, lectins, genetically engineered lectins, enzymes recognizing the terminal GlcNAc-structures such as glycosidases and glycosyltransferase and genetically engineered variants thereof. Labelled bacteria, viruses or cells or other polymeric surfaces containing molecules recognizing the structures can be used for the cancer or tumor targeting theraphies: The cancer or tumor binding non-antibody substances according to the present invention can also be used for targeting prodrugs active against cancer or tumor to cancer or tumor or for targeting enzymes or other substances converting prodrugs to active toxic agents which can destroy or inhibit cancer or tumor.

Targetting Terminal GlcNAc-comprising Tumor Antigens by Glycosyltransferases

The present invention is also directed to novel method to transfer a modified monosaccharide derivative on cancer cells or tumor for treatment or diagnostics. We disclose a method of generating a covalent bond between a toxic agent, label, drug or immunologically active carbohydrate and the surface of a pathogenic cell of a patient, which surface comprises an acceptor structure recognized by a transferase enzyme, comprising the steps of
  conjugating said toxic agent, label, drug or immunologically active carbohydrate with a donor molecule of the transferase enzyme, and
  (a) administering the conjugate obtained and optionally said transferase enzyme to the patient for the treatment of tumor
  or (b), for tumor diagnostics, contacting the conjugate obtained to a tumor sample and detecting said label.

The monosaccharide derivatives to be transferred by glycosyltransferases also comprise a glycosidically linked nucleotide residue. The preferred monosaccharide derivatives are 2-modified such as amide derivatives of UDP-galactosamine A preferred theraphautic or diagnostic monosaccharide derivative is UDP-GalN[—S]-D, wherein
S is an optional spacer group
D is derivatizing group including molecular labels such as for example biotin or a fluorescent molecule including, or a toxic agent, prodrug or prodrug releasing substance as described for other cancer or tumor targetting methods.

The spacer is preferably flexible enough to allow the binding of the modified nucleotide monosaccharide to the transferase.

A preferred monosaccharide derivative is UDP-N-(6-biotinamidohexanoyl)galactosamine. A preferred enzyme to be used is a galactosyltransferase which is engineered to transfer effectively 2-modified monosaccharides. Also natural GalNAc/GlcNAc-transferases with similar specificity from animals for example, may also be used.

The present invention is especially directed to method to label tumor tissue by biotin by incubating the tissue with UDP-GalN-spacer-biotin and a modified galactosyltransferase.

The present invention is in a separate embodiment directed to a diagnostic method in which
  1. radiolabelled Gal is transferred from radiolabelled UDP-Gal to human tumor tissue by galactosyltransferase, preferably by β4-galactosyltransferase and
  2. the radioactivity incorporated to the tissue is used to determine amount of terminal GlcNAc residues on the tumor.

The methods using galactosyltransferases for labelling are effective for all types of terminal β-GlcNAc structures of the present invention.

Transfer of Modified Galactose Residue to Cancer for Therapy or Diagnosis of Terminal GlcNAcβ-structures The present invention is further directed to enzyme based therapeutic and diagnostic targeting and/or labeling terminal GlcNAc-residues in vivo or ex vivo by transferring a labeled monosaccharide covalently to the GlcNAc residues of material such as protein or tissue sample or cancer tissue expressing any cancer specific terminal GlcNAc containing structure, preferably any cancer or tumor specific structure according to the invention including the polylactosamine, N-glycan, O-glycan and protein linked terminal GlcNAc-structures. In a preferred embodiment polylactosamine, N-glycan, or O-glycan type of structure is targeted. The invention is specifically directed to glycosylation reactions of preferred terminal GlcNAc structures according to the invention. Preferably the monosaccharide is transferred by a β-glycosyltransferase, more preferably by β-glycosyltransferase which is β3- or β4-glycosyltransferase and most preferably by a β4-glycosyltransferase. In a preferred embodiment the transferase is able to transfer one or several of the monosaccharide residues selected from the group Glc, GlcNAc, Gal and GalNAc and at least one modified derivative thereof. Preferably the transferase is a Hex(NAc)$_r$β4-transferase, wherein Hex is Glc or Gal, and r is 0 or r is 1. Preferred glycosylatransferases include animal and human glycosyltransferase. Human transferases are especially preferred for in vivo uses.

The most preferred form of glycosylatransferase is an animal β4-GlcNAc and/or GalNAc-glycosyltransferase comprising structure allowing transfer of 2-modified Gal or GalN or Glc or GlcN. A preferred transferase has been described by Ramakrishnan and Qasba 2002. This bovine β4-galactosyltransferase enzyme has a mutation at a residue allowing the transfer. The present invention is also directed to similar animal enzymes containing the same or similar peptide structure at the catalytic site and having characterized to transfer GalNAc and/or GlcNAc from UDP-GalNAc or UDP-GlcNAc. In a preferred embodiment the animal enzyme is a variant of human β4-galactosyltransferase, preferably human β4-galactosyltransferase comprising the same mutation.

A preferred enzyme for transferring the substances is a glycosyltransferase capable of transferring of a monosaccharide unit modified to position 2. A mutated animal form of such enzyme was described by Ramakrishnan and Qasba 2002. The present invention is especially directed to soluble human glycosyltransferases and active fragments thereof, especially mutated galactosyltransferases, capable of transferring 2-modified monosaccharide structures.

Preferred 2-modified Carbohydrate Conjugates to be Transferred

The specific diagnostic method is directed to transfer of carbohydrate conjugate to terminal GlcNAc as described by the invention when the carbohydrate to be transferred is modified to position 2. The carbohydrate to be transferred has the structure according to the HexL-S-T                                    Formula C1

Wherein Hex is hexose preferably Gal or Glc,

L is linking atom on carbon 2 of the hexose preferably oxygen or nitrogen, or carbon or sulphur atom, more preferably L is oxygen or nitrogen, and most preferably nitrogen. S is spacer group or atom or nothing, preferably the spacer length is at least 3 atoms, more preferably at least four and most preferably at least 6 atoms. The spacer may be nothing if the T group includes a flexible aliphatic or equivalent chain such as polyalkylether-structure, preferably poly(ethylene glycol), PEG.

T is the group to be transferred or targeted according to the invention. The transferable group was surprisingly found out to be useful even when larger the acetyl group naturally present on GalNAc or GlcNAc, even larger than 4 carbon atom substance, even larger than 6-carbon substance or 10-carbon substance, the present invention is directed to transfer of substances comprising preferably more than 4 carbon atoms, more preferably more than 6 carbon atoms and most preferably more than 10 carbon atoms. According to invention the transferase accepts is also preferred for use in transfer of modified monosaccccharides containing more than about 100 Da extra molecular weight, even more than 500 Da, 1000 Da Or even more than 5000 Da. The present invention is directed to use of the full capacity of the preferred glycosyltransferases. The capability of the enzyme to transfer the large group allows the transfer of functional structures such as labels, therapeutic agents or non-immunogenic hydrophilic structures. The capability of transfer even PEG-polymer of about 5000 kDA was even more surprising than the transfer of biotin or similar size labels.

The invention is further directed to the nucleotide sugar conjugates for transferring specific substances T according to the invention according to the Nu-Hex(LS-T)                                Formula C2:

Wherein Hex, L, S and T are as above in Formula C1 and

Nu is a nucleotide activating the carbohydrate conjugate according to the invention. Preferred nucleotides includes UDP, GDP, TDP, and ADP depending on the preference of the glycosyltransferase used. Most preferably UDP is used. Preferred glycosylatransferases includes animal and human glycosyltransferase Preferred Nucleotide Sugar Conjugate Most preferred nucleotide sugar conjugates are according to the UDP-Gal(N-S-T)                              Formula C3 and

UDP-Glc(N-S-T),                             Formula C4 wherein the nucleotide is UDP and linking atom is nitrogen and S and T are spacer as described above.

Pretargetting Methods

Present invention is further directed to transfer linking groups by using modified monosaccharides according to the invention. The linking group can be later modified by a corresponding linking group linked with a group to be transferred according to the present invention. The present invention is especially directed to the transfer of chemoselective and protein/tissue compatible linking groups which are preferably effective in water solutions or aqueous buffers. The chemoselectivity means that linking group reacts to another corresponding linking group with selectivity. The protein and tissue compatibility means that the linking group or its corresponding linking group does not react, or does not essentially react with amino acid residues or other structures present on the material to be targeted under the conditions of the targeting reaction. The protein and tissue compatibility depends on the chemical groups present on the material. For example when protein to be targeted does not contain free cysteine side chain, thiol chemistry may be applicable. A preferred pair of chemoselective group is a thiol and a thiol reactive group such as for example maleimide. Another preferred pair of desired linking groups is a aldehyde or ketone to be reacted with an aminooxy group. The aminooxy group reacts selectively and effectively the carbonyl substances in aqueous solution.

The present invention is directed to substances according to the formulas C1-C3 when the T group to be targeted is a chemoselective and protein/tissue compatible linking group. The inventors found out that the preferred modified galactosyltransferase according to the invention transfers at least certain non-carbon atom comprising linking groups even when the spacer is short such as 2-4 four atoms. In a preferred embodiment the invention is directed to substances comprising a short spacer comprising at least 2 carbon, in preferred embodiment at least 3 or 4 atoms, atoms and a linking group, preferably when the spacer has 2 carbon atoms the linking group is N-protected aminooxy group. The aminooxy group is preferably transferred in protected form which is cleaved to reactive aminooxy group under conditions compatible with most proteins. In a specific embodiment a protected linking group according to the invention is used.

In another pretargeting method the invention is directed to transfer of biotin as a non-covalent pretargetting group. Additional groups can be targeted to biotin by avidin or strepavidin. The present invention is specifically directed to transfer of biotin on to tissue or cell as described by the invention, the examples represent useful methods and reagents and actual labelling. Methods to therapeutically target biotin or (strept) avidin pretargeted to cancer for example in vivo in human has been demonstrated. The methods have been effective in clinical trials. Therefore the transfer of biotin to cancer tissue according to invention is especially preferred.

Therapeutic Targeting of Carbohydrate Conjugate to Prevent Harmful Interactions/in vitro Modification of Therapy Related Agents In a preferred embodiment the present invention is directed to conjugates which contain a non-immunogenic hydrophilic structure linked to transferable carbohydrate. The non-immunogenic hydrophilic structure is preferably polyalkylglycol or equivalent or a carbohydrate, preferably a non-immunogenic polysaccharide, fragment of a polysaccharide or an oligosaccharide. Most preferably the non-immunogenic hydrophilic structure is a polyethyleneglycol (PEG). The aim of the substance is to target a therapeutic substance such as therapeutic protein or a cell or a tissue away from a source of harmful interaction. The modification occurs usually in vitro and the therapeutic substances including therapeutic proteins, cells and tissues are collectively called herein therapeutic agents. The modification of cells and tissues may aim for therapy such as transplantation, xenotransplantation or treatment of wounds or tissue damages. The harmful interaction may be mediated for example by receptor removing a therapeutic protein from blood circulation, by a proteolytic or hydrolytic enzyme degradating therapeutic protein or cell or tissue, by cells such as leukocytes degradating or binding to the or by the structures of kidney removing low molecular weight substances including low molecular weight proteins from blood circulation.

The pegylation is generally used for improving the quality of therapeutic proteins. Numerous proteins have been biotechnologically produced and modified by PEG, some of the proteins are in the markets. In most cases the pegylation increases the molecular weight of a low molecular weight protein normally cleared through kidneys. The present invention is aimed for substances and methods for pegylation of therapeutic protein. Pegylation of tissues or cells may be needed in medical operation such as xenotransplantation. In such case the pegylation is aimed for example for protection of the transplanted tissue from degradation by immune system. Such methods may be used for example in transplantations of neural tissue for treatment of Parkinsson's disease or transplant of pancreatic islet cells for treatment of diabetes.

Methods to Modify Substrates Containing Terminal GlcNAc Structures in vitro for Therapeutic Agents The present invention is aimed for modification of under galactosylated glycoproteins produced by certain cell line, for example by insect cells. The present invention is especially directed to modification of terminal GlcNAc containing proteins produced under conditions yielding undergalactosylated (and sialylated) glycoproteins. The lack of terminal glycosylation may be induced by cell culture conditions, such as amount oxygen, presence of monosaccharide substrates and proteins. The present invention is further directed to removal of the terminal glycosylation by expressing galactosidase or sialidase (neuraminidase) or fucosidase or N-acetylhexosminidase enzyme, preferably a beta-galactosidase and optionally alpha-neuraminidase to the cell culture medium by the same or different production cell line. The alpha neuraminidase may be of general broad specificity or specific for the sialic acid species produced with alpha3-, or alpha6- and optionally also for alpha8- or alpha 9-linked sialic acid. The glycidase enzyme may be produced as immobilized in the cell wall of yeast or other production cell type. The present invention is directed to modification of terminal GlcNAc on O-glycan or N-glycan and/or protein linked glycans. The substrate of the modification is usually part of regular N-glycosidic or O-glycosidic core structures. The present invention is specifically directed to substances according to Hex(L-S-PEG)-GlcNAcβ-Core-peptide  Formula P1:

wherein Hex, L and S are as described in Formula C1, Core is a core structure of N-glycan and/or O-glycan, when GlcNAc is part of the core structure the core is the glycan core excluding a terminal GlcNAc residue, PEG is polyethylene glycol, and peptide is protein or peptide to be targeted away from immune system or other harmful interactions. Preferably the peptide is a therapeutic protein known to have been pegylated before. Preferably the therapeutic protein is an antibody or a low molecular weight protein such as human erythropoietin (EPO), an interferon or an interleukin. In a prefferred embodiment the protein is avidin protein aimed for in vivo use.

More preferably the present invention is directed to substances according to the Gal(N-S-PEG)-GlcNAcβ-Core-peptide,  Formula P2:

wherein S, PEG-core and peptide are as described above.

In a preferred embodiment the present invention is preferably directed to substances according to the Glc(N-S-PEG)-GlcNAcβ-Core-peptide,  Formula P3:

wherein S, PEG-core and peptide are as described above.

The present invention is further directed to modified cell or tissue material, when the modification is produced by transfer of modified carbohydrate on the surface of the cell and/or tissue according to the invention. Preferred substances are according to the invention as follows.

Hex(L-S-PEG)-GlcNAcβ-Core-cell/tiss  Formula CT1 wherein Hex, PEG, L and S are as described in Formula D1, Core is a core structure of N-glycan and/or O-glycan, optionally excluding a terminal GlcNAc residue, Cell/tiss means cell or tissue modifiable.

More preferably the present invention is directed to tissues according to the

Gal(N-S-PEG)-GlcNAcβ-Cell/tiss,  Formula CT2:

wherein S, PEG-core and peptide are as described above.

In a preferred embodiment the present invention is preferably directed to substances according to the Glc(N-S-PEG)-GlcNAcβ-Cell/Tiss,  Formula CT3:

wherein S, PEG-core and peptide are as described above.

The present invention is further directed to modified cell or tissue material, when the modification is produced by a transfer of modified carbohydrate on the surface of the cell and/or tissue according to the invention.

The present invention describes therapeutic or diagnostic substances, which can be transferred in vivo covalently to a cell surface, especially to surfaces of a pathogenic entities such as cancer or tumor cell, bacterium, virus or parasite.

Furthermore the present invention describes the transfer of the therapeutic or diagnostic substances in vivo covalently to cell surfaces, especially to the surfaces of pathogenic entities such as 1) cancer or tumor cells, 2) microbial pathogens including bacteria, fingi, viruses and parasites, and 3) pathogenesis or metastasis-inducing receptors. The present invention especially relates to the transfer of donor carbohydrate to oligosaccharides related to pathogenic conditions, like cancer specific oligosaccharide sequences, or to those present on pathogens like viruses, bacteria or parasites. The invention is especially directed to the use of carbohydrate conjugated to immunologically active or toxic therapeutic substances for the treataent diseases like infections, cancers and malignancies.

The invention can be also used to target drugs to cell or tissue surfaces, where these can be recycled inside of cells. In a specific embodiment the drug is conjugated to the carbohydrate to be transferred by a labile bond, which is cleaved inside the cells and the drug is released.

In another specific embodiment, the therapeutic substance is a natural type of monosaccharide, which is covalently transferred to a pathogenesis-inducing carbohydrate receptor in vivo and blocks the pathogenesis-inducing carbohydrate receptor. The pathogenesis-inducing carbohydrate receptor may be a carbohydrate receptor of a metastasizing cancer, pathogenic microbe, or a defective glycosylation of tissue causing autoimmune type disorders.

Moreover, the invention describes search of tissue or pathogenesis specific receptors by covalent in vivo transfer of substances to surfaces of cells or tissues. The present invention describes methods for the in vivo detection of the pathogenic entities and pathogenesis-related receptors. The in vivo transfer to tissues is useful for tissue imagining technologies even when the transfer target is not related to pathogenesis. The invention is also directed to the use of carbohydrate conjugates for diagnostics of the pathogenic entities and diseases related to them. The invention is specifically directed to the use of said carbohydrate/carbohydrates for diagnostics of infections, cancer and malignancies.

The in vivo Transfer to Cell Surfaces

The present invention describes the covalent in vivo transfer of a therapeutic or diagnostic molecule to cell surfaces. The transfer is performed by a transferring enzyme, which can transfer a donor substrate molecule to a cell surface or more specifically to an acceptor substrate molecule which is preferentially a cell surface molecule, but can also be a cell surface associated molecule. The donor substrate molecule can be used to block a pathogenesis-associated receptor by in viva synthesis of a tolerated natural structure from the pathogenesis-associated receptor on a cell surface. In another embodiment the donor substrate is a transferable molecule conjugated to a therapeutic or a diagnostic molecule. The conjugation is performed so that it allows the donor substrate conjugate to be recognized and transferred by the transferring enzyme.

For example, the transferring enzyme can be a glycosyltransferase, the donor substrate molecule can be a nucleotide sugar or a lipid donor of a glycosyltransferase enzyme and the acceptor substrate a cell surface carbohydrate or a cell surface associated carbohydrate. Moreover, as an another example, the transferring enzyme can be a transglycosylating enzyme, the donor substrate is an oligosaccharide or a glycoconjugate donor for the transglycosylating enzyme, and the acceptor substrate is a cell surface carbohydrate acceptor of the transglycosylating enzyme. Preferentially a monosaccharide residue or conjugate thereof is transferred from a donor to an acceptor substrate. Transglycosylating enzymes and even glycosyltransferases like oligosaccharyltransferase can also transfer oligosaccharides. In both cases the first substrate can be conjugated to a therapheutic or a diagnostic molecule.

The invention can be also used to target drugs to cell or tissue surfaces, where these can be recycled inside of cells. In a specific embodiment the drug is conjugated to the modified monosaccharide by a labile bond, which is cleaved inside or on the cells and the drug is released.

Special Requirement of in vivo Transferring Reactions

The invention is directed to reaction conditions and reagent combinations, which allow glycosyltransfer reactions to achieve transfer of therapeutic or diagnostic carbohydrates to desired targets under novel in vivo conditions.

A. Glycosyltransferase Reactions in vivo

Transferase reactions. The invention is directed to use of natural glycosyltransferases present in human and mammalian body fluids and cell surfaces. The functions of extracellular glycosyltransferases are largely unknown, the cell surface forms may be cell adhesion molecules. It is realized in the present invention that the specificities of the glycosyltransferases present in sera allows specific transfer reactions to special precursor oligosaccharides present on pathogenic entities.

Furthermore, it is realized that this method could be used for special targeting of therapheutic or diagnostic compounds to surfaces of pathogenic entities, like cancer cells or microbial pathogens. This targeting method differs from previous ones in that the carbohydrate conjugates are transferred covalently to the surface of a pathogenic entity. It is realized that certain cancers for example carry terminal GlcNAcβ- and GalNAcα-containing acceptors for βgalactosyltransferases of human serum.

It is further realized that the reactions can be used to transfer toxic or diagnostic agents on surfaces of microbes like *Neisseria* or parasites like *Trypanosoma cruxii*, which are known to transfer sialic acid to their surfaces. The modern recombinant enzyme technologies also allow use of additional glycosyltransferases in body of a patient, for such application the transferase should be preferentially well tolerated like recombinant forms of soluble human transferases. Even glycosyltransferases from microbial pathogens could be useful for specific transfer to surfaces of microbes, but immune reactions against the pathogen type transferases may limit usefulness of long term therapies or change the effect of theraphy to more vaccination like in a longer time scale.

In an separate embodiment the pathogenesis inducing receptor is a tissue saccharide structure of a patient ant the structure is receptor for cancer, microbial pathogen or a toxin secreted by a microbial pathogen or an autoimmune receptor like under glycosylated structures in certain glycosylation disorders. The terminal GlcNAcβ3LacNAc- and GalNAcβ3LacNAc-structures are potential receptor for the diarrhea causing toxin A from *Clostridiumn difficile*, these receptors can be blocked by tranasfer of Galβ4- of NeuNAcα3—to the receptors. Under-sialylation of LDL in atherosclerosis or under-galactosylation of erythrocytes in forms of HEMPAS or in IgG in diabetes are examples of conditions which are treatable in vivo according to invention by transfer of normal monosaccharides from regular nucleotide sugars. Cancers can metastasize to liver by terminal Gal-residues which bind to asialoglycoprotein receptor of liver, blocking the receptor by NeuNAcα3- reduces the liver metastasis in such cancer.

Special in vivo Transferase Reaction Conditions

The in vitro glycosyltransferase reactions are in general carried out in precence of relatively large amounts of $MnCl_2$, the $Mn^{2+}$-ion activates most of the known glycosyltransferases. The reagent may be also used to stabilize the donor nucleotide for improving the reaction conditions. Unfortunately, the $Mn^{2+}$-ion is neurotoxic and it is therefore preferred only in for short term use under following conditions: The carbohydrate or the conjugate to be transferred with $Mn^{2+}$-ion is used in limited amounts in 1) gastrointestinal tract 2) in urinary bladder 3) as directly administerd close to the pathogenic entity. The limited amounts means that therapy with $Mn^{2+}$-ion levels will not be reach toxic levels. Furthermore the amount of the toxic free $Mn^{2+}$-levels can be controlled by increasing molecules chelating the ion, for example a tolerated chelator used in serum for imagining with with $Mn^{2+}$-ion complex and/or adding chelating protein like transferring. The chelating agent can be used to remove extra $Mn^{2+}$-ions after the desired transfer has been achieved or locally in blood circulation after the cancer or pathogen position where the carbohydrate is targeted. For blood cells or blood components or tissue transplants glycosyltransferase reactions could be performed outside of the body even in presence of $Mn^{2+}$ if harmful amounts of the ions are removed before applying the blood or its components or tissue to the body of the patient, however use more tolerated divalent cations as described below is preferred It is further realized that use of the alternative less toxic divalent cations or removal of $Mn^{2+}$ is also preferred in production of glycosylation remodelled therapeutic glycoproteins.

Special Conditions for Galactosyltransferase/Modified β4-galactosyltransferase Reaction in vivo to React with Terminal GlcNAcβ-structures The galactosyltransferase activity of human serum was observed to require Mn2+ ions for activity, other cations did not essentially activate the transferase under assay conditions. It was then tried to add exogenous galactosyltransferase from bovine milk to serum and we found out that the enzyme was active even without manganese ions. Additional activation was achieved by divalent cations zinc, calsium and magnesium. The invention is especially directed to use added β4-galactosyltransferase in human blood circulation. It is preferred to use Zn2+, Ca2+ and/or Mg2+ ions for additional activation of the enzyme. It was further found out that phosphorylcholine has stabilizing effect to the donor substrate preventing part of degradation to galactose. The invention is further directed to use of a tolerable phosphoester substance, preferably phosphorylcholine to reduce the degradation of the donor in human blood. The manganese ion was observed to activate endogenous human galactosyltransferase at 1 mM concentration and even at 0.2 mM concentration. Under conditions where use of manganese is acceptable according to the invention, the invention is directed to use of about 0.01 mM to 1 mM $Mn^{2+}$, more preferably 0.02-0.2 mM $Mn^2$.

The invention also finds useful novel reaction conditions wherein no divalent cation is used for with $Mn^{2+}$-activable enzyme. This possible in vivo because the highly metabolically active cancer cells, or many stressed cells for example excrete glycosyltransferases and divalent cations complexed with these, the cell surface ion concentrations will allow reactions which are not possible in sole serum. More over the $Mn^{2+}$-ion or other divalent cations can be used together with exogenous glycosyltransferase and the donor carbohydrate as complex so that the free ion concentration remains lower.

It is more preferred to use tolerated alternative ions even though the enzyme activity is lower. According to the invention it is possible to use 4 mM $MgCl_2$ to activate fucosyltransferases in human whole blood. Short term therapies even bigger $Mg^{2+}$-ion- concentrations to about 6-8 mM could be tolerated by human patients. Additional use of high $Ca^{2+}$ concentration like about 1-2 mM gives occasionally better reactivity. In severe diseases like cancer or very lethal infections it may adviseable to try to increase the cation concentrations despite higher risks. When no divalent cation is used in rection with human whole blood more specific facosyltransfrase reaction is observed. It is possible to use the cations to regulated specificities of the transfer reactions in vivo. In a specific embodiment organic cation containing molecules like spermine or lechitin or choline can be used to increase the reactivity of the transferase. In some cases other divalent cations like $Co^{2+}$ or $Ba^{2+}$ or even $Cd^{2+}$ ion could be used for activation of specific glycosytransferases.

The invention also describes use of in vivo tolerable phosphatase inhibitors to increase the reaction. For example in gastrointertinal tract ATP can be used in millimolar concentrations. It must be noted that in gastrointestinal system it is useful to protect the carbohydrate and enzyme if used from the gastric acid.

Transfer of a Carbohydrate Conjugated to an Immunologically Active and/or a Toxic Carbohydrate In a preferred embodiment the carbohydrate is conjugated to an immunologically active and/or toxic, and the conjugate can be transferred to the surface of a pathogenic entity. The modified carbohydrates can be transferred to acceptors especially related to pathogenic conditions, like cancer specific oligosaccharide sequences or oligosaccharides present on pathogens like viruses, bacteria or parasites. The invention is especially directed to the use of modified monosaccharides for the treatment of diseases like infections, cancers and malignancies.

The modified monosaccharide is specifically targeted to the surface of the pathogenic entity by a glycosyltransfer reaction or reactions. The glycosyltransfer reaction is catalyzed by an enzyme, preferentially a transglycosylating enzyme or a glycosyltransferase enzyme, which recognize an acceptor oligosaccharide present on the surface of the pathogenic entity. The transglycosylating enzyme or glycosyltransferase enzyme is preferentially present in the patient, more preferentially the transferase is present in serum (and/or other fluids) of the patient. The transglycosylating enzyme or glycosyltransferase enzyme is preferentially present in a high concentration close to the pathogenic entity, like enzymes effectively secreted or effectively produced as membrane proteins by the pathogenic entity. In a specific embodiment glycosyltransferase or transglycosylating enzyme is used together with the modified monosaccharide. The enzyme may be added to increase the transfer of the modified monosaccharide. When the added glycosyltransferring enzyme is used in vivo it is preferentially in soluble form and not antigenic. Preferred glycosyltransferring enzyme include natural serum, urine and other soluble forms of glycosyltransferases of the patient.

In a preferred embodiment the transglycosylating enzyme is a transsialidase enzyme. The glycosyltransferase enzyme is preferentially galactosyltransferase, N-acetylglucosaminyltransferase, N-acetylgalactosaminyltransfrase, fucosyltransferase, sialyltransferase, mannosyltransferase, xylosyltransferase, glucuronyltransferase or glucosyltransferase. More preferentially the glycosyltransferase enzyme is β4galactosyltransferase, β3galactosyltransferase, β3-N-acetylglucosaminyltransferase, β2-N-acetylglucosaminyltransferase, β6-N-acetylglucosaminyltransferase, α3sialyltransferase, α6sialyltransferase, α3facosyltransferase, α2fucosyltransferase or α6fucosyltransferase. In a specific embodiment the transglycosylating enzyme or glycosyltransferase enzyme transfers a monosaccharide specific for the pathogenic entity like rhamnose, KDO, heptose or furanose monosaccharide residues present on bacteria. Many parasites can also transfer monosaccharides, which are normally not present in human body.

The modified monosaccharides to be used with glycosyltransferases are preferentially nucleotide sugar derivatives or analogs thereof, also other modified glycosides may be transferred by glycosyltransferases. For transglycosylation the modified monosaccharide may be a glycosides like phenyl- or paranitrophenyl-glycoside. The glycosyltransferases are known to tolerate numerous modifications on the donor substrates. Preferentially the nucleotide sugar derivative or analog is derivative of UDP-Gal or UDP-GalNAc where the toxic substance or immunologically active carbohydrate is linked to carbon number 2 or carbon number 6 of the Gal or GalNAc residue or a derivative or analog of UDP-GlcNAc or UDP-Glc where the toxic substance or immunologically active carbohydrate is linked to carbon number 2 or 6 of the Glc or GlcNAc residue or a derivative or analog of GDP-Fuc where the toxic substance or immunologically active carbohydrate is linked to carbon number 6 of the fucose residue or, an analog or a derivative of CMP-NeuNAc or CMP-sialic acid where the toxic substance or immunologically active carbohydrate is linked to carbon number 5, 7, 8, and/or 9 of the NeuNAc or sialic acid residue. Conjugates of NeuNAc and general methods of making nucleotide sugar conjugates have been further described in WO03031464A2.

The specificity of the transfer reactions is based on the specificity of the glycosyltranstransferring enzymes. The transfer is usually specific for both donor and acceptor substrates. For example specific types of galactosyltransferases or β1-3N-acetylglucosaminyltransfeases are known which can quite specifically transfer to certain O-glycan, N-glycan or polylactosamine structures. Use of soluble patient type glycosyltransferase, which is specific or quite specific for the carbohydrates acceptors present on the pathogenic entity, together with a modified nucleotide sugar is preferred. The patient type transfrase means the natural enzyme present in the patient, for example human glycosyltransferases for human use can be produced by biotechnology or less preferentially purified from human serum or tissues. More preferentially the transferase is used in the form naturally present in the part of the tissue where the therapy is used, like soluble serum form of the enzymes in serum The specificity of the transfer is also created by specific presence of the acceptor structure for the glycosyltransferring enzyme like a carbohydrate, glycoconjugate, peptide, protein or lipid on the pathogenic entity and/or the localization of transferring enzyme or the carbohydrate to be transferred close to the pathogenic entity. The specificity against the pathogenic entity can be also created by local activation of the toxic or immunologically active carbohydrate after the transfer reaction, for example radioactive substance may be locally activated by specific radiation.

The modified monosaccharides to be used with glycosyltransferases are preferentially nucleotide sugar derivatives or analogs thereof, also other modified glycosides may be transferred by glycosyltransferases. For transglycosylation the modified monosaccharide may be a glycosides like phenyl- or paranitrophenyl-glycoside. The glycosyltransferases are known to tolerate numerous modifications on the donor substrates. Preferentially the nucleotide sugar derivative or analog is derivative of UDP-Gal or UDP-GalNAc where the toxic substance or immunologically active carbohydrate is linked to carbon number 2 or carbon number 6 of the Gal or GalNAc residue or a derivative or analog of UDP-GlcNAc or UDP-Glc where the toxic substance or immunologically active carbohydrate is linked to carbon number 2 or 6 of the Glc or GlcNAc residue or or a derivative or analog of GDP-Fuc where the toxic substance or immunologically active carbohydrate is linked to carbon number 6 of the fucose residue or, an analog or a derivative of CMP-NeuNAc or CMP-sialic acid where the toxic substance or immunologically active carbohydrate is linked to carbon number 5, 7, 8, and/or 9 of the NeuNAc or sialic acid residue.

The specificity of the transfer is preferentially created by specific presence of the acceptor structure for the glycosyltransferring enzyme like a carbohydrate, glycoconjugate, peptide, protein or lipid on the pathogenic entity and/or the localization of transferring enzyme or the carbohydrate to be transferred close to the pathogenic entity. The specificity against the pathogenic entity can be also created by local activation of the toxic or immunologically active carbohydrate after the transfer reaction, for example radioactive substance may be locally activated by specific radiation. The specificity of the transfer reactions is based on the specificity of the glycosyltranstransferring enzymes. For example specific types of galactosyltransferases or β1-3N-acetylglucosaminyltransfeases are known which can quite specifically transfer to certain O-glycan, N-glycan or polylactosamine structures. Use of soluble patient type glycosyltransferase, which is specific or quite specific for the carbohydrates acceptors present on the pathogenic entity, together with a modified nucleotide sugar is preferred.

Transfer of Toxic Agents

The modified monosaccharide may comprise a toxic agent like a toxin, for example a bacterial toxin, a cell killing chemotherapeutics medicine, such as doxorubicin (Arap et al., 1998), or a radiochemical reagent useful for tumor destruction. Such therapies have been demonstrated and patented in the art. The toxic agent may also cause apoptosis or regulate differentiation. The modified monosaccharide can be linked to an additional immunologically active carbohydrate according to the invention, such as A or B blood group antigen not present in the patient, Galα3Gal-structure, ligand of other anti-carbohydrate antibodies, including anti-carbohydrate antibodies in patient, or ligand of the defensive lectins of the immune system.

Transfer of an Immunologically Active Carbohydrate

The immunologically active carbohydrate can be an oligosaccharide sequence recognized by natural human antibodies. Numerous such antibodies have been described. The antibodies recognize structures like terminal N-acetylglucosamine, N-acetyimannosamine, blood group antigens, or Galα3Gal-structures. The functions of the antibodies are not known and these may be caused by infections by bacteria carrying such oligosaccharide sequences. ABO-blood group antibodies restrict blood transfusion and organ transplantations, the antibodies recognize cells from transplant or transfusion and cause its rejection. Similarily anti-Galα3Gal-antibodies prevent xenotransplantation for example from pig to human.

The previous invention showed that the terminal N-acetylglucosamine sequence is present in human tumors, indicating potential anticancer reactivity of the natural antibodies. As monovalent compounds the oligosaccharide sequences are not harmful. When the oligosaccharides or carbohydrates, which are recognized by natural antibodies, are transferred in polyvalent form on a cancer cell/tissue surface, these are targeted by the natural antibodies, which leads to the destruction of the cancer cells or tumor. The terminal GlcNAc-structures and Galα3Gal-structures are generally applicable as such antibodies occur generally. Blood group antigens can be transferred to pathogenenic agents in patients, who have antibodies the specific blood group antigen. For example patients who have blood O usually have antibodies against blood group A and B-antigens, patients who have blood group A usually have antibodies against B-blood group antigens and patients who have blood group B usually have antibodies against A-blood group antigens. Several other blood group antigen systems like P-blood groups are known and could be used according to the invention. The antigenic structures, which are transferred on a pathogenic entity like cancer cells or microbial pathogens like bacteria or viruses or parasite are recognized by antibodies and cause destruction of the pathogen.

Beside the natural anti-carbohydrate antibodies special antibodies can be induced against carbohydrate structures in human. Patients or potential future patients can be and are vaccinated against carbohydrate epitopes of various pathogenic bacteria or parasites. Specific methods to induce immunity against cancer by cancer vaccines are also known. Preferentially the vaccine target carbohydrate structure is not exactly the same as the patient's own, non-cancer associated, carbohydrate structures to avoid autoimmune complications. The transfer of a vaccine carbohydrate epitope on a pathogenic entity as a immunologically active and/or toxic carbohydrate diverts the existing immune response against the vaccine epitope or immune response which is induced later by vaccination towards the pathogenic agent. The method can be also used as a vaccination method and immune response may necessarily not be needed to be separately induced by vaccination. When the immunologically active and/or toxic carbohydrate causes the destruction of the pathogenic entity, the immune responses against other components on the pathogenic entity are also induced and cause a vaccination effect. The transfer method is also useful to increase the effect of traditional vaccinations, the immunologically carbohydrate may be the same or different from the one used in the vaccination. The methods according to the present invention can be further used ex vivo/in vitro to modify cells such as red cell with specific antigenic structures. In a preferred embodiment the modified red cells are introduced back to the patient to induce an immune reaction against the antigen. The methods according to the invention can be further used ex vivo/in vitro to modify cells or other type of sample from human cancer with immune response inducing or antigenic carbohydrate conjugate to enhance immune reaction against cancer. The invention is further directed to the use of the transfer of modified carbohydrate with covalently conjugated structure to produce a cell based cancer vaccine from human cancer cells or red cells. The present invention is further directed to ex vivo/in vitro modifications of cells with carbohydrate antigens/or structures. These are likely to be effective immunoconjugates.

In the most general form of invention it is possibly to transfer any substance recognized by immune system to the surface of the pathogenic entity. Beside carbohydrates such substances include protein or peptide antigens like protein or peptide vaccine substances, non-harmful parts of peptidoglycan or lipid A of bacteria which can be transferred to cell surface of a pathogenic entities. Moreover specific component of immune system like complement proteins could be transferred. Conjugates of protein substances could create autoimmune problems, which should be considered when planning conjugation chemistry. Inducing immune responses against conjugates of non-natural epitopes like para-nitrophenyl is also known and can be used according to the invention. The non-natural epitope can be transferred on the pathogenic entity alone or in combination with a vaccination type therapy against the non-natural epitope. Use of non-natural epitopes may reduce risks of autoimmune reactions when the targeting technology is good enough. The non-natural epitope, which can be recognized by immune system, can be used as conjugate of modified monosaccharide as described below.

According to invention carbohydrate receptors of the defensive lectins of a patient can be also used for therapy or diagnostics. The immunologically active carbohydrates according to the invention includes carbohydrate which can be recognized by defensive lectins of a patient like collectins or mannose binding proteins of machophages or defensive lectins of natural killer cells. Mannose binding proteins may also recognize special GlcNAc and fucose containing molecules, especially when the monosaccharide residues are present in polyvalent form and terminally on glycoconjugates. Natural killer cells have lectins, which also bind polyvalent terminal GlcNAcs. According to invention it is possible to transfer carbohydrate receptors for the defensive lectins on pathogenic entities. Binding of the defensive lectins leads to defensive reaction against the tissue, cell or virus to which it is attached. The defensive reaction may be mediated by complement system or leukocytes like macrophages or natural killer cells or by other defensive means.

The immunologically active carbohydrate can be further conjugated to a toxic agent as described below to increase the reactivity against a pathogenic agent.

Humanized Antibodies
A Preferred Cancer Target

When the therapy according to the invention is targeted to cancer and terminal GlcNAc-cancer antigens as described in the present application. Galactosyltransferases like β4galactosyltransferase or β3galactosyltransferase can be used to transfer modified Gal from modified UDP-Gal to cell surface of the cancer cells. UDP-Gal is preferentially modified to carbon 6 by a spacer and a Galβ3Gal-saccharide epitope. In another preferred embodiment UDP-Gal is modified to position 2 of Gal as described by the invention. The modified monosaccharide is transferred on the cancer cells, which are then destroyed by immune response against Galα3Gal-saccharide. The transfer can be mediated by β4galactosyltransferase present in normal serum or additional purified or recombinant human by β4galactosyltransferase. Normal serum also contains a β3galactosyltransferase transferring to O-glycosidic GalNAc (Tn-cancer antigen), this transfer reaction also targets modified monosaccharides to cancer cells. Several human pathogens contain mammalian type oligosaccharide sequences like *Helicobacter pylori* or several *Neisseria* or *Haemophilus* strains and to these pathogens modified monosaccharides can be transferred by mammalian glycosyltransferases. Actually *Neisseria* and a parasite *Trypanosomn brucei* are known to transfer sialic acids originating from potential patient to their surfaces under pathogenic conditions.

Detection and Diagnostics

Furthermore the present invention is directed to methods for the detection of the pathogenic entities or activities by the invention. The specific transfer of modified monosaccharides to the pathogenic entities allows the detection of the pathogenic entities. For this purpose the modification of the monosaccharide need not to be toxic. The monosaccharide is modified by a label substance like a tag substance including for example an antigen detectable by an antibody, biotin, digotoxigenin, digitoxin or a directly detectable substance with examples of fluorescent substance like rhodamine or flourescein or substance with chemiluminesence activity or phosphorence substance or a specific molecular mass marker detectable by mass spectrometry.

In a preferred embodiment the modified monosaccharide is labeled with two label compounds, which are more preferentially a tag substance and a directly detectable substance and most preferentially a tag substance like biotin and a mass spectrometry label. The label substance is preferentially linked through a spacer to the modified monosaccharide. The invention is also directed to the use of said carbohydrate for diagnostics of the pathogenic entities and diseases related to them. The invention is specifically directed to the use of said carbohydrate/carbohydrates for diagnostics of infections, cancer and malignancies. The invention is especially directed to the use of immunologically active or toxic carbohydrate for the treatment diseases like infections, cancers and malignancies. Preferentially the cell surface carbohydrates are labeled by the modified monosaccharide. Modified monosaccharides aimed for detection are useful for detection of certain congenital disorders of glycosylation and under-sialylated LDL. Especially useful are labeled nucleotide sugars.

In a specific embodiment the the mofied monosaccharide are labeled with biotin and mass spectrometric labels. The modified monosaccharide are transferred by glycosyltransferring enzyme or enzymes, preferentially by a β4galactosyltransferase, to cell prepararations, the biotinylated fraction is purified and analyzed by mass spectrometry to reveal difference of expression of the glycosyltransferase acceptors. Preferentially glycopeptides produced by proteolysis of the sample are analyzed and recognized by mass spectrometry. In a preferred embodiment the method is used to detect difference of O-linked GlcNAc expression levels in cells under different conditions. Preferentially the differences in the same cell or tissue type are detected under different conditions. For the detection of the O-linked N-acetylglucosamine the intracellular proteins should be accessible in the cell preparation. The O-linked GlcNAc is known to be associated with different pathogenic conditions like diabetes.

The target oligosaccharide sequences of the invention can be a part of a glycolipid, a part of a glycoprotein, and/or a part of a N-acetyllactosamine chain. The oligosaccharide sequences on glycoproteins can also be a part of N-linked glycans or O-linked glycans of glycoproteins. Defects or changes in biosynthetic and/or biodegradative pathways of tumors lead to the synthesis of the oligosaccharide sequences of the invention both on glycolipids and glycoproteins. Terminal N-acetylglucosamine means that the non-reducing end GlcNAc residue in an oligosaccharide chain is not substituted by any other monosaccharide. The term oligosaccharide sequence indicates that the monosaccharide residue/residues in the sequence are part of a larger glycoconjugate, which contains other monosaccharide residues in a chain, which may be branched, or natural substituted modifications of oligosaccharide chains. The oligosaccharide chain is normally conjugated to a lipid anchor or to a protein.

The methods of treatment or the pharmaceutical compositions described above are especially preferred for the treatment of cancer diagnosed to express the cancer specific oligosaccharide sequences of the invention. The methods of treatment or the pharmaceutical compositions can be used together with other methods of treatment or pharmaceutical compositions for the treatment of cancer. Preferably the other methods or pharmaceutical compositions comprise cytostatics, anti-angiogenic pharmaceuticals, anti-cancer proteins, such as interferons or interleukins, or a use of radioactivity.

Transfer of a Non-modified Carbohydrates for Therapy

In a specific embodiment the pathogenesis preventing carbohydrate is a natural type of monosaccharide, which is covalently transferred to a pathogenesis-inducing carbohydrate receptor in vivo and blocks the pathogenesis-inducing carbohydrate receptor. The pathogenesis-inducing carbohydrate receptor is a defective glycosylation caused by a glycosylation disorder, or special glycosylation present in an autoimmune disease, a receptor carbohydrate in a pathogen-host interaction or a receptor carbohydrate present in a cancer-patient interaction, including metastasis. In preferred embodiments the transfer occurs in vivo for treatment of a disease. Preferentially a natural type of nucleotide sugar is used. The use of natural types of nucleotide sugars is directed to for treatment of glycosylation disorders, autoimmune diseases and infections, cancer and malignancies. Preferentially the transfer occurs to the surface of the pathogenic entity or entities. It is realized in the present invention that it is possible to perform glycosyltransfer reactions in vivo and that this is useful for therapeutics. According to present innovation it is also possible to administer nucleotide sugar or nucleotide sugar and a natural type of glycosyltransferase to a patient suffering from a glycosylation related disease and to at least partially correct the disorder. For example nucleotide sugars administered to blood circulation of patients suffering from some of the congenital disorders of glycosylation can be at least partially treated by administering appropriate nucleotide sugars to the patient, for example especially UDP-Gal, GDP-Fuc and GDP-Man but in some cases also other nucleotide sugars like UDP-GlcNAc, UDP-Glc, UDP-Xyl, UDP-GlcA and CMP-NeuNAc could be useful for such therapies. Part of the glycosyltransferase reactions could occur in serum of patient by transferases of serum.

Special activated salt of nucleotide sugar are described. Essentially pure manganese, magnesium or calcium salts of the nucleotide sugars or modified nucleotide sugars are useful pharmaceutical or therapeutical or nutritional compositions or for preparation of the composition, which can be used according to invention. Also pharmaceutical or therapeutical composition comprising nucleotide sugars or modified nucleotide sugars together with $Mn^{2+}$, $Ca^{2+}$ or/and $Mg^{2+}$ ions are preferred according to the invention. These ions can activate glycosyltransferase reactions and/or protect the nucleotide sugars or modified nucleotide sugars from degradation in patient. Special phosphatase resistant, but glycosyltransfer active forms of nucleotide sugars can be used, for example a form of sulphur-substituted phosphate ester. UDP-Gal described in the literature. The manganese salts are tolerable in blood circulation only in very low concentrations, due to neurotoxicity. Low amounts of manganese form of nucleotide sugars can be used in gastro-intestinal system or for example when injected to urinary bladder or directly to the tumor. For systemic use, calcium and/or magnesium ion complexes of the nucleotide sugars or use of tolerable calcium or magnesium salts together with nucleotide sugars is preferred. In a preferred embodiment highest tolerable levels of calcium or magnesium ions, most preferably the $Ca^{2+}$ and $Mg^{2+}$-ions in complex with nucleotide sugar and/or as tolerable salts with the nucleotide sugars are used in natural ratio of $Ca^{2+}$ and $Mg^{2+}$ in serum.

In a specific embodiment N-acetylneuraminic acid can be transferred in serum for example from CMP-NeuNAc to under sialylated low density lipoprotein particles (LDL) to prevent diseases caused by underssialylation of LDL.

In a preferred embodiment a nucleotide sugar or nucleotide sugars are used together with a glycosyltransferase to transfer monosaccharides to carbohydrate receptors of host microbe interaction. In a previous application a terminal GlcNAc-containing receptor for gastric pathogen *Helicobacter pylori* was described and the following application described prevention of the synthesis of the receptor by inhibiting glycosidases. According to present invention it is possible to prevent the adhesion of *Helicobacter pylori* to the receptor by a composition comprising UDP-Gal and galactosyltransferase.

When the nucleotide sugars or nucleotide sugars and glycosyltransferases are administerd orally, these can also perform in vivo glycosylation reactions to create probiotic or antibacterial oligosaccharides or glycoconjugates for example from lactose and also create receptor for probiotic bacteria on patients glycoconjugates or mask receptor for pathogenic bacteria.

Functional food compositions containing nucleotide sugars can be produced according to the invention. In a preferred embodiment the functional food contains both nucleotide sugars and glycosyltransferases. Preferential functional food composition is infant food, more preferentially infant formula. Human milk and other mammalian milks are known to contain nucleotide sugars and glycosyltransferases, therefore natural type of the substances of the patients species are useful and well tolerated.

Preferred amounts of the nucleotide sugar or nucleotide sugars or these in combination with one or more glycosyltransferases to be used vary from 5-500% of average the daily doses/kg obtained from milk. The nucleotide sugars are preferentially GDP-Fuc, CMP-NeuNAc, UDP-GlcNAc and UDP-Gal, other possible nucleotide sugars are GDP-Man, UDP-Xyl, UDP-GlcA and UDP-Glc. The monosaccharide residues on the nucleotide sugars are also useful as direct inhibitors of bacterial adhesion. In the present invention it is realized for the first time that nucleotide sugars and their degradation products like monosaccharide-1-phosphates are especially desired natural type glycoconjugates because these do not form non-enzymatic glycation end products, so called advanced glycation end products (AGEs) like free monosaccharides. For example, for mammalian species nucleotide monophosphates and nucleotide sugars are major type of monosaccharide conjugates beside glycolipids.

Use of Antibodies, Preferably from Animals, in Gastrointestinal and Food Related Applications The present invention is specifically directed to the use of substances and antibodies binding to tumor specific oligosaccharide sequences according to the present invention for theraphies in gastrointestinal tract of the patient, preferably in human patient. The theraphetic antibodies for use in human gastrointestinal tract may be antibodies produced by animals for example antibodies in milks of domestic animals, for example in milk of domestic ruminants such as cows, sheep, goat or buffalo or antibodies produced in hen eggs. The animals can be immunized tumor specific carbohydrate conjugates as known in the art. The present invention is also directed to other acceptable, preferably food acceptable proteins which can be used inhibition or destruction of tumors in human gastrointestinal tract, such substances includes plant lectins which are specific for the tumor specific oligosaccharide sequences. The present invention is directed to functional foods and food additives containing antibodies recognizing the tumor specific oligosaccharide sequences according to the present invention in gastrointestinal tract, the present invention is directed also use of other food acceptable substances especially lectins binding to the tumor specific oligosaccharide sequences of gastrointestinal tract in functional foods or as food additives.

Screening of Substances Binding to the Tumor Specific Terminal GlcNAcs

The present invention is specifically directed to the use of the tumor specific terminal-GlcNAc-oligosaccharide sequences for the screening of specific binders with regard to the structures. The screening allows finding of optimal binding substances for the tumor specific oligosaccharide sequences according to the present invention. The specific binders may be therapheutic or diagnostic antibodies or other molecules binding to the glycans as described by the present invention above.

The screening of the substances binding to the oligosaccharide sequences according to the invention may be performed in an enzyme linked immmonoassays (so called ELISA-assays). Direct binding can be measured for example when either the binding substance or the terminal-GlcNAc-glycan structure is linked to a solid phase matrix.

Free oligosaccharides or oligosaccharide conjugates according to the present invention can be also used as specific inhibitors in the assays. Fluoresence polararization difference and NMR are examples of liquid phase methods to be used for screening of the substances binding to the oligosaccharide sequences according to the invention.

Cancer Vaccines

Furthermore, according to the invention the tumor specific oligosaccharide sequences or analogs or derivatives thereof can be used as cancer or tumor vaccines in man to stimulate immune response to inhibit or eliminate cancer or tumor cells. The treatment may not necessarily cure cancer or tumor but it can reduce tumor burden or stabilize a cancer condition and lower the metastatic potential of cancers. For the use as vaccines the oligosaccharides or analogs or derivatives thereof can be conjugated, for example, to proteins such as BSA or keyhole limpet hemocyanin, lipids or lipopeptides, bacterial toxins such as cholera toxin or heat labile toxin, peptidoglycans, immunoreactive polysaccharides, or to other molecules activating immune reactions against a vaccine molecule. A cancer or tumor vaccine may also comprise a pharmaceutically acceptable carrier and optionally an adjuvant. Suitable carriers or adjuvants are, e.g., lipids known to stimulate the immune response. The saccharides or derivatives or analogs thereof, preferably conjugates of the saccharides, can be injected or administered mucosally, such as orally or nasally, to a cancer patient with tolerated adjuvant molecule or adjuvant molecules. The cancer or tumor vaccine can be used as a medicine in a method of treatment against cancer or tumor. Preferably the method is used for the treatment of a human patient. Preferably the method of treatment is used for the treatment of cancer or tumor of a patient, who is under immunosuppressive medication or the patient is suffering from immunodeficiency.

Furthermore it is possible to produce a pharmaceutical composition comprising the tumor specific oligosaccharide sequences or analogs or derivatives thereof for the treatment of cancer or tumor. Preferably the pharmaceutical composition is used for the treatment of a human patient. Preferably the pharmaceutical composition is used for the treatment of cancer or tumor, when patient is under immunosuppressive medication or he/she is suffering from immunodeficiency. The methods of treatment or the pharmaceutical compositions described above are especially preferred for the treatment of cancer or tumor diagnosed to express the tumor specific oligosaccharide sequences of the invention. The methods of treatment or the pharmaceutical compositions can be used together with other methods of treatment or pharmaceutical compositions for the treatment of cancer or tumor. Preferably the other methods or pharmaceutical compositions comprise cytostatics, anti-angiogenic pharmaceuticals, anti-cancer proteins, such as interferons or interleukins, or a use of radioactivity.

Use of antibodies for the diagnostics of cancer or tumor and for the targetting of drugs to cancer has been described with other antigens and oligosaccharide structures (U.S. Pat. Nos. 4,851,511; 4,904,596; 5,874,060; 6,025,481; 5,795,961; 4,725,557; 5,059,520; 5,171,667; 5,173,292; 6,090,789; 5,708,163; 5,902,725 and 6,203,999). Use of cancer specific oligosaccharides as cancer vaccines has also been demonstrated with other oligosaccharide sequences (U.S. Pat. Nos. 5,102,663; 5,660,834; 5,747,048; 5,229,289 and 6,083,929).

Combination of the Therapheutic and Diagnostic Methods

Present invention is specifically directed to analysis of abnormal and normal glycosylation structures from human tumors and cancers and use of the analyticall information for the production of therapheutic antibodies or cancer vaccines according to the invention. Present invention is specifically directed to treatment of cancer including following steps:

1. analysis of glycosylation of tumor or cancer tissue of a patient
2. analysis of normal glycosylation of the tissue containing the cancer
3. Use of the theraphies according to the present invention if the patient has tumor specific oligosaccharide sequences according to the present invention in cancer but does not have the tumor specific oligosaccharide sequences or has these in much lower extent on cell surfaces in the normal tissue.

The data in examples shows the usefulness of the combination of analysis of the tumor specific structures according to the invention, because there are individual variations in glycosylation of tumors and normal tissues. The normal tissue close to tumor may also be contaminated partially contaminated by materials secreted by tumor which may be taken to consideration when analyzing the normal tissue data.

The substance according to the invention can be attached to a carrier. Methods for the linking of oligosaccharide sequences to a monovalent or multivalent carrier are known in the art. Preferably the conjugation is performed by linking the cancer specific oligosaccharide sequences or analogs or derivatives thereof from the reducing end to a carrier molecule. When using a carrier molecule, a number of molecules of a substance according to the invention can be attached to one carrier increasing the stimulation of immune response and the efficiency of the antibody binding. To achieve an optimal antibody production, conjugates larger than 10 kDa carrying typically more than 10 oligosaccharide sequences are preferably used.

The oligosaccharide sequences according to the invention can be synthesized, for example, enzymatically by glycosyltransferases, or by transglycosylation catalyzed by a glycosidase enzyme or a transglycosidase enzyme, for review see Ernst et al., 2000. Specificities of the enzymes and their use of co-factors such as nucleotide sugar donors, can be engineered. Specific modified enzymes can be used to obtain more effective synthesis, for example, glycosynthase is modified to achieve transglycosylation but not glycosidase reactions. Organic synthesis of the saccharides and conjugates of the invention or compounds similar to these are known (Ernst et al., 2000). Carbohydrate materials can be isolated from natural sources and be modified chemically or enzymatically into compounds according to the invention. Natural oligosaccharides can be isolated from milks of various ruminants and other animals. Transgenic organisms, such as cows or microbes, expressing glycosylating enzymes can be used for the production of saccharides.

It is possible to incorporate an oligosaccharide sequence according to the invention, optionally with a carrier, in a pharmaceutical composition, which is suitable for the treatment of cancer or tumor in a patient. Examples of conditions treatable according to the invention are cancers in which the tumor expresses one or more of the tumor specific oligosaccharides described in the invention. The treatable cancer cases can be discovered by detecting the presence of the tumor specific oligosaccharide sequences in a biological sample taken from a patient. Said sample can be a biopsy or a blood sample.

The pharmaceutical composition according to the invention may also comprise other substances, such as an inert vehicle, or pharmaceutically acceptable carriers, preservatives etc., which are well known to persons skilled in the art.

The substance or pharmaceutical composition according to the invention may be administered in any suitable way. Methods for the administration of theraphuetic antibodies or vaccines are well-known in the art The term "treatment" used herein relates to both treatment in order to cure or alleviate a disease or a condition, and to treatment in order to prevent the development of a disease or a condition. The treatment may be either performed in a acute or in a chronic way.

The term "patient", as used herein, relates to any mammal in need of treatment according to the invention.

When a tumor specific oligosaccharide or compound specifically recognizing tumor specific oligosaccharides of the invention is used for diagnosis or typing, it may be included, e.g., in a probe or a test stick, optionally in a test kit. When this probe or test stick is brought into contact with a sample containing antibodies from a cancer patient or cancer cells or tissue of a patient, components of a cancer positive sample will bind the probe or test stick and can be thus removed from the sample and further analyzed.

In the present invention the term "tumor" means solid multicellular tumor tissues. Furthermore the term "tumor" means herein premalignant tissue, which is developing to a solid tumor and has tumor specific characteristics. The term "tumor" is not referring herein to a single cell cancer such as a leukaemia or to cultured cancer cells or a cluster of such cells. The present invention is preferably directed to primary human cancer samples. It is well known that glycosylations in cultivated cancer cells vary and are not in general relevant with regerd to cancer. It is also known that transfections, cell culture media and dividing solid tumor to single cells may have daramatic effects for glycosylations. When referring to theraphies tumor specific oligosaccharides or oligosaccharide sequences (possibly occasionally referred as cancer specific oligosaccharides/oligosaccharide sequences) are targeted for treatment of all kinds of cancers and tumors. The term cancer includes tumors.

The present invention is specifically directed to the treatment of all types of cancer or tumors expressing the tumor specific oligosaccharide sequences according to the present invention. Examples of preferred cancer types includes cancers of larynx, colon cancer, stomach cancer and lung cancer. These cancer types are especially preferred for the N-glycan type terminal GlcNAc related methods and compositions according to the present invention. Lung cancer is a preferred target for the protein linked GlcNAc related methods and compositions according to the present invention. The O-glycan type substances are especially preferred for use in methods and compositions according to the present invention for ovarian cancer and mucinous carcinomas, especially for ovarian adenocarcinomas. In a preferred embodiment the terminal GlcNAc-structures of poly-N-acetyllactosamine type is used for theraphy or diagnostics of hypernephroma cancers. The present invention is also specifically directed to the treatment according to the present invention for any type of cancer or tumor which has surface expression of the terminal GlcNAc-structures according to the present invention.

Glycolipid and carbohydrate nomenclature is according to recommendations by the IUPAC-IUB Commission on Biochemical Nomenclature (Carbohydr. Res. 1998, 322:167; Carbohydr. Res. 1997, 297:1; Eur. J. Biochem. 1998, 257:29).

It is assumed that Gal, Glc, GlcNAc, and NeuNAc are of the D-configuration, Fuc of the L-configuration, and that all monosaccharide units are in the pyranose form. Glucosamine is referred as GlcN and galactosamine as GalN. Glycosidic linkages are shown partly in shorter and partly in longer nomenclature, the linkages α3 and α6 of the NeuNAc-residues mean the same as (α2-3 and α2-6, respectively, and β1-3, β1-4, and β1-6 can be shortened as β3, β4, and β6, respectively. Lactosamine or N-acetyllactosamine or Galβ3/4GlcNAc means either type one structure residue Galβ3GlcNAc or type two structure residue Galβ1-4GlcNAc, and sialic acid is N-acetylneuraminic acid or NeuNAc, Lac refers to lactose and Cer is ceramide.

The present invention is further illustrated in examples, which in no way are intended to limit the scope of the invention:

EXAMPLES

Example 1

Culturing and Labelling of Bacteria

The recombinant G-fimbriated *Escherichia coli* strain IHE11088 (pRR-5), expressing the GlcNAc-recognizing GafD adhesin (Rhen, M. et al., 1986), was cultured in Luria broth containing tetracyclin (25 µg/ml) and 10 µl [$^{35}$S]-methionine (400 mCi; Amersham Pharmacia Biotech, Little Chalfont, UK) at 37° C. over night. The bacteria were harvested by centrifugation, washed two times with phosphatebuffered saline, pH 7.2 (PBS), and resuspended in PBS to $1\times10^9$ CPU/ml. The specific activities were approximately 100 CFU/cpm.

Labelling of *Erythrina cristagalli* Lectin

The Galβ4GlcNAcβ-binding lectin from *Erythrina cristagalli* (Teneberg et al., 1994) was purchased from Vector Laboratories Inc., Burlingame, Calif. Batches of 100 μg protein were labelled with $^{125}$I, using Na$^{125}$I (100 mCi/ml; Amersham Pharmacia Biotech), according to the IODO-GEN protocol of the manufacturer (Pierce, Rockford, Ill.). Approximately $5\times10^3$ cpm/μg protein was obtained.

Glycosphingolipid Binding Assays

Binding of radiolabeled bacteria and lectin to glycosphingolipids separated on thin-layer chromatograms was done as reported previously (Teneberg et al., 1994, Hansson et al., 1985). Thin-layer chromatography of glycosphingolipids was performed on aluminium-backed silica gel 60 HPTLC plates (Merck, Darmstadt, Germany), using chloroform/methanol/water 60:35:8 (by volume) as solvent system. Dried chromatograms were dipped for 1 min in diethylether/n-hexane 1:5 (by volume) containing 0.5% (w/v) polyisobutylmethacrylate (Aldrich Chem. Comp. Inc., Milwaukee, Wis.). After drying, the chromatograms were soaked in PBS containing 2% bovine serum albumin (BSA) (w/v), 0.1% NaN$_3$ (w/v) for 2 hr at room temperature. The chromatograms were subsequentely covered with radiolabelled bacteria diluted in PBS ($2\text{-}5\times10^6$ cpm/ml) or radiolabelled lectin in BSA ($2\times10^3$ cpm/ml). Incubation was done for 2 hr at room temperature, followed by repeated washings with PBS. The chromatograms were thereafter exposed to XAR-5X-ray films (Eastman Kodak, Rochester, N.Y.) for 12 hr.

Example 2

Demonstration of Tumor Specificity of Terminal GlcNAc Structure.

Thin-layer overlay assays were performed with radiolabelled G-fimbriated *Escherichia coli* to screen various tumors and normal tissues. The *E. coli* strain IHE11088 (pRR-5) specifically recognizes terminal GlcNAcβ-structures (Rhen, M. et al. 1986). Binding active glycolipids were found in non-acid fraction from one of four hypemephroma tumors studied (FIG. 1). No binding was observed towards corresponding fraction of non-acid glycosphingolipids from human normal kidney or to other control tissues studied.

Example 3

Characterizations of Terminal GlcNAcβ-structures from Human Hypernephroma.

Figure 2:
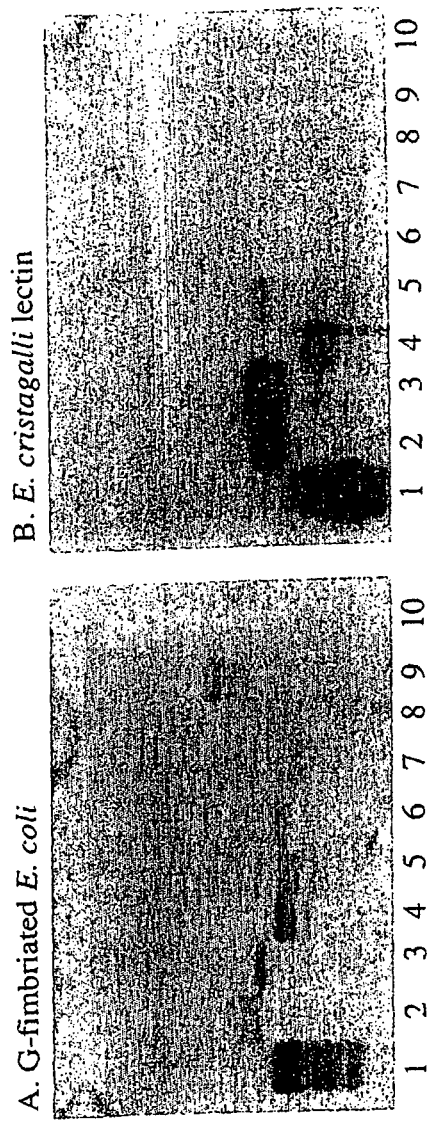
FIG. 2. Thin-layer overlay assays A) using [$^{35}$S]-labelled, GlcNAcβ-specific E. coli and B) [$^{125}$I]-labelled Galβ4GlcNAcβ-specific lectin from Erythrina cristagalli. Lanes 1-8: Subfractions of non-acid glycosphingolipids from human hypernephroma. Lane 9: Reference glycosphingolipid GlcNAcβ3Galβ4Glcβ1Cer. Lane 10: Reference glycosphingolipid globoside GalNAcβ3Galα4Galβ4Glcβ1Cer.

Non-acid glycosphingolipids from human hypernephroma tumor were fractionated and analysed by binding with the GlcNAcβ-specific G-fimbriated *E. coli* (FIG. 1A) and lectin from *Erythrina cristagalli* which recognizes terminal Galβ4GlcNAcβ-structures (FIG. 2B) by thin-layer overlay assay. The two binding reagents show partially overlapping glycospingolipid binding species. The data indicates that the terminal GlcNAc-species are mostly present on N-acetyllactosamine type non-acid glycosphingolipids. The terminal GlcNAc-species which do not have an overlap with lectin binding activity have most probably terminal structures where N-acetyllactosamine is derivatized by GlcNAc such as GlcNAcβ3Galβ3/4GlcNAcβ-; diffuse bands probably also indicates the presence of an isomeric form GlcNAcβ6Galβ3/4GlcNAcβ-. The sample also appears to contain minor species where the terminal GlcNAc and N-acetyllactosamine are present in the same glycolipid. This indicates the presence of branched structures such as Galβ3/4GlcNAcβ3(GlcNAcβ6)Galβ3/4GlcNAcβ- and GlcNAcβ3(Galβ3/4GlcNAcβ6)Galβ3/4GlcNAcβ-; the size distribution of the glycosphingolipids probably also indicates species with two or even more terminal GlcNAcs. The binding of the *Erythrina* cristagalli lectin indicates that most of the lactosamine probably has the type two N-acetyllactosamine structure Galβ4GlcNAc.

The glycolipids were partially analyzed by FAB mass spectrometry and by EI masspectrometry after permethylation, which showed presence of terminal HexNAc and that the smallest species with terminal GlcNAc is a pentasaccharide glycosphingolipid probably of lacto or neolacto series. Also 7-meric and larger structures up to 15-mer were observed (FIG. 1). The binding of the lectins indicates that most of the lactosamine probably has the type two N-acetylactosamine structure.

Example 4

Materials and Methods for Protein Linked Structures and Labeling by Galactosyltransferase Isolation of glycans from formalin-fixed or formalin-fixed and paraffin-embedded tissue samples. Prior to glycan isolation from formalin-fixed samples, proteins were enriched by chloroform-methanol extraction essentially as described in (Manzi et al., 2000). Quantitative extraction of glycoproteins was confirmed by radioactively labelled glycoprotein standards (not shown). Prior to glycan isolation from formalin-fixed and paraffin-embedded samples, the samples were deparaffinised. Glycans were detached from sample glycoproteins by non-reductive β-elimination and purified by chromatographic methods.

MALDI-TOF MS. MALDI-TOF mass spectrometry was performed with a Voyager-DE STR BioSpectrometry Workstation, essentially as in (Saarinen et al., 1999; Papac et al., 1996; Harvey, 1993).

Exoglycosidase digestions. All exoglycosidase reactions were performed essentially as described in (Nyman et al., 1998; Saarinen et al., 1999) and analysed by MALDI-TOF MS. The enzymes and their specific control reactions with characterised oligosaccharides were: βN-acetylglucosaminidase (*Streptococcus pneumoniae*, recombinant, *E. coli*; Calbiochem, USA) digested GlcNAcβ1-6Gal—R but not GalNAcβ1-4GlcNAcβ1-3/6Gal—R; β1,4-galactosidase (*Streptococcus pneumnoniae*, recombinant, *E. coli*; Calbiochei, USA) digested Galβ1-4GlcNAc—R but not Galβ1-3GlcNAc—R; α-mannosidase (Jack bean; Glyko, UK) transformed a mixture of high-mannose N-glycans to the Man$_1$GlcNAc$_2$ N-glycan core trisaccharide. Control digestions were performed in parallel and analysed similarly to the analytical exoglycosidase reactions.

Synthesis of UDP-GalN-biotin. UDP-galactosamine (UDP-GalN) is formed from UDP-Glc and galactosamine-1-phosphate by the action of galactose-1-phosphate uridyltransferase (E.C. 2.7.7.12; Sigma, USA). A typical synthesis protocol is described below. The reaction mixture contains 10 mM galactosamine-1-phosphate, 20 mM UDP-Glc, 5 U/ml of galactose-1-phosphate uridyltransferase, 100 mM Na-HEPES pH 8.0, 5 mM MgCl$_2$, and 5 mM β-mercaptoethanol. The reaction vessel is incubated at room temperature under nitrogen atmosphere for 3 days, after which nucleotide sugars are isolated from the reaction mixture with a graphitised carbon column essentially as in (Mäki et al., 2002). The nucleotide sugar mixture, containing UDP-Glc and UDP- GalN, is incubated with a molar excess of sulfosuccinimidyl-6-(biotinamido)hexanoate (sulfo-NHS-LC-biotin; Pierce, USA) in 50 mM $NH_4HCO_3$ at room temperature for 2.5 hours. The product, UDP-GalN-biotin, uridine 5'-diphospho-N-(6-biotinamidohexanoyl)galactosamine, is purified by gel filtration and reversed phase HPLC.

Labeling of terminal GlcNAc residues in oligosaccharides and tissue sections with UDP-GalN-biotin. N-(6-biotinamidohexanoyl)galactosamine can be transferred from UDP-GalN-biotin to a terminal GlcNAc containing acceptor with a recombinant β1,4-galactosyltransferase similar to the enzyme described in (Ramakrishnan and Qasba, 2002). In a typical procedure, an oligosaccharide acceptor such as GlcNAcβ1-3Galβ1-4GlcNAcβ1-3Galβ1-4Glc, or deparaffinised formalin-fixed paraffin-embedded tissue sections, are incubated at +37° C. with a reaction mixture containing 10 mM UDP-GalN-biotin, 160 U/l enzyme, 100 mM Tris-HCl, and 20 mM $MnCl_2$. After washing, the biotin groups are visualised by standard methods in the art, using streptavidin or avidin coupled reagents, for example streptavidin-FITC.

Figure 7A:
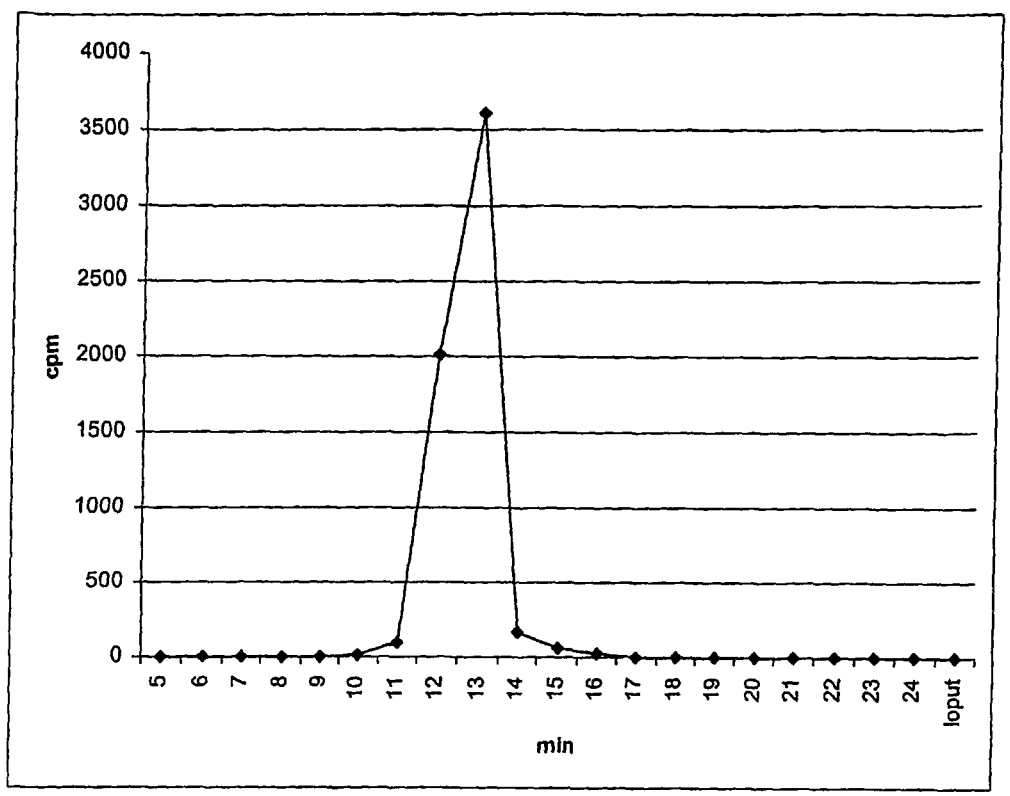
FIG. 7A. [$^{14}$C]Gal labelled oligosaccharides from N-glycosidase F digested lung adenocarcinoma sample. Glycans were subjected to gel filtration HPLC with a Superdex Peptide HR 10/30 column (Pharmacia, Sweden) in 50 mM NH$_4$HCO$_3$ (pH about 8.3) at a flow rate of 1 ml/min. 1 ml fractions were collected and counted for radioactivity. Fractions at 12-15 min were pooled.
Figure 7B:
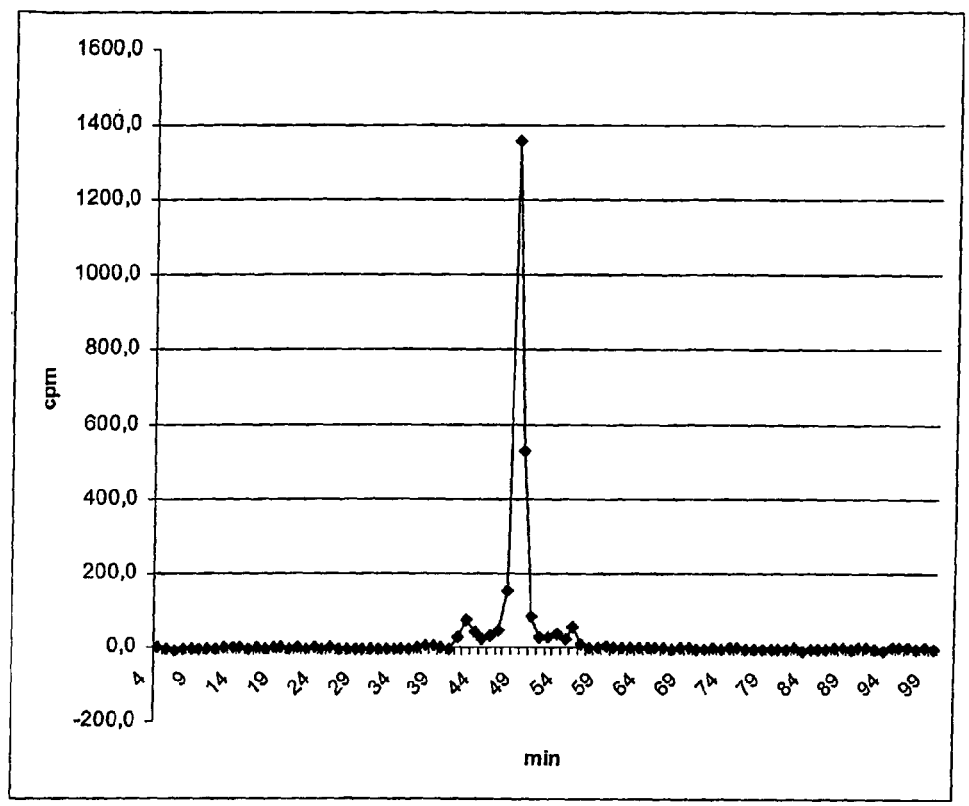
FIG. 7B. [$^{14}$C]Gal labelled oligosaccharides from N-glycosidase F digested lung adenocarcinoma sample. The 12-15 min pool from Superdex Peptide gel filtration HPLC (FIG. 10A) was subjected to HPLC with a 4.6×250 mm Hypercarb 5u column (Thermo Hypersil, USA) in 10 mM NH$_3$ at a flow rate of 0.7 ml/min, with a linear gradient of 0% to 40% acetonitrile in the mobile phase in 100 minutes. 0.7 ml fractions were collected and counted for radioactivity.

Labeling of terminal GlcNAc residues in tissue sections with UDP-[$^{14}$C]Gal. Formalin-fixed and paraffin-embedded tissue sections were deparaffinised and incubated at +37° C. with a reaction mixture containing UDP-[$^{14}$C]Gal, 200 U/I bovine milk β1,4-galactosyltransferase (Calbiochem, USA), 50 mM Na-MOPS pH 7.4, and 20 mM $MnCl_2$. After washing, the labelled sections were subjected to autoradiography. N-glycans were detached from the tissue sections with *Chryseobacterium meningosepticum* N-glycosidase F (Calbiochem, USA) essentially as in (Nyman et al., 1998). Chromatography was performed as described in figure legends to FIGS. 7A and 7B.

Example 5

Figure 3A:
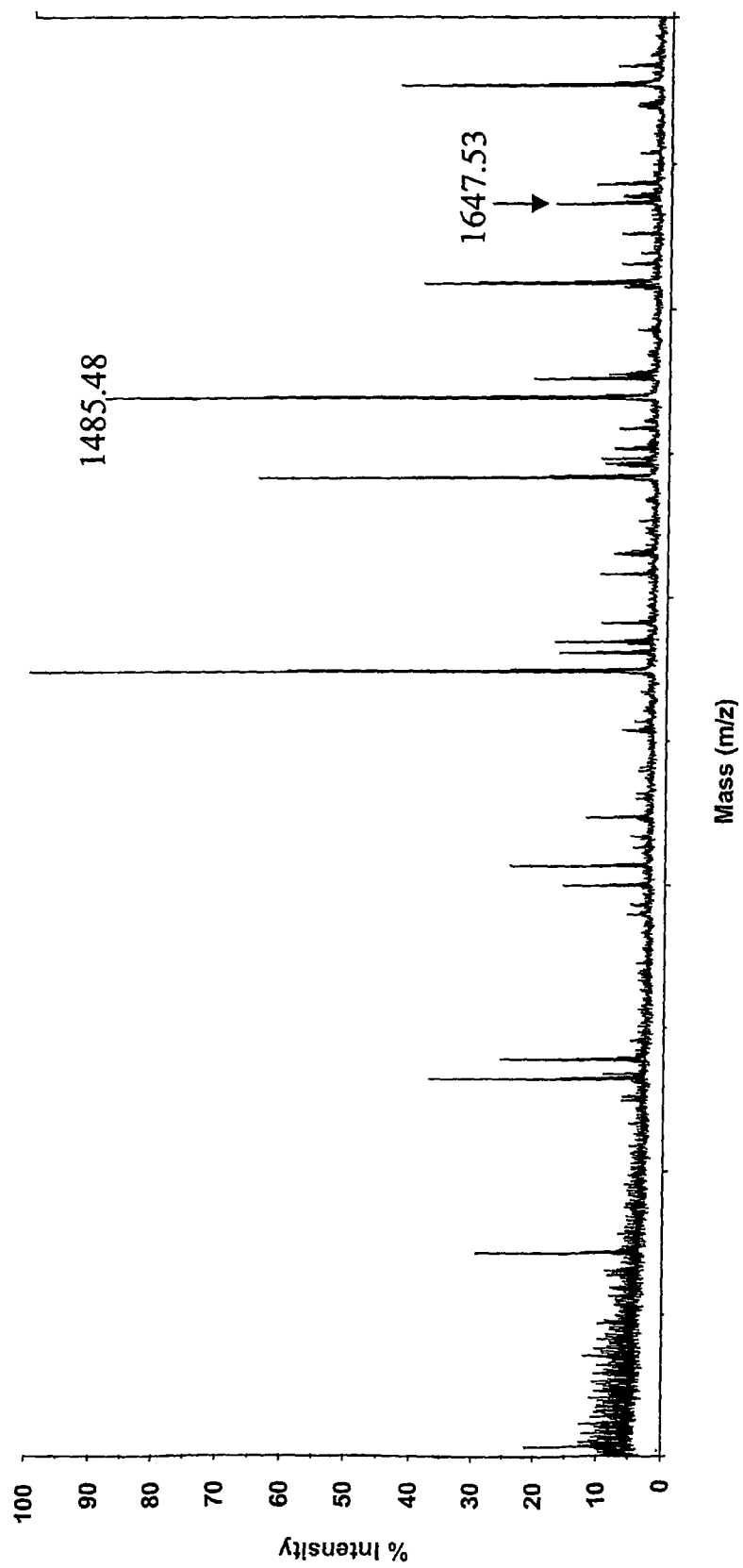
FIG. 3A. Positive ion reflector mode MALDI-TOF mass spectrum of lung adenocarcinoma sample neutral glycans.
Figure 3B:
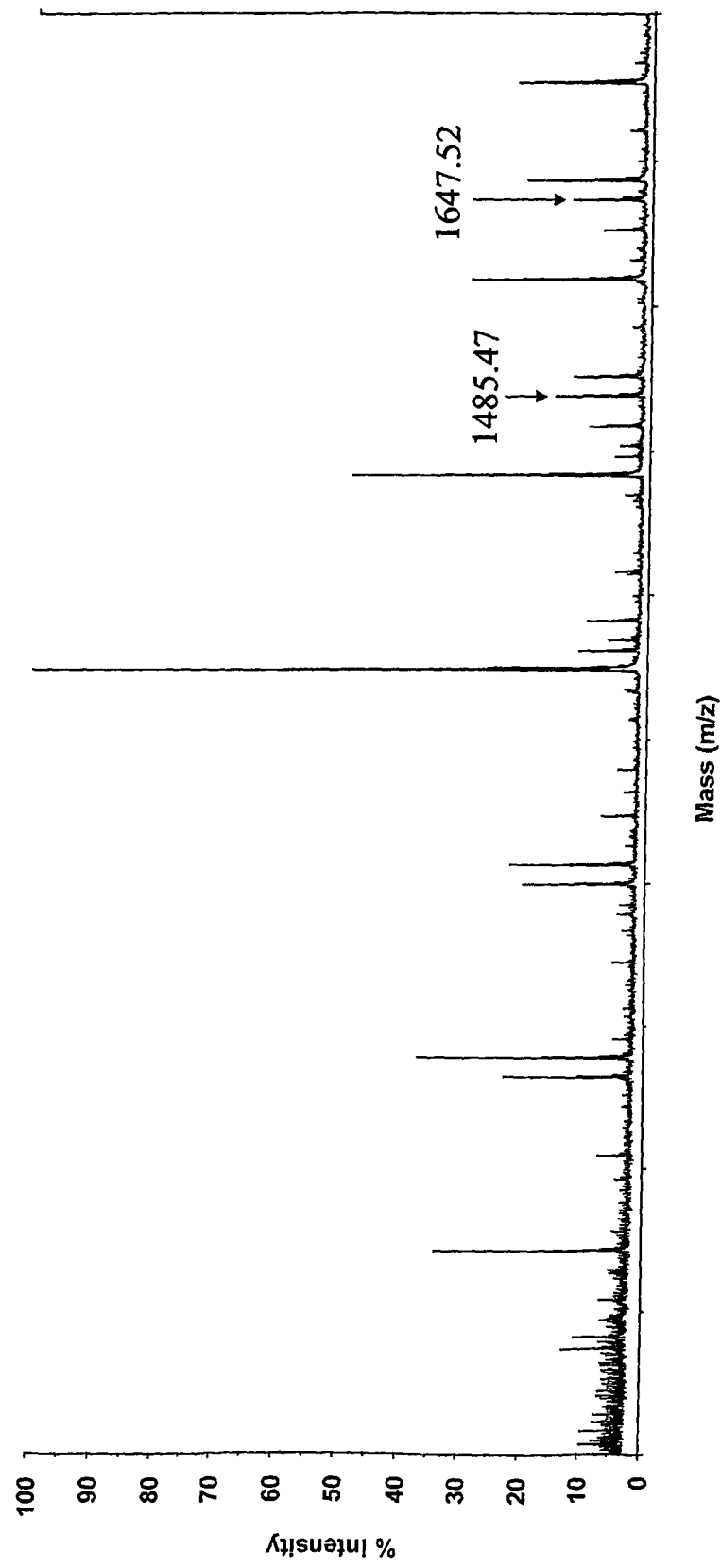
FIG. 3B. Positive ion reflector mode MALDI-TOF mass spectrum of healthy lung sample neutral glycans.
Figure 3C:
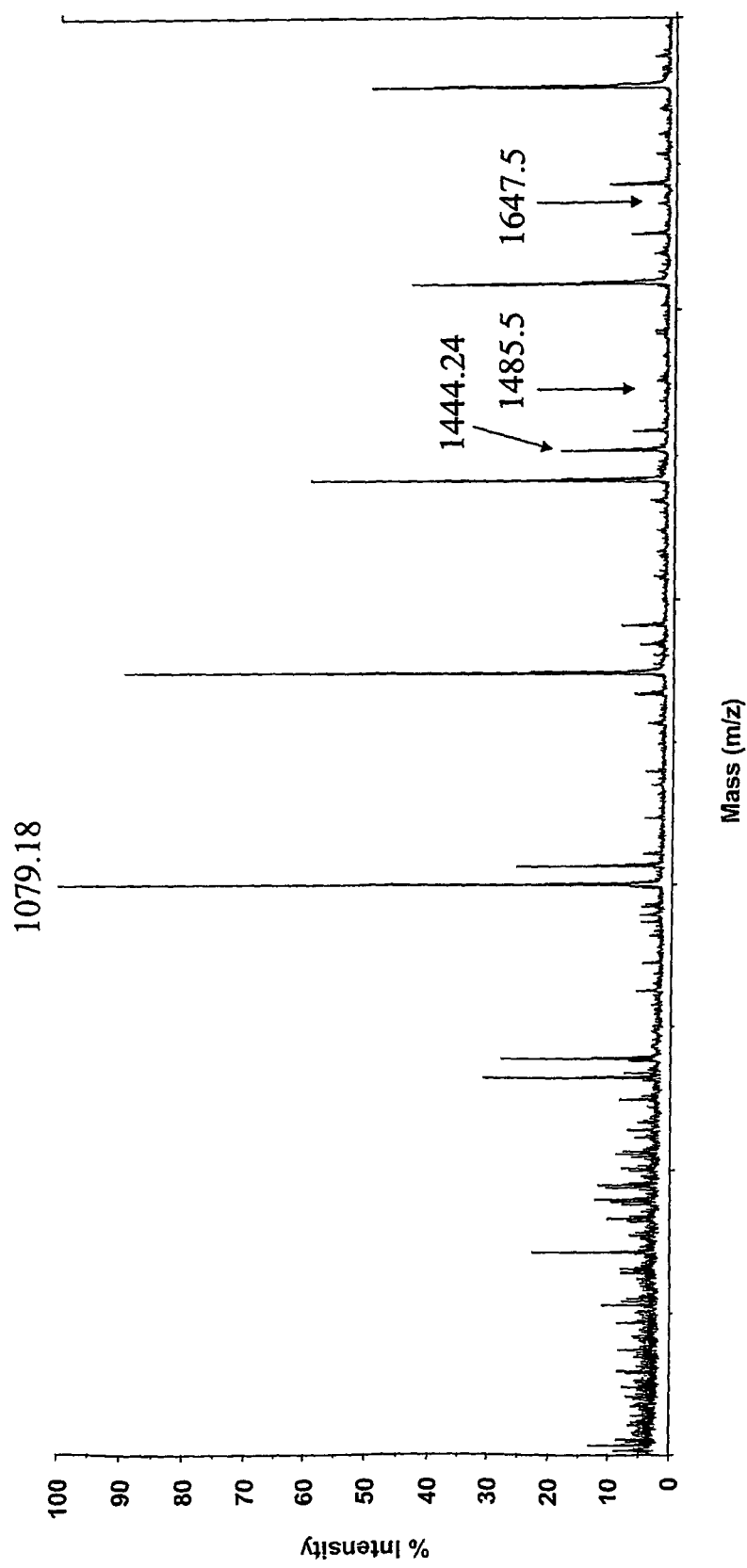
FIG. 3C. Positive ion reflector mode MALDI-TOF mass spectrum of lung adenocarcinoma sample neutral glycans after S. pneumoniae β-N-acetylglucosaminidase digestion.
Figure 3D:
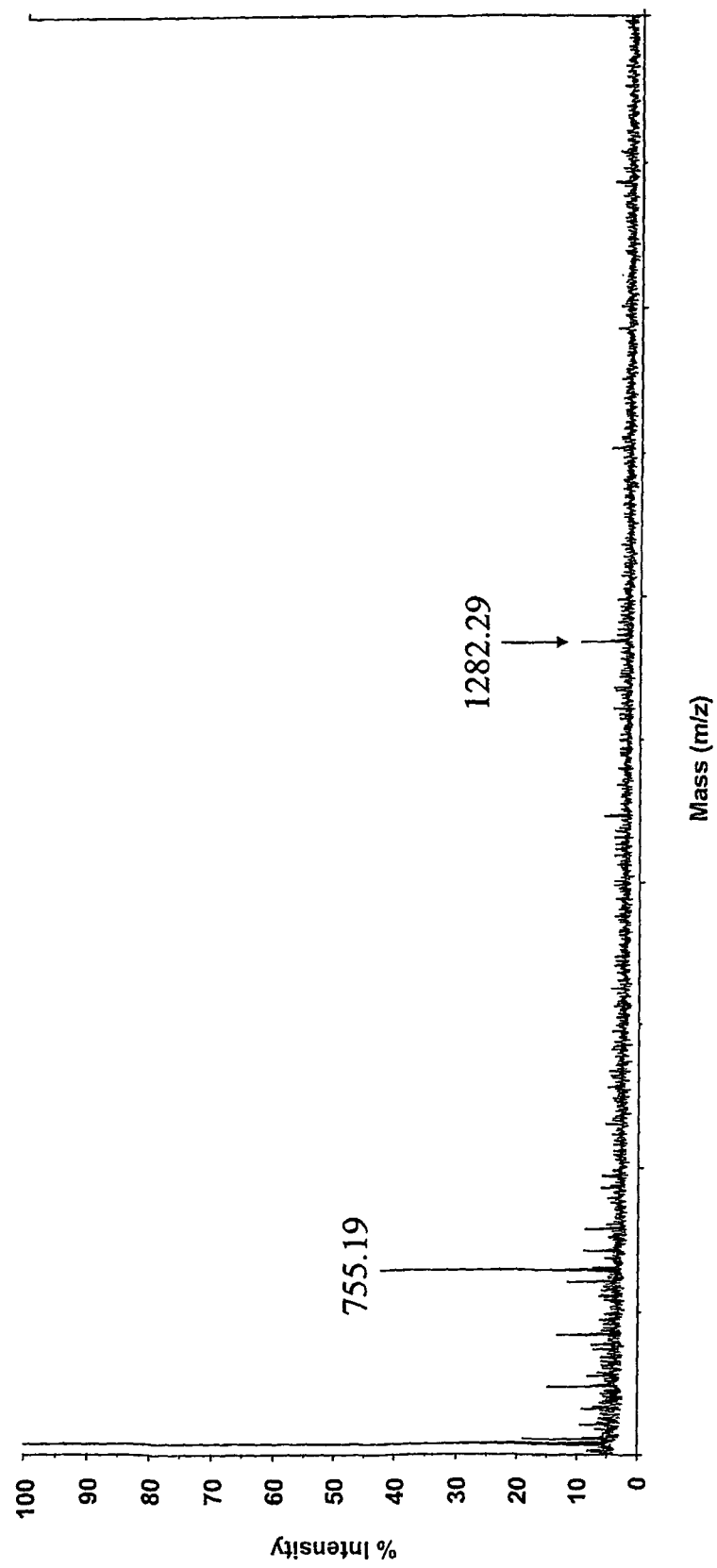
FIG. 3D. Positive ion reflector mode MALDI-TOF mass spectrum of lung adenocarcinoma neutral glycans after S. pneumoniae β-N-acetylglucosaminidase and jack bean α-mannosidase digestions.

Cancer-associated terminal GlcNAc containing N-glycans from lung adenocarcinoma samples. Formalin-fixed samples, from tumor and surrounding healthy tissue, were obtained from a patient with lung adenocarcinoma. There was a significant difference between the neutral glycans isolated from the tumor sample (FIG. 3A) and the healthy tissue sample (FIG. 3B), namely a peak at m/z 1485.48, corresponding to the ion [$Hex_3HexNAc_4Fuc_1+Na$]$^+$ (calc. m/z 1485.53). The relative intensity of this glycan peak was elevated over 6.1 times in the tumor sample, as compared to healthy tissue. Furthermore, a peak at m/z 1647.53, corresponding to the ion [$Hex_4HexNAc_4Fuc_1+Na$]$^+$ (calc. m/z 1647.59), had a higher signal intensity in the tumor sample. Upon β-N-acetylglucosaminidase digestion (FIG. 3C), the two peaks were completely transformed into peaks at m/z 1079.18, corresponding to the ion [$Hex_3HexNAc_2Fuc_1+Na$]$^+$ (calc. m/z 1079.38), and 1444.24, corresponding to the ion [$Hex_4HexNAc_3Fuc_1+Na$]$^+$ (calc. m/z 1444.51), respectively, indicating the presence of terminal β-GlcNAc residues. Jack bean α-mannosidase digestion (FIG. 3D) further transformed these peaks into peaks at m/z 755.19, corresponding to the ion [$Hex_1HexNAc_2Fuc_1+Na$]$^+$ (calc. m/z 755.27), and 1282.29, corresponding to the ion [$Hex_3HexNAc_3Fuc_1+Na$]$^+$ (calc. m/z 1282.45), respectively. However, α-mannosidase digestion before the β-N-acetylglucosaminidase digestion did not affect the two peaks, indicating that the α-Man residues were subterminal to the β-GlcNAc residues. In addition, β1,4-galactosidase digestion of the original neutral glycan sample completely transformed the peak at m/z 1647.5 into the peak at m/z 1485.5, indicating the presence of a terminal Galβ1-4GlcNAc unit. Taken together, the results suggest that the lung adenocarcinoma tumor sample contained highly elevated amounts of the complex N-linked glycan core structure GlcNAcβ-Manα1-6(GlcNAcβ-Manα1-3)Manβ1-4GlcNAcβ1-4(Fucα1-6)GlcNAc, and slightly elevated amounts of the mono-β1,4-galactosylated (to GlcNAc) derivative of the former structure, as compared to the surrounding healthy tissue.

Example 6

Occurrence of the terminal GlcNAc containing N-glycans in carcinoma samples. The occurrence of the abovementioned structures in various tumor and healthy control samples was studied by isolating and analysing the neutral glycan fractions by MALDI-TOF MS and exoglycosidase digestions. The analysed tumor-control pairs were: 7 lung cancer sample pairs, and one pair each of colon, stomach, and larynx cancer samples. It turned out that in every case the relative abundance of the two terminal GlcNAc containing N-glycan at m/z 1485.5, was elevated in the cancerous sample. However, there were significant individual differences in the expression levels of this glycan epitope both in the healthy state and in cancer. Table 1 summarizes the differential expression of the m/z 1485.5 N-glycan in relation to the bulk of the isolated neutral glycan fraction.

Example 7

Figure 4A:
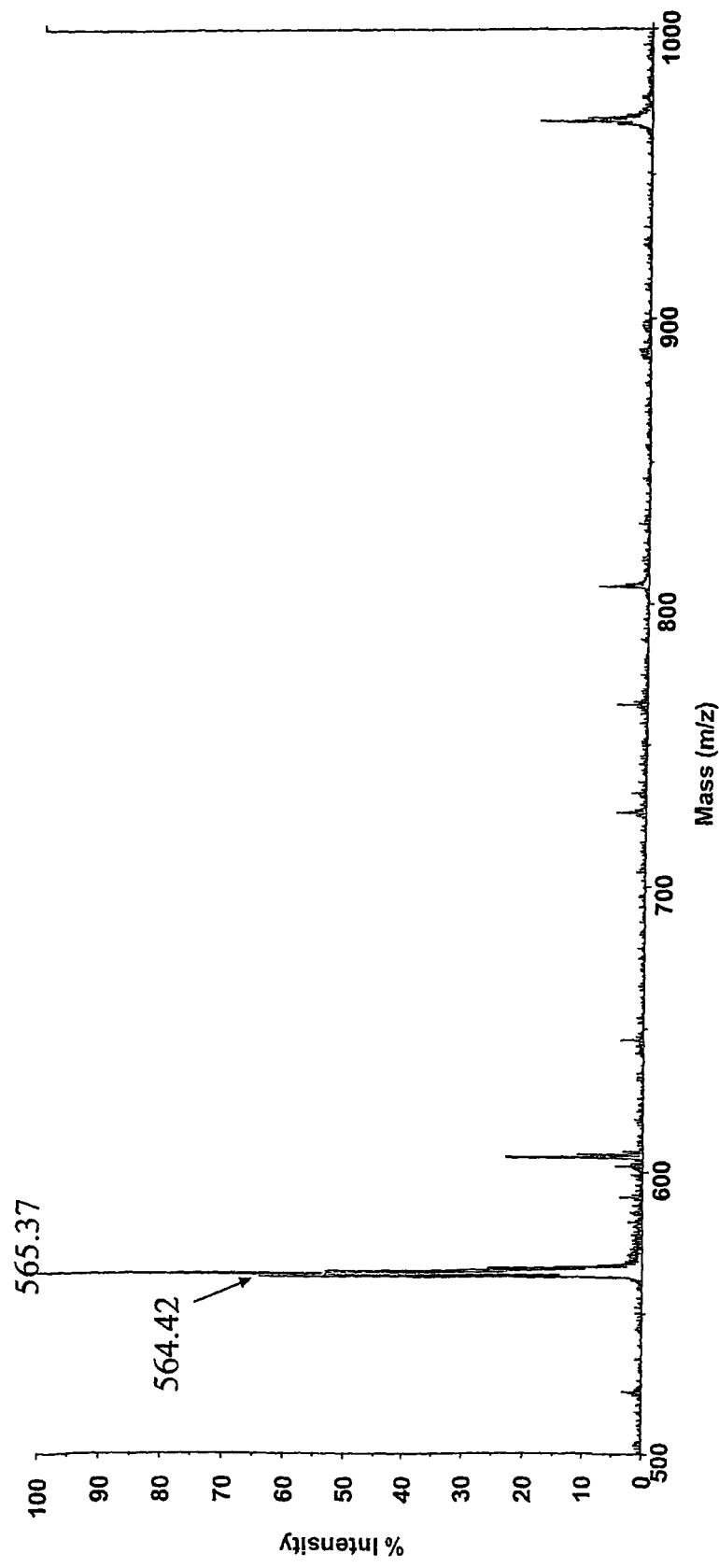
FIG. 4A. Negative ion linear mode MALDI-TOF mass spectrum of purified nucleotide sugars after UDP-galactosamine synthesis reaction.
Figure 4B:
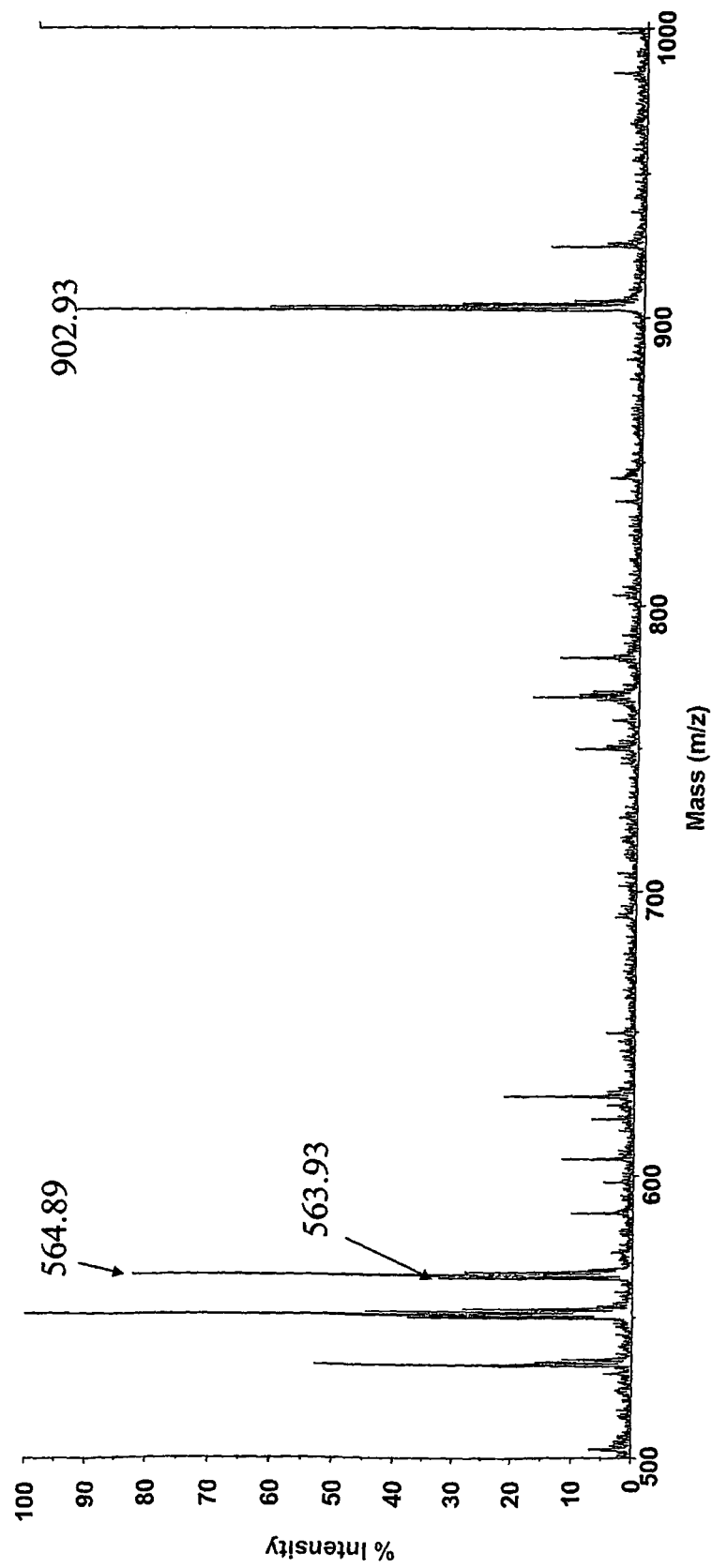
FIG. 4B. Negative ion linear mode MALDI-TOF mass spectrum of purified nucleotide sugars after the UDP-GalN-biotin synthesis reaction.
Figure 5:
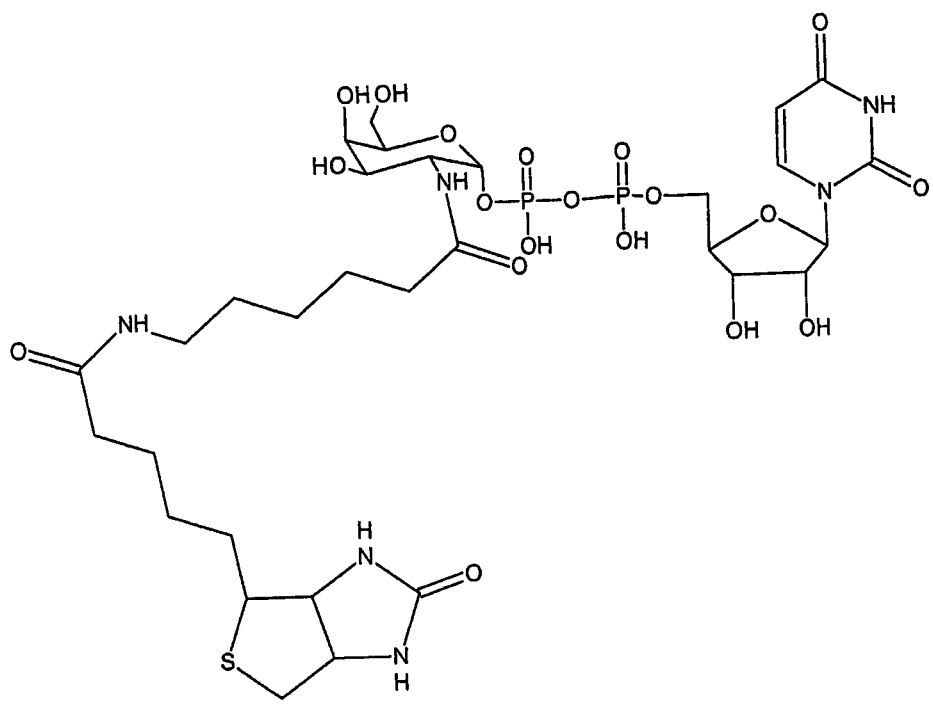
FIG. 5. Structure of UDP-GalN-biotin, uridine 5'-diphospho-N-(6-biotinamidohexanoyl)galactosamine.

Synthesis of UDP-GalN-biotin. UDP-galactosamine was synthesized as described under Materials and Methods. The product was characterized by MALDI-TOF MS (obs. m/z 564.42 for [$C_{15}H_{25}N_3O_{16}P_2$—H]$^-$, calc. m/z 564.31); FIG. 4A) and the expected peak appeared in the mass spectrum one mass unit smaller than the peak of UDP-Glc (obs. m/z 565.37 for [$C_{15}H_{24}N_2O_{17}P_2$—H]$^-$, calc. m/z 565.29); FIG. 4A). The crude nucleotide sugar preparate was reacted with a biotinylation reagent, namely succinimidyl-6-(biotinamido)hexanoate. After the reaction, the expected product could be seen in the MALDI-TOF mass spectrum of the reaction mixture (obs. m/z 902.93 for [$C_{31}H_{50}N_6O_{19}P_2S$—H]$^-$, calc. m/z 903.76; FIG. 4B). UDP-Glc did not react at all with the biotinylation reagent. The synthesized UDP-GalN-biotin, uridine 5'-diphospho-N-(6-biotinamidohexanoyl)galactosamine, reacted with GlcNAcβ1-3Galβ1-4GlcNAcβ1-3Galβ1-4Glc and a recombinant β1,4-galactosyltransferase similar to the enzyme described in (Ramakrishnan and Qasba, 2002). The product, [N-(6-biotinamidohexanoyl)galactosamine]β1-4GlcNAcβ1-3Galβ1-4GlcNAcβ1-3Galβ1-4Glc, was characterized by MALDI-TOF MS (obs. m/z for [M+Na]$^+$ 1433.38, calc. m/z 1433.55). Taken together, the results indicate that the synthesized product has the expected structure (FIG. 5). The product was chromatographically purified to homogeneity.

Example 8

Figure 6:
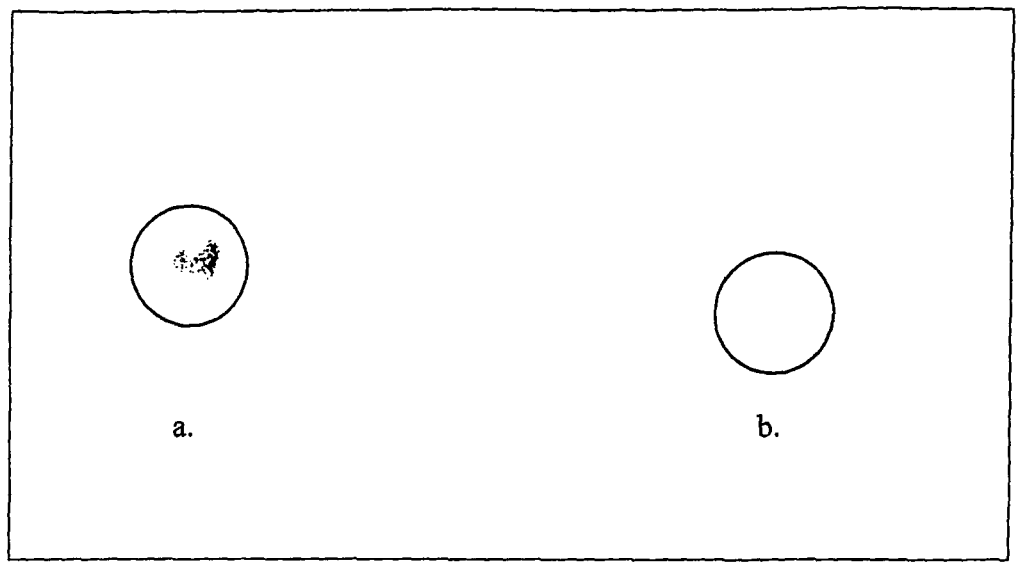
FIG. 6. Autoradiography of [$^{14}$C]Gal labelled lung adenocarcinoma (a.) and healthy lung tissue (b.) sections.

Labeling of terminal GlcNAc residues in tissue sections with UDP-[$^{14}$C]Gal and UDP-GalN-biotin. Deparaffinised formalin-fixed and paraffin-embedded tissue sections were radioactively labeled with UDP-[$^{14}$C]Gal and bovine milk 1,4-galactosyltransferase, as described under Materials and Methods. Autoradiography revealed a clear difference between the tumor and the healthy tissue samples (FIG. 6), indicating that there are highly elevated amounts of terminal GlcNAc residues in the lung adenocarcinoma sample. Similar results were also obtained by using the UDP-GalN-biotin reagent, as described under Materials and Methods, streptavin-FITC, and fluorescence microscopy. Importantly, cancer cells could be labeled with this biotinylation reagent.

Example 9

Isolation of [$^{14}$C]Gal-labeled oligosaccharides from lung adenocarcinoma sample. After labeling of lung adenocarcinoma sample and surrounding healthy tissue sections with [$^{14}$C]Gal as described above, the labeled oligosaccharides were isolated by N-glycosidase F digestion and nonreductive β-elimination. In the gel filtration chromatogram of the N-glycosidase F liberated glycans from lung adenocarcinoma (FIG. 7A), only one peak was visible and it coeluted with the N-glycan standards Galβ1-4GlcNAcβ1-2Manα1-6(Galβ1-4GlcNAcβ1-2Manα1-3)Manβ1-4GlcNAcβ1-4(Fucα1-6) GlcNAc and Galβ1-4[GlcNAcβ1-2Manα1-6(GlcNAcβ1-2Manα1-3)Manβ1-4GlcNAcβ1-4(Fucα1-6)GlcNAc]. The peak was pooled and subjected to HPLC with a porous graphitized carbon column (FIG. 7B), where it was divided into one major and two minor peaks. The major peak, containing nearly all of the total radioactivity, coeluted with the N-glycan standard Galβ1-4[GlcNAcβ1-2Manα1-6(GlcNAcβ1-2Manα1-3)Manβ1-4GlcNAcβ1-4(Fucα1-6) GlcNAc].

Figure 7C:
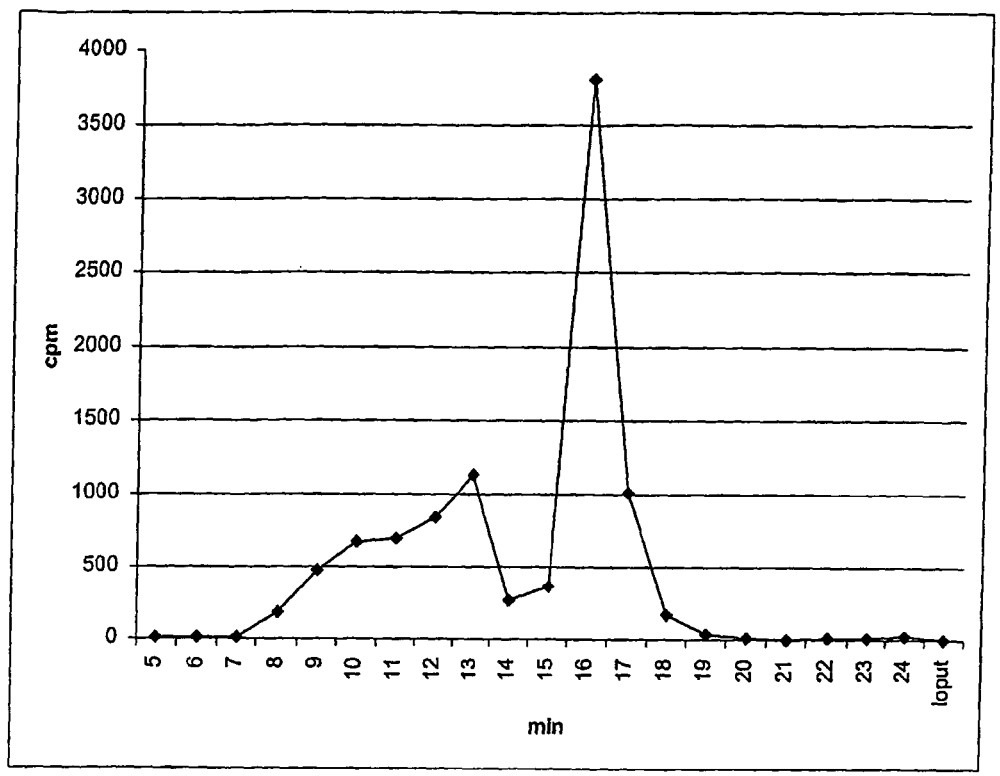
FIG. 7C. [$^{14}$C]Gal labelled material released by nonreductive β-elimination from lung adenocarcinoma sample. The material was subjected to gel filtration HPLC with a Superdex Peptide HR 10/30 column (Pharmacia, Sweden) in 50 mM NH$_4$HCO$_3$ at a flow rate of 1 ml/min. 1 ml fractions were collected and counted for radioactivity. Fractions at 8-15 min (pool 1) were pooled as well as at 15-18 min (pool 2).

In the gel filtration HPLC chromatogram of the material liberated by nonreductive β-elimination from lung adenocarcinoma (FIG. 7C), a broad peak, containing 45% of the total radioactivity, was found to elute between the void volume (at 8 ml) and the elution position of the N-glycan standard Galβ1-4[GlcNAcβ1-2Manα1-6(GlcNAcβ1-2Manα1-3) Manβ1-4GlcNAcβ1-4(Fucα1-6)GlcNAc]. The broad peak was pooled and passed through columns of strong cation exchange material and $C_{18}$ silica, which would retain all glycopeptidic material, but allow for quantitative elution of free oligosaccharides. Nearly 80% of the radioactivity in the pooled fractions was retained in the columns, indicating that the broad peak indeed corresponded to alkali-liberated glycopeptides, from which the [$^{14}$C]Gal labeled glycan moieties had not been detached. Major part of the remaining radioactivity was found to correspond to the N-glycan structure described above, but the presence of other labelled oligosaccharides could not be excluded. The major peak in the gel filtration BPLC chromatogram, containing 55% of the total radioactivity, coeluted with an N-acetyllactosamine (LacNAc) standard.

Example 10

Protein Linked GlcNAc from Cancer Samples

Furthermore, in graphitized carbon column HPLC of the pooled fractions at 15-18 min. the major peak coeluted with LacNAc. This suggests that the sample contains base-labile GlcNAc monosaccharide-protein conjugates, most likely GlcNAc-O-Ser/Thr units. Importantly, the amount of [$^{14}$C]-labeled LacNAc was significantly (1.99 times) higher in the lung adenocarcinoma sample as compared to the surrounding healthy tissue sample.

Taken together, these results indicate that about half of the total radioactivity that can be liberated from UDP-[$^{14}$C]Gal labeled lung adenocarcinoma sample tissue sections, represents the [$^{14}$C]Gal labeled forms of the cancer-associated N-glycan GlcNAcβ-Manα1-6(GlcNAcβ-Manα1-3)Manβ1-4GlcNAcβ1-4(Fucα1-6)GlcNAc. Furthermore, it is evident that also in the UDP-GalN-biotin reaction, the label is transferred into the oligosaccharide structures characterized above.

Example 11

Figure 8:
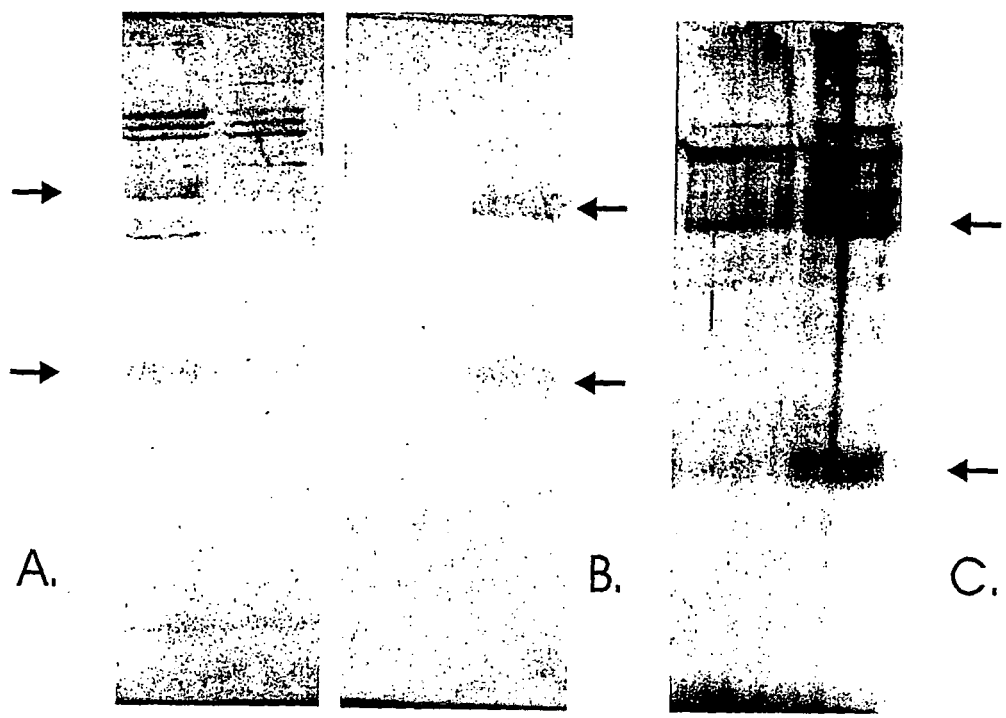
FIG. 8. Coomassie Blue stained reducing SDS-PAGE gels. Arrowheads indicate the positions of IgG heavy and light chains, respectively. (A.) Serum from a person who had recovered from mucinous ovarian adenocarcinoma, GlcNAcβ1-6(Galβ1-3)GalNAcα Sepharose; left: 0.5 M GlcNAc elution, right: acidic elution. (B.) IgG from pooled human sera, GlcNAcβ1-6(Galβ1-3)GalNAcα Sepharose; left: 0.5 M GlcNAc elution, right: acidic elution. (C.) Silver stained gel. Serum from a person who had recovered from mucinous ovarian adenocarcinoma, Galβ1-4GlcNAcβ1-6(Galβ1-3)GalNAcα Sepharose; left: 0.5 M GlcNAc elution, right: acidic elution.

Isolation of anti-GlcNAc antibodies from human serum. Human serum from a person who had recovered from mucinous ovarian adenocarcinoma, was passed through Sepharose columns that contained either GlcNAcβ1-6(Galβ1-3)GalNAcα or Galβ1-4GlcNAcβ1-6(Galβ1-3)GalNAcα epitopes covalently coupled to the gel. After washing, the columns were firstly eluted with a buffer containing 0.5 M GlcNAc (specific elution), and secondly with acidic buffer (unspecific elution). As a control, an IgG preparation from pooled human sera from healthy donors, i.e. persons who did not have a history of malignant diseases, was also subjected to the abovementioned chromatographical procedure. Reducing SDS-PAGE analysis was done to the collected fractions (FIG. 8). From the results it can be seen that two bands corresponding to proteins that had similar relative molecular weights to the heavy and light chains of an IgG standard, were eluted in the specific 0.5 M GlcNAc elution of GlcNAcβ1-6(Galβ1-3) GalNAcα Sepharose, but only in the serum sample of the person who had recovered from cancer. In contrast, no such specific elution could be detected in Galβ14GlcNAcβ1-6 (Galβ1-3)GalNAcα Sepharose chromatography of the two samples. According to their relative molecular weight, the specifically eluted proteins are likely to represent the heavy and light chain subunits of IgG or IgA, but not IgM human antibodies. The present results indicate the presence of elevated levels of terminal GlcNAc specific antibodies in serum of the person who had recovered from cancer, more specifically IgG and/or IgA antibodies that recognize the GlcNAcβ1-6(Galβ1-3)GalNAcα glycan epitope.

Example 12

Determination and Statistical Evaluation of Decreased Neutral N- and O-Glycan Galactosylation in Human Carcinomas Galactosylation Degree Calculation.

For galactosylation degree determinations, the non-sialylated glycan fractions from non-small cell lung carcinoma and from control samples from respective healthy lung tissue, were isolated and analyzed by MALDI-TOF mass spectrometry as described above. The galactosylation degrees were calculated as follows. The relative intensities (I) of three peaks in the mass spectra were measured, namely those at m/z 1485.5 (corresponding to the ion [Hex$_3$HexNAc$_4$dHex$_1$Na]$^+$, with two non-reducing terminal N-acetylglucosamine residues), m/z 1647.6 (corresponding to the ion [Hex$_4$HexNAc$_4$dHex$_4$Na]$^+$, with one non-reducing terminal N-acetyllactosamine group and one non-reducing terminal N-acetylglucosamine residue), and m/z 1809.6 (corresponding to the ion [Hex$_5$HexNAc$_4$dHex$_1$Na]$^+$, with two non-reducing terminal N-acetyllactosamine groups). The non-reducing terminal residues of these glycan components were previously determined as either N-acetylglucosamine according to sensitivity to digestion with glucosaminidase from Jack beans, or N-acetyllactosamine according to sensitivity to β-galactosidase digestion. The degree of galactosylation (DG) was calculated as the relation of galactosylated antennae N-acetylglucosamine residues to the total antennae N-acetylglucosamine residues, according to the formula:

$$DG = (I_{1647.6} + 2 \times I_{1809.6}) : (2 \times I_{1485.5} + 2 \times I_{1647.6} + 2 \times I_{1809.6}) \times 100\%$$

Statistical Calculations.

Statistical analyses were performed with the SAS Software (SAS System, version 8.2, SAS Institute Inc., Cary, N.C., USA), using SAS/STAT and SAS/BASE modules. All tests were performed as two-sided. The distributions of the experimental data were evaluated as 1) normal and symmetric, 2) only symmetric, or 3) non-symmetric and not normal, and the statistical test used was accordingly chosen as 1) Students t Test, 2) Wilcoxon Signed Rank Test, or 3) Sign Test. A p value of less than 0.05 was considered statistically significant.

Galactosylation Degree of Neutral Monofucosylated Biantennary N-glycans is Significantly Reduced in Non-Small Cell Lung Adenocarcinoma.

All tumor samples from a randomly picked group of 7 patients with non-small cell lung adenocarcinoma showed a decrease in the galactosylation degrees of neutral monofacosylated biantennary N-glycans, when compared to the respective control samples from the same patients. This difference is statistically significant (p=0.0156 in Wilcoxon Signed Rank Test). In addition, as described above, the difference seen in the mass spectra between tumor and healthy specimens was correlated to radiochemical staining of tissue sections prepared from the same specimens, when the sections were treated with C-14 labelled uridine diphosphogalactose and bovine milk β1,4-galactosyltransferase in galactosyltransferase reactions that were designed to quantitate non-reducing terminal N-acetylglucosamine residues in the sample glycoproteins. Moreover, the difference in radiochemical staining between the tumor and healthy control samples was the greatest when the respective difference in the degrees of galactosylation was the greatest, which allows for correlating the total amount of galactosyltransferase-sensitive non-reducing terminal β-N-acetylglucosamine residues in the tumor, with the mass spectrometric results obtained with isolated glycans from the tissue specimen.

Individual Lung Carcinoma, A Gastro-intestinal Carcinoma, And Kidney Hypernephroma Patients Show Severely Decreased Non-reducing Terminal Galactosylation of Their Glycoproteins.

In addition to the general decrease in the galactosylation degree in the lung cancer tumor samples, the analyzed samples from the patient group included individuals in which the phenomenon was very drastic. In these samples, the N-glycan peak at m/z 1485.5 was either the most abundant or the second most abundant neutral glycan signal in the mass spectra, indicating that the corresponding glycan structure had been specifically accumulated in the tumor cell glycoproteins. A similar phenomenon was also detected in tumor samples from individual patients of kidney carcinoma and a gastro-intestinal carcinoma, indicating that it is not restricted to lung carcinoma. The accumulation of non-reducing terminal β-N-acetylglucosamine containing N-glycans also characterized the isolated tumor protein-linked glycans from a patient with kidney hypernephroma, which had previously been analyzed for its glycolipid structures and found to contain also glycolipids characterized by decreased galactosylation. The latter correlation between glycoprotein and glycolipid structures further suggests that our observed accumulation of non-reducing terminal β-N-acetylglucosamine containing glycoconjugates is a result of a general defect in galactosylation that occurs in various forms of cancer.

Tumor Sample from an Individual Lung Carcinoma Patient that Shows Severely Decreased Non-reducing Terminal Galactosylation of O- and N-linked Glycoprotein Glycans.

Tumor sample from a non-small cell lung adenocarcinoma patient was studied in detail to elucidate the structures of various N-acetylglucosaminidase sensitive structures detected in the sample. Compared to healthy lung specimens, the mass spectrum of the non-sialylated glycan fraction from the paraffin-embedded and formalin-fixed tumor sample showed a significantly increased amount of a signal at m/z 609.23 (for $Hex_1HexNAc_2$, calc. m/z 609.21 for the ion $[M+Na]^+$) that can be assigned to a specific mucin-type O-glycan with specific exoglycosidase digestion reactions and MALDI-TOF mass spectrometry of the reaction products, as described below (mass spectra not shown). The above-mentioned glycan signal was not sensitive to Jack bean α-mannosidase digestion, whereas signals corresponding to high-mannose type N-glycans with molecular formulae $Man_{3-8}GlcNAc_2$ and $Man_{2-3}GlcNAc_2Fuc$, present in the same sample were transformed into peaks at m/z 609.16 for $Hex_1HexNAc_2$ and m/z 755.22 for $Hex_1HexNAc_2Fuc$, (calc. m/z 755.27), respectively. Similarly, β3-mannosidase digestion had no effect on the specific peak. However, β-N-acetylglucosaminidase from *S. pneunmoniae* did cleave the peak at m/z 609.23 that was transformed into a peak at m/z 405.77. corresponding to $Hex_1HexNAc$, (calc. m/z 406.13), which indicates for the presence of a non-reducing terminal β-N-acetylglucosamine residue in the glycan structure. In addition, recombinant β1,3-galactosidase partly transformed the peak into a peak at m/z 447.16, $HexNAc_2$ (calc. m/z 447.16). The present data indicates that a major component glycan in the peak at m/z 609.23 contains both non-reducing terminal β-N-acetylglucosamine and non-reducing terminal β1,3-linked galactose residues, and indicates that it contains the O-glycan Core 2 trisaccharide structure GlcNAcβ1-6(Gal,B-3)GalNAc. Compared to healthy lung tissue specimens, the mass spectrum of the sialylated glycan fraction from the same tumor contained a significantly increased amount of a signal that can be assigned to a sialylated counterpart of the neutral trisaccharide described above, namely at m/z 876.27 for $NeuAc_1Hex_1HexNAc_2$ (calc. m/z 876.31 for the ion $[M-H]^-$). The data indicates that this glycan signal corresponds to the sialylated form of the Core 2 O-glycan epitope detected among the neutral glycans from the same specimen, i.e. GlcNAcβ1-6(Neu5Acα2-3Galβ1-3)GalNAc.

By the action of *S. pneumoniae* β-N-acetylglucosaminidase, the peak at m/z 1485.61 in the non-sialylated glycan fraction of the same sample, corresponding to $Hex_3HexNAc_4Fuc_1$ (calc. m/z 1485.53), was transformed into the peak at m/z 1079.16, corresponding to $Hex_3HexNAc_2Fuc$, (calc. m/z 1079.38), and the peak at m/z 1647.67, corresponding to $Hex_4HexNAc_4Fuc$, (calc. m/z 1647.59), was transformed into the peak at m/z 1444.24, corresponding to $Hex_4HexNAc_3Fuc$, (calc. m/z 1444.51), which indicates that the corresponding glycans contain 2 and 1 non-reducing terminal β-N-acetylglucosamine residues, respectively. By the combined action of *S. pneumoniae* β1,4-galactosidase and recombinant β1,3-galactosidase, both the peaks at m/z 1647.67 and m/z 1809.72, the latter corresponding to $Hex_5HexNAc_4Fuc_1$ (calc. m/z 1809.64), were converted into the peak at m/z 1485.48, which indicates that the corresponding glycans contained non-reducing terminal β-galactose residues in N-acetyllactosamine terminal structures. Taken together, the glycan signals at m/z 1485.61, 1647.67, and 1809.72 represent a series of differently galactosylated glycan species. The galactosylation degree calculated from these three signals in the present tumor sample is 24%, which is significantly below the average 33% of the tumor samples from the group of 7 lung cancer patients described above. Furthermore, the simultaneous presence of the $Hex_1HexNAc_2$ and $NeuAc_1Hex_1HexNAc_2$ terminal β-N-acetylglucosamine residue-containing glycans in the present tumor sample indicates that there is a general decrease in galactosylation of non-reducing terminal β-N-acetylglucosamine residues in the protein-linked glycans of the particular tumor sample.

Example 13

Protein and Water Solution-compatible Conjugation Reagents

Preparation of UDP-GalN-PEG-fluorescein.

Figure 9:
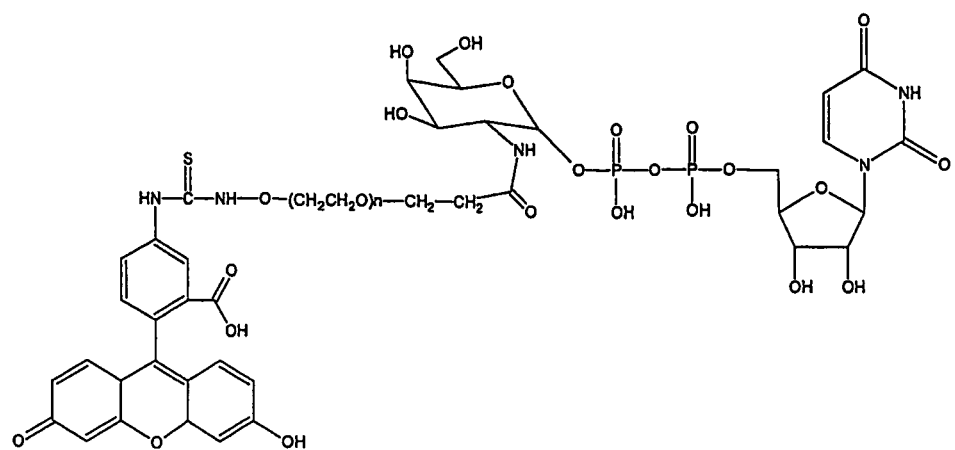
FIG. 9. The chemical structure of UDP-GalN-PEG-fluorescein reagent.
Figure 10A:
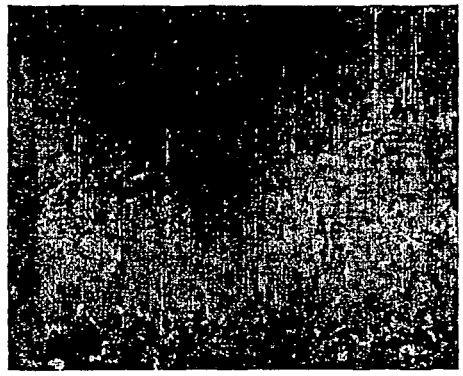
FIG. 10. Fluorescence microscopy of GalN-PEG-fluorescein labeled tumor tissue sections. A. Control reaction without the enzyme at 460-490 nm. B. Control reaction without the enzyme at 530-550 mL C. Reaction with the enzyme at 460-490 um. D. Reaction with the enzyme at 530-550 nm. E. Reaction with the enzyme at 460-490 nm. F. Reaction with the enzyme at 530-550 nm.
Figure 10B:
Figure 10C:
Figure 10D:
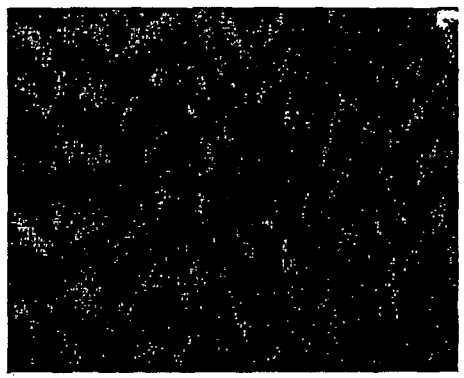
Figure 10E:
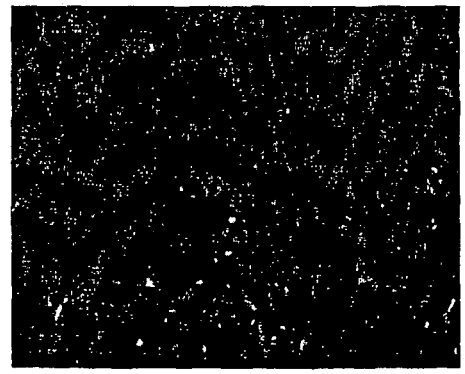
Figure 10F:
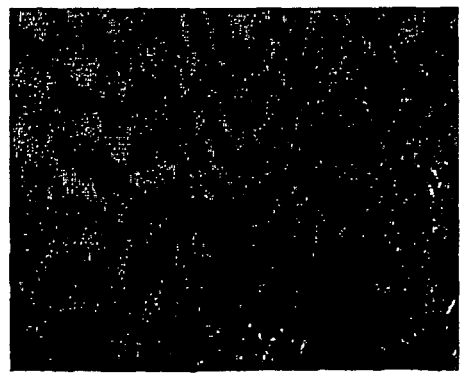

In 100 µl total reaction volume, 5 nmol uridine diphosphogalactosamine (UDP-GalN), 500 nmol fluorescein-poly(ethylene glycol)-NHS (MW 5000, Nektar Therapeutics, USA), and 500 nmol O-Benzotriazol-1-yl-N,N,N',N'-bis(tetramethylene)uronium hexafluorophosphate (Aldrich, USA), were incubated in ethylene glycol-dimethylformamide (1:1, v/v) containing 55 mM N-ethyldiisopropylamine, at room temperature for 60 hours. The reaction mixture was gel filtrated in a Superdex Peptide HR 10/30 column (Amersham Pharmacia Biotech) at 1 ml/min flow rate in 250 mM $NH_4HCO_3$ and the effluent was monitored with the UV detector at 214 nm, 261 nm, and 460 nm. Material eluted between 8 and 10 minutes, coeluting with the fluorescein-PEG starting material, was collected and dried. Anion exchange chromatography was performed on a Resource Q 1 ml column (Amersham Pharmacia Biotech) using $H_2O$-NaCl gradient. UV absorption at 214 nm, 261 nm, and 460 nm was monitored. Unbound material that contained the fluorescein-PEG starting material was discarded and the material eluting between 10 and 40 mM NaCl concentrations was collected. The fractions were analyzed by MALDI-TOF MS with a Voyager-DE STR BioSpectrometry Workstation in positive ion delayed extraction linear mode using 2,5-Dihydroxybenzoic acid (DHB) as the matrix. Mass spectrometry revealed that polyethylene glycol derivatives were presented in both fractions. Also UV absorption at 460 nm indicated that fluorescein was present in the both fractions. Taken together, the synthetized UDP-GalN-PEG-fluorescein (FIG. 9) was efficiently purified during the two chromatography steps.

Enzyme Reactions.

Formalin-fixed and parafin-embedded tissue sections from human non-small cell lung adenocarcinoma tumor tissue, were deparaffinised and covered with incubation mixture containing UDP-GalN-PEG-fluorescein as a sugar donor, 20 mM $MnCl_2$, 10 mM Tris-HCl pH 8.0, and a mutant galactosyltransferase enzyme similar to the one described by Ramakrishnan and Qasba (2002). A negative control reaction contained the same incubation mixture without the enzyme. Reactions were incubated at 37° C. for 20 hours, after which the tissue sections were washed with water. The fluorescent samples were analyzed by Olympus AX70 Provis fluorescence microscope. After the reaction, the samples showed clear positive cells at wavelengths 460-490 nm (FITC) within the tumor tissue (FIG. 10.E). The fluorescence was in the cytoplasm as well as in the membrane on the positive cells (FIG. 10.C). However, the control samples remained negative (FIG. 10.A) showing only some autofluorescence (FIG. 10.B). However, the samples analyzed at wavelengths 530-550 nm were negative, indicating that the positive results were not due to autofluorescence (FIG. 10.D, 10.F). In conclusion, this example described how the enzyme catalysed the ex vivo transfer of GalN-PEG-fluorescein groups from UDP-GalN-PEG-fluorescein to non-reducing terminal N-acetylglucosamine (GlcNAc) residues present in glycoprotein glycans of human tumor cells and tumor tissue sections.

Preparation and Use of Various Conjugation Reagents

In different reactions, carboxylic acid reagents that were successfully incorporated to the 2-amino group of uridine diphosphogalactosamine through amidation, included S-acetyl-3-mercaptopropionic acid, 4-mercaptobutyric acid, Boc-2-aminooxyacetic acid, and N-maleinimido-6-aminohexanoic acid, which are suitable for protein-compatible water-solution coupling of N-maleimido, aldehyde, and thiol group containing reagents or biologically active substances, respectively. The 3-mercaptopropionic acid conjugate was primarily produced as acetate protected form and the 2-aminooxyacetic acid conjugate as t-Boc protected form, and the protective groups can be completely removed by incubation in mild alkaline aqueous solution or trifluoroacetic acid, respectively. After purification, the structures of the conjugation reagents were confirmed by MALDI-TOF mass spectrometry and found to contain the desired functional groups attached to the galactosamine residue. In test reactions, the reagents were incubated in aqueous solution with a non-reducing terminal N-acetylglucosamine containing glycoconjugate and a modified galactosyltransferase enzyme similar to the one described by Ramakrishnan and Qasba (2002), which resulted in the successful transfer of conjugation reagent-modified galactosamine residues to the glycoconjugates, evidenced by MALDI-TOF mass spectrometry as a mass increase of the acceptor glycoconjugate, equivalent to the galactosamine-reagent conjugate (mass spectra not shown).

Example 14

Increased Levels of Specific Antibodies Against Non-reducing Terminal N-acetylglucosamine Containing Glycoconjugates in Serum of Cancer Patients A group of four people with various stages of diagnosed cancer of the gastrointestinal tract or the ovary, was studied by analyzing serum samples for their concentrations of IgG and IgM antibodies against specific carbohydrate epitopes. The assay consisted of binding of specific antibodies from serum to synthetic glycoconjugates, washing, and then detecting the specifically bound antibody levels in ELISA with enzyme-labelled anti-human IgG or anti-human IgM secondary antibodies and quantitation of specific reaction products. The obtained results are depicted in Table 2. Both IgG and IgM levels against a non-reducing terminal N-acetylglucosamine containing N-glycan were elevated in one patient. Antibody levels against the Core 2 trisaccharide GlcNAcβ1-6(Galβ1-3)GalNAc were elevated in the whole patient group, but the specific antibody response varied: in one patient both IgG and IgM levels were elevated, in one patient mainly IgG, and in two patients mainly IgM. Antibody response against the GlcNAcβ1-3GalNAc disaccharide showed an identical pattern of antibody type response in the patient group. Two patients showed elevated serum levels of mainly IgM and one patient mainly IgG antibodies against an O-glycosidic β-GlcNAc epitope.

TABLE 2

Specific antibody responses against carbohydrate epitopes expressed as antibody signal intensities from which the assay background has been subtracted.

| | Saccharide | | | | |
| --- | --- | --- | --- | --- | --- |
| | 1 | 2 | 3 | 4 | 5 |
| Patient 1 IgG | 0 | 0 | 0.039 | 0 | 0.017 |
| Patient 1 IgM | 0 | 0.259 | 0.091 | 0.159 | 0.125 |
| Patient 2 IgG | 0 | 0.022 | 0.078 | 0.082 | 0.094 |

TABLE 2-continued

Specific antibody responses against carbohydrate epitopes expressed as antibody signal intensities from which the assay background has been subtracted.

|  | Saccharide | | | | |
| --- | --- | --- | --- | --- | --- |
|  | 1 | 2 | 3 | 4 | 5 |
| Patient 2 IgM | 0 | 0.079 | 0.008 | 0.029 | 0.041 |
| Patient 3 IgG | 0.006 | 0 | 0 | 0.013 | 0 |
| Patient 3 IgM | 0.01 | 0.1 | 0.068 | 0.122 | 0.011 |

TABLE 2-continued

Specific antibody responses against carbohydrate epitopes expressed as antibody signal intensities from which the assay background has been subtracted.

|  | Saccharide | | | | |
| --- | --- | --- | --- | --- | --- |
|  | 1 | 2 | 3 | 4 | 5 |
| Patient 4 IgG | 0 | 0 | 0 | 0 | 0 |
| Patient 4 IgM | 0 | 0.463 | 0.042 | 0 | 0.056 |

Saccharide 1: GlcNAcβ1-2Manα1-6(GlcNAcβ1-2Manα1-3)Manβ1-4GlcNAcβ1-4(Fucα1-6)GlcNAcβ-N-Asn-R,
Saccharide 2: positive cancer-associated saccharide,
Saccharide 3: GlcNAcβ1-6(Galβ1-3)GalNAcα-O—CH$_2$—R,
Saccharide 4: GlcNAcβ-O—CH$_2$—R,
Saccharide 5: GlcNAcβ1-3GalNAcα-O—CH$_2$—R.
R: variable linker.

Example 15

Activity of β1,4-Galactosyltransferase in Human Serum and Activation of Added β1,4-galactosvsyltransferase Under Various Reaction Conditions Fresh human blood sample was collected from blood group B-individual (5 ml). After clotting for 30 min it was centrifuged at +4° C., 2000 rpm for 25 minutes, and the serum was collected for experiments (2 ml, stored on ice).

Reactions were performed with 50 nmol of acceptor saccharide (GlcNAcβ1-3Galβ1-4GlcNAc, from enzymatic synthesis, purified by ion exhange and gel filtration, characterized by NM and mass spectrometry), 5 mmol UDP-[$^{14}$C]Gal (mixture of nonlabelled and radioactive, radioactivity was 100 000 cpm) and 20 µl of fresh human serum (total volume was 20 µl). Reaction conditions were varied by adding cations and bovine milk p 1,4-galactosyltransferase (β1,4GalT).
Results By adding 2 mU of β1,4GalT alone showed clear galactosyltransferase activity, purified galactosylated tetrasaccharide sample had 534 cpm (Table 3). The backround is likely radioactive Gal released from donor substrate. Adding 0.1 mM Zn$^{2+}$ to reaction mixture doubled the product formation. Further addition of 4 mM MgCl$_2$, and 2 mM CaCl$_2$ increased additionally the amount of product.

Similar increasing in product formation was with Mn$^{2+}$-addition, but without external β1,4GalT, other salts used in the experiment did not activate the endogenous galactosyltransferase activity of human serum. Also MnCl$_2$ at lower concentration than 5 mM was able to activate the endogenous enzyme in the biological solution (not shown). Notable is also that background was lower with Mn$^{2+}$ and Zn$^{2+}$ together with fosforylcholine. Fosforylcholine may inhibit enzyme activities of serum which degradate the donor nucleotide.

TABLE 3

| Changes in reaction mixture | Product (cpm) | Background (cpm) |
| --- | --- | --- |
| No salt, 2 mU β1, 4GalT | 534 | 5104 |
| 0.1 mM ZnCl$_2$, 2 mU β1, 4GalT | 1022 | 4446 |
| 0.1 mM ZnCl$_2$, 2 mU β1, 4GalT, 4 mM MgCl$_2$, 2 mM CaCl$_2$ | 1292 | 4546 |
| 0.1 mM ZnCl$_2$, 1 mM fosforylcholine 2 mU β1, 4GalT | 872 | 2552 |
| 5 mM MnCl$_2$ | 566 | 1079 |
| 1 mM MnCl$_2$ | 1073 | 2068 |
| 0.2 mM MnCl$_2$ | 457 | 4578 |

Example 16 a) The oligosaccharide structure GlcNAcβ3Galβ4GlcNAcβ3Galβ4Glc is receptor for the gastric pathogen *Helicobacter pylori*. The structure is changed to 10-fold weaker receptor structure Gal34GlcNAcα3Galβ4GlcNAcβ3Galβ4Glc by incubating it with UDP-Gal and β4-galactosyltransferase from bovine milk.

b) The oligosaccharide receptor GlcNAcβ3Galβ4GlcNAcβ3Galβ4Glc is incubated with GDP-Fuc and soluble human fucosyltransferase VI corresponding to major the fucosyltransferase from human milk. MALDI-TOF mass spectrometric analysis reveled a major peak corresponding to GlcNAcβ3Galβ4(Fucα3)GlcNAcβ3Galβ4Glc, the structure is confimed by NMR-spectroscopy.

c) Erythrocytes from a patient suffering from glycosylation deficiency causing high levels of terminal GlcNAc-structures including GlcNAcβ3Galβ4GlcβCer are incubated with radiolabeled UDP-Gal and βgalactosyltransferase. Transfer of labeled galactose on the cell surface is observed. The galactosylation of the cells reduces the reactivity of the cells with anti-GlcNAc-antibodies.

REFERENCES

Ångström, J., and Karl-Anders Karlsson (1996) Glycobiology 6, 599-609.
Arap, W., Pasqualini, R. and Ruoslahti, E. (1998) Science 279, 323-4.
Endo et al. (1996) Eur. J. Biochem 236:579-590.
Ernst, B., Hart, G. W., and Sinaÿ, P. (eds.) (2000) Crbohydrates in chemistry and biology, ISBN 3-527-29511-9, Weiley-VHC, Weinheim.
Hanisch, P.-G., Koldovsky, U., and Borchard F. (1993) Cancer Res. 53, 4791-4796.

Hansson, G. C., Karlsson, K.-A., Larson G., Strömberg, N., and Thurin, J. (1985) Anal. Biochem. 146, 158-63.
Harvey, D. J., et al. (1993) Rapid Commun. Mass Spectrom. 7(7):614-9.
Hounsell, E. F., Lawson, A.M., Stoll, M., Kane, D. P., Cashmore, G. C., Carruthers, R. A.,
Feeney, J., and Feizi, T. (1989) Eur. J. Biochem. 186, 597-610.
Holmes, E. H., and Greene, T. G. (1991) Arch. Biochem. Biophys. 288, 87-96.
Hu, J., Stults, C. L. M., Holmes, E. H., and Macher, B. A. (1994) Glycobiology 4, 251-257.
Nakamura, M., Tsunoda, A., Sakoe, K., and Saito, M. (1993) Biochem. Biophys. Res. Communu. 197 1025-1033.
Manzi, A. E., et al. (2000) Glycobiology 10(7):669-89.
Meichenin M. et al. (2000) Cancer Research 60:5499-5507.
Mäki, M., et al. (2002) Eur. J. Biochem. 269(2):593-601.
Nyman, T. A., et al. (1998) Eur. J. Biochem. 253(2):485-93.
Packer, N. H., et al. (1998) Glycoconj. J. 15(8):737-747.
Ramakrishnan, B., and Qasba, P. K. (2002) J. Biol. Chem. 277(23):20833-9.
Papac, D. I., et al. (1996) Anal. Chem. 68(18):3215-23.
Rhen M., Klemm P., and Korhonen T. K. (1986). J Bacteriol 168, 123442.
Saarinen, J., et al. (1999) Eur. J. Biochem. 259(3):829-40.
Sadamoto, R., Nikura, K., Nishimura, S.-I. (2001) Chemical engineering of bacterial cell wall. Poster C13.8, XVI International Symposium on Glycoconjugates August 19.-24. 2001 Haag Netherlands, *Glycoconjugate J.* no. 1/2001.
Spillmann, A., and Finne, J. (1994) Eur. J. Biochem. 220, 385-394.
Symington, F. W, Hendersson, B. A., and Hakomori, S.-I. (1984) Mol. Immunol. 21, 877-882.
Teneberg, S., Lonnroth, I., Torres López, J. T., Galili, U., Ölwegård Halvarsson, M.,
Verostek, M. F., et al. (2000) Anal. Biochem. 278:111-122.
Teneberg S, Ångstrom J, Jovall P-Å, and Karlsson K-A. (1994) *J. Biol Chem* 269, 855463
Viitala, J., and Finne, J. (1984) Eur. J. Biochem. 138, 393-397.

What is claimed:

1. A composition comprising: an enzyme substrate which comprises a 2-modified Gal(N) or Glc(N) comprising UDP-Gal(N) or UDP-Glc(N); and a transferring enzyme which is a UDP-Gal galactosyltransferase, which is engineered to transfer effectively 2-modified Gal(N) or Glc(N) from 2-modified UDP-Gal(N) or UDP-Glc(N), wherein the galactosyltransferase comprise mutations corresponding to bovine Gal-T1 Y289L or human Gal-T1 Y286L.

2. The composition according to claim 1, wherein the galactosyltransferase is a β4-GalNAc and/or β4-GlcNAc-transferase capable of transferring effectively 2-modified Gal(N) or Glc(N) from 2-modified UDP-Gal(N) or UDP-Glc(N).

3. The composition according to claim 2, wherein the enzyme substrate is capable of being transferred to glycoconjugate, O-glycan or N-glycan.

4. The composition according to claim 3, wherein the enzyme substrate is capable of being transferred to terminal GlcNAc.

5. The composition according to claim 1, wherein the galactosyltransferase is a natural β4-GalNAc and/or β4-GlcNAc- transferase.

6. The composition according to claim 3, wherein the composition further comprises a transferred 2-modifed Gal(N) or Glc(N) linked to the GlcNAc residue of a glycoconjugate, O-glycan or N-gylcan.

7. The composition according to claim 1, wherein said enzyme substrate is conjugated to an immunologically active substance and/or a toxic substance.

8. The composition according to claim 1, wherein said enzyme substrate is capable of being transferred specifically to the surface of a pathogenic entity or malignant cell or tissue by the transferring enzyme.

9. The composition according to claim 1, wherein said enzyme substrate is according to the Formula UDP-GalN[—S-]-D, wherein S is an optional spacer group, D is a derivatizing group including molecular labels selected from the group consisting of biotin, a fluorescent molecule, a toxic agent, a prodrug and a prodrug releasing substance.

10. The composition according to claim 1, wherein the modification on position 2 includes a chemoselective linking group.

11. The composition according to claim 10, wherein the chemoselective linking group is selected from the group consisting of: linking group effective in water solutions or aqueous buffers, protein and tissue compatible linking group, which does not react, or does not essentially react with amino acid residues or other structures present on the material to be targeted, a thiol group, an aldehyde group, a ketone group and an amino-oxy group.

12. The composition according to claim 1, wherein the composition further comprises divalent cations.

13. The composition according to claim 12, wherein said divalent cations include $Mg^{2+}$ and $Ca^{2+}$.

14. The composition according to claim 1, wherein said composition is a pharmaceutical composition.

15. The composition according to claim 1, wherein said substrate is according to the following formula C2:

$$Nu-Hex(L-S-T) \qquad \text{Formula C2,}$$

wherein
Nu is UDP,
Hex is Gal or Glc,
L is a linking atom on carbon 2 of the hexose,
S is a spacer group, an atom or is not present, and
T is a group to be transferred or targeted.

16. The composition according to claim 1, wherein the enzyme substrate, which comprises the 2-modified Gal(N) or Glc(N), is capable of being transferred to terminal β-GlcNAc residue.

17. The composition according to claim 1, wherein the enzyme substrate is capable of being transferred to a cell, tissue or therapeutic protein.

18. The composition according to claim 1, wherein the enzyme substrate is capable of being transferred to monosaccharide or oligosaccharide.

19. The composition according to claim 1, wherein the enzyme substrate is capable of being transferred to glycoconjugate, O-glycan or N-glycan.

20. The composition according to claim 1, wherein the enzyme substrate is capable of being transferred to terminal GlcNAc.

21. A method of modifying a carbohydrate comprising a step of:
contacting the composition as defined in claim 1 with an acceptor substrate comprising an oligosaccharide, O-glycan, N-glycan or monosaccharide.

22. The method according to claim 21, wherein said enzyme substrate is conjugated to an immunologically active substance and/or a toxic substance.

23. The method according to claim 21, wherein said enzyme substrate is capable of being transferred specifically to the surface of a pathogenic entity or malignant cell or tissue by the transferring enzyme.

24. The method according to claim 21, wherein said enzyme substrate is according to the Formula UDP-GalN[—S-]-D, wherein S is an optional spacer group, D is a derivatizing group including molecular labels selected from the group consisting of biotin, a fluorescent molecule, a toxic agent, a prodrug and a prodrug releasing substance.

25. The method according to claim 21, wherein the modification on position 2 includes a chemoselective linking group.

26. The method according to claim 25, wherein the chemoselective linking group is selected from the group consisting of: linking group effective in water solutions or aqueous buffers, protein and tissue compatible linking group, which does not react, or does not essentially react with amino acid residues or other structures present on the material to be targeted, a thiol group, an aldehyde group, a ketone group and an amino-oxy group.

27. The method according to claim 21, wherein the enzyme substrate is capable of being transferred to a cell, tissue or therapeutic protein.

* * * * *